US008119259B2

(12) United States Patent
Kadoma et al.

(10) Patent No.: US 8,119,259 B2
(45) Date of Patent: Feb. 21, 2012

(54) QUINOXALINE DERIVATIVE, AND LIGHT-EMITTING ELEMENT AND ELECTRONIC DEVICE USING THE SAME

(75) Inventors: Hiroshi Kadoma, Kanagawa (JP); Sachiko Kawakami, Kanagawa (JP); Satoko Shitagaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 514 days.

(21) Appl. No.: 12/277,451

(22) Filed: Nov. 25, 2008

(65) Prior Publication Data

US 2009/0140642 A1    Jun. 4, 2009

(30) Foreign Application Priority Data

Nov. 30, 2007    (JP) ................... 2007-310065

(51) Int. Cl.
*H01L 51/54* (2006.01)
*C09K 11/00* (2006.01)
(52) U.S. Cl. ........ 428/690; 428/917; 544/353; 313/504; 313/506; 252/301.16; 252/301.28; 257/40
(58) Field of Classification Search .................. None
See application file for complete search history.

(56) References Cited

U.S. PATENT DOCUMENTS

| | | | |
|---|---|---|---|
| 5,077,142 A | 12/1991 | Sakon et al. | |
| 7,227,313 B2 | 6/2007 | Huiberts et al. | |
| 2005/0118454 A1 | 6/2005 | Nakaya et al. | |
| 2005/0186446 A1 | 8/2005 | Shitagaki et al. | |
| 2008/0036369 A1 | 2/2008 | Tokuda et al. | |
| 2008/0091012 A1 | 4/2008 | Egawa et al. | |
| 2009/0140641 A1 | 6/2009 | Nomura et al. | |
| 2009/0184633 A1 | 7/2009 | Kadoma et al. | |
| 2009/0203704 A1 | 8/2009 | Kadoma et al. | |

FOREIGN PATENT DOCUMENTS

| | | |
|---|---|---|
| EP | 1 616 864 A1 | 1/2006 |
| JP | 7-142169 | 6/1995 |
| JP | 2003-40873 | 2/2003 |
| JP | 2004-200162 | 7/2004 |
| JP | 2006-16384 | 1/2006 |
| JP | 2006-89728 | 4/2006 |
| WO | WO 2004/094389 A1 | 11/2004 |
| WO | WO 2006/022193 A1 | 3/2006 |

OTHER PUBLICATIONS

Thomas, K.R.J. et al, "Quinoxalines Incorporating Triarylamines: Potential Electroluminescent Materials with Tunable Emission Characteristics," Chemistry of Materials, vol. 14, No. 6, Jun. 2002, pp. 2796-2802.
Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID Digest 04: SID International Symposium Digest of Technical Papers, 2004, pp. 900-903.
Thomas, K.R.J. et al, "Chromophore-Labeled Quinoxaline Derivatives as Efficient Electroluminescent Materials," Chemistry of Materials, vol. 17, No. 7, Apr. 5, 2005, pp. 1860-1866.
Dorwald, F.Z., *Side Reactions in Organic Synthesis, A Guide to Successful Synthesis Design*, Wiley-VCH Verlag GmbH & Co. KGaA, 2005, preface, p. IX.
Chen, S. et al, "New Organic Light-Emitting Materials: Synthesis, Thermal, Photophysical, Electrochemical and Electroluminescent Properties," Database Caplus on STN, AN 2006:1296274, DN 146:260905, Journal of Physical Chemistry, vol. 111, No. 2, 2007, pp. 1029-1034.
Xiao, L. et al, "Highly Efficient Electron-Transporting Phenanthroline Derivatives for Electroluminescent Devices," Chemistry Letters, vol. 36, No. 6, 2007, pp. 802-803.
Krueger, H. et al, "Some New Electron-Affine Polymers for Organic Photovoltaics," Proceedings of SPIE, vol. 5215, 2004, pp. 141-152.
Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID Digest 04: SID International Symposium Digest of Technical Papers, vol. 35, No. 2, May 26-27, 2004, pp. 900-903.

*Primary Examiner* — Jennifer A Chriss
*Assistant Examiner* — Michael H Wilson
(74) *Attorney, Agent, or Firm* — Husch Blackwell LLP

(57) ABSTRACT

An object is to provide a novel quinoxaline derivative. Another object is to provide a light-emitting element with low driving voltage and less power consumption. Further, another object is to provide a light-emitting device and an electronic device each consuming less power by using the light-emitting element. A quinoxaline derivative represented by a general formula (G11) is provided, in which at least one of carbon at a 2-position and carbon at a 3-position, and carbon at a 2-position of benzoxazole are bound via an arylene group.

24 Claims, 29 Drawing Sheets

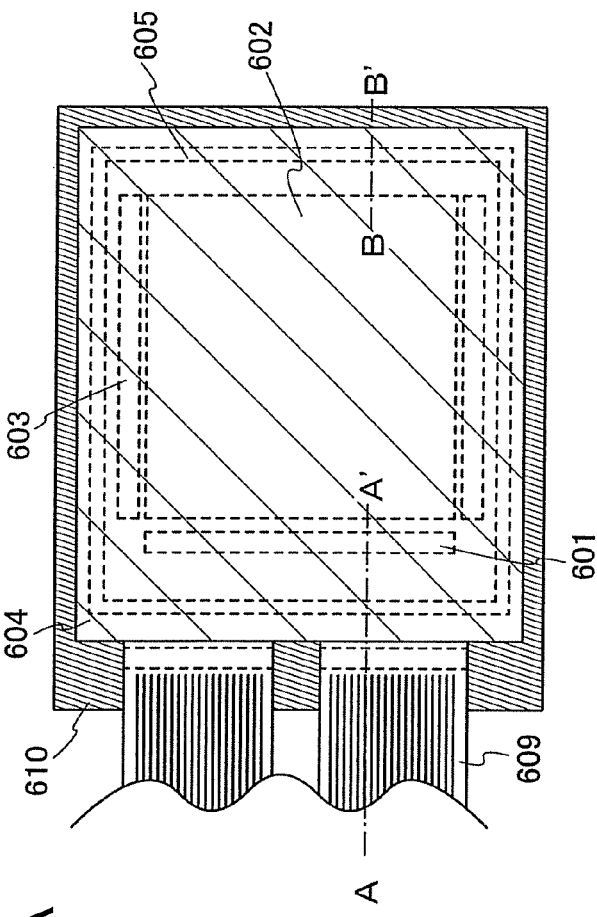
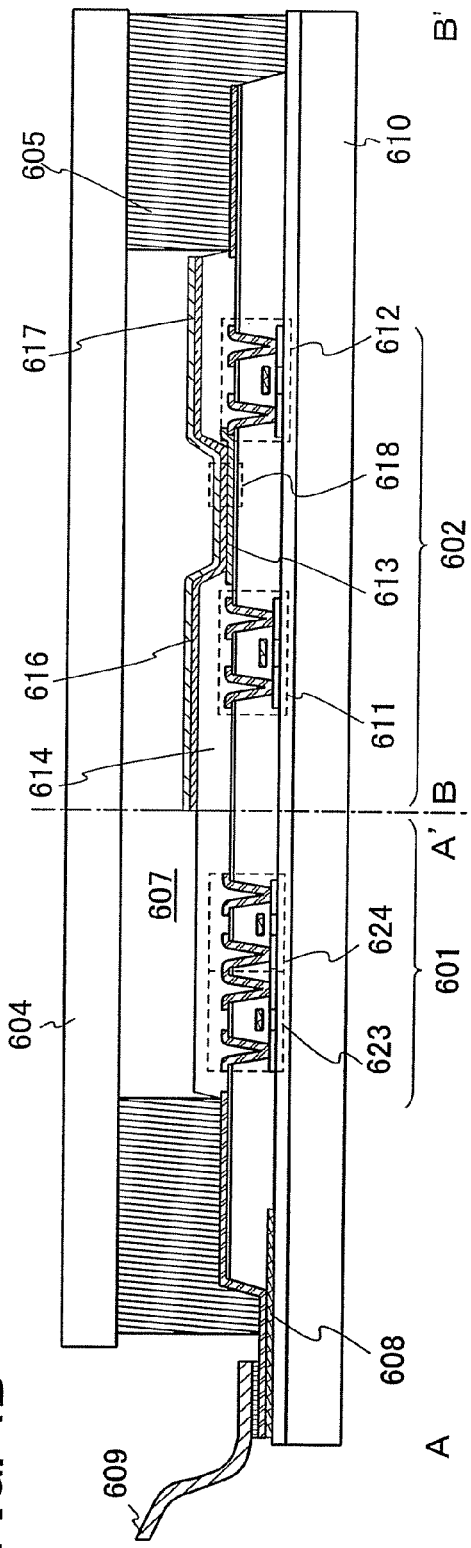
FIG. 4A
FIG. 4B

QUINOXALINE DERIVATIVE, AND LIGHT-EMITTING ELEMENT AND ELECTRONIC DEVICE USING THE SAME

BACKGROUND OF THE INVENTION

1. Field of the Invention

The present invention relates to a quinoxaline derivative, and further relates to a light-emitting element, a light-emitting device, and an electronic device using the quinoxaline derivative.

2. Description of the Related Art

An organic compound can take various structures compared with an inorganic compound, and it is possible to synthesize materials having a variety of functions by appropriate molecular-design of an organic compound. Owing to these advantages, photo electronics and electronics which use a functional organic material have been attracting attention in recent years.

For example, a solar cell, a light-emitting element, an organic transistor, and the like are exemplified as electronic devices utilizing an organic compound as a functional material. These are devices taking advantage of electric properties and optical properties of the organic compound. Among them, in particular, a light-emitting element has been making remarkable development.

It is recognized that the light emission mechanism of a light-emitting element is as follows: when voltage is applied between a pair of electrodes which sandwich a light-emitting layer, electrons injected from a cathode and holes injected from an anode are recombined in the light-emitting layer to form a molecular exciton, and energy is released to emit light when the molecular exciton relaxes to the ground state. A singlet excited state and a triplet excited state are known as excited states, and light emission is considered to be possible through any of the excitation states.

In improving element characteristics of such a light-emitting element, there are a lot of problems depending on a material, and in order to solve the problems, improvement of an element structure, development of a material, and the like have been carried out.

For example, tris(8-quinolinolato)aluminum(III) (abbreviation: Alq) is widely used as an electron transporting material of the light-emitting element (see Non-Patent Document 1: Taishi Tsuji, et al., SID 04 DIGEST, 35, PP900-903 (2004)). However, development of materials having more excellent characteristics such as high mobility is desired. In particular, in view of commercialization, less power consumption is an important object, and development of a material and a light-emitting element having further improved characteristics have been desired.

SUMMARY OF THE INVENTION

An object of the present invention is to provide a novel quinoxaline derivative which solves the above problems.

Another object of the present invention is to provide a light-emitting element with low driving voltage. Further, another object of the present invention is to provide a light-emitting element with less power consumption. Furthermore, another object is to provide a light-emitting device and an electronic device each having less power consumption by using such a light-emitting element.

As the results of diligent study, the present inventors have synthesized a quinoxaline derivative in which at least of one of carbon at a 2-position and a 3-position of quinoxaline and carbon at a 2-position of benzoxazole are bound via an arylene group, and have found that the quinoxaline derivative can be preferably used for a light-emitting element. In other words, as the results of diligent study, the present inventors have synthesizesd a quinixaline derivative in which one of carbon at a 2-position and a 3-position of quinoxaline or the both carbon thereof, and carbon at a 2-position of benzoxazole are bound via an arylene group, and have found that the quinoxaline devicative can be preferably used for a light-emitting element.

The present invention is broadly divided into two modes, i.e., a case of a quinoxaline derivative in which one of carbon at a 2-position and carbon at a 3-position of quinoxaline, and carbon at a 2-position of benzoxazole are bound via an arylene group, and a case of a quinoxaline derivative in which carbon at a 2-position of quinoxaline and carbon at a 2-position of benzoxazole are bound via an arylene group and carbon at a 3-position of the quinoxaline and carbon at a 2-position of benzoxazole are bound via an arylene group. Therefore, one aspect of the present invention is a quinoxaline derivative represented by a general formula (G11), which is a quinoxaline derivative of a mode in which one of carbon at a 2-position and carbon at a 3-position of quinoxaline, and carbon at a 2-position of benzoxazole are bound via an arylene group.

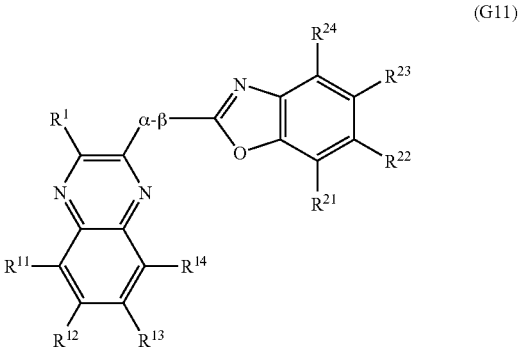

(G11)

In the formula, α represents a substituted or unsubstituted arylene group having 6 to 13 carbon atoms; β represents a substituted or unsubstituted arylene group having 6 to 13 carbon atoms; $R^{21}$ to $R^{24}$ may be the same or different from each other and each represent hydrogen or an alkyl group having 1 to 4 carbon atoms; $R^1$ represents an alkyl group having 1 to 4 carbon atoms or a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

Another of aspect of the present invention is a quinoxaline derivative represented by a general formula (G12).

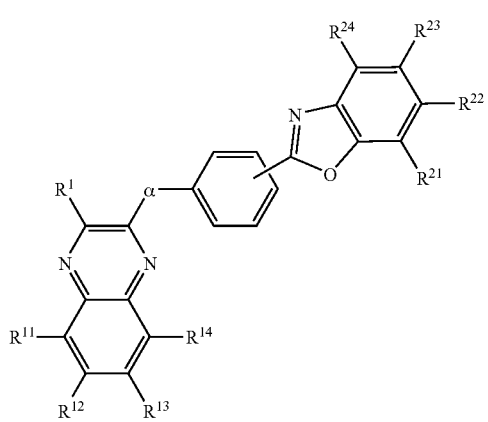

(G12)

In the formula, α represents a substituted or unsubstituted arylene group having 6 to 13 carbon atoms; $R^{21}$ to $R^{24}$ may be the same or different from each other and each represent hydrogen or an alkyl group having 1 to 4 carbon atoms; $R^1$ represents an alkyl group having 1 to 4 carbon atoms or a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

Another aspect of the present invention is a quinoxaline derivative represented by a general formula (G13).

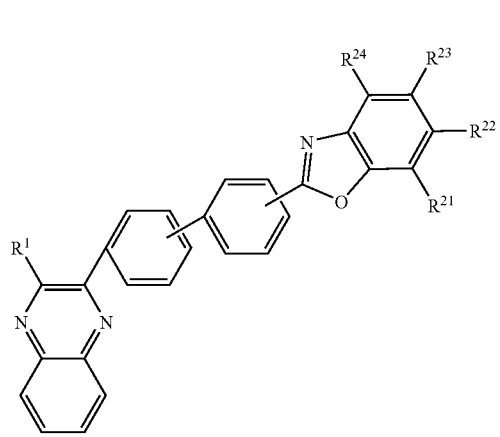

(G13)

In the formula, $R^{21}$ to $R^{24}$ may be the same or different from each other and each represent hydrogen or an alkyl group having 1 to 4 carbon atoms; and $R^1$ represents an alkyl group having 1 to 4 carbon atoms or a substituted or unsubstituted aryl group having 6 to 13 carbon atoms.

Another aspect of the present invention is a quinoxaline derivative represented by a general formula (G14).

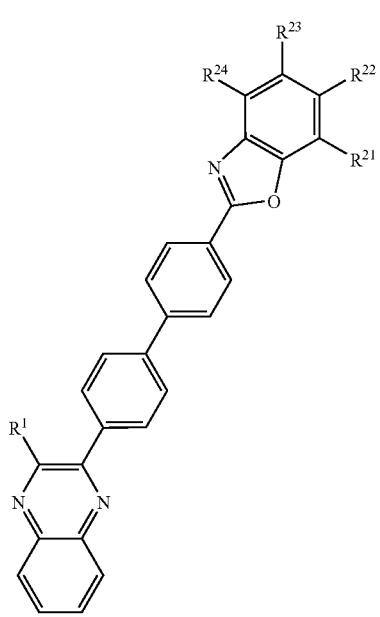

(G14)

In the formula, $R^{21}$ to $R^{24}$ may be the same or different from each other and each represent hydrogen or an alkyl group having 1 to 4 carbon atoms; and $R^1$ represents an alkyl group having 1 to 4 carbon atoms or a substituted or unsubstituted aryl group having 6 to 13 carbon atoms.

In the above structure, $R^1$ is preferably a phenyl group or a biphenyl group.

Another aspect of the present invention is a quinoxaline derivative represented by a general formula (G21), which is a quinoxaline derivative of a mode in which carbon at a 2-position of quinoxaline and carbon at a 2-position of benzoxazole are bound via an arylene group and a 3-position of the quinoxaline and carbon at a 2-position of benzoxazole are bound via an arylene group.

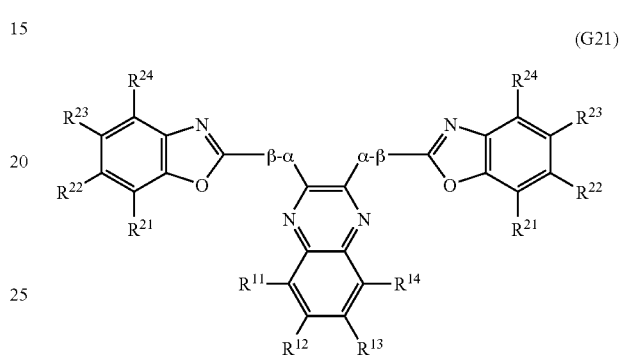

(G21)

In the formula, α represents a substituted or unsubstituted arylene group having 6 to 13 carbon atoms; β represents a substituted or unsubstituted arylene group having 6 to 13 carbon atoms; $R^{21}$ to $R^{24}$ may be the same or different from each other and each represent hydrogen or an alkyl group having 1 to 4 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

Another aspect of the present invention is a quinoxaline derivative represented by a general formula (G22).

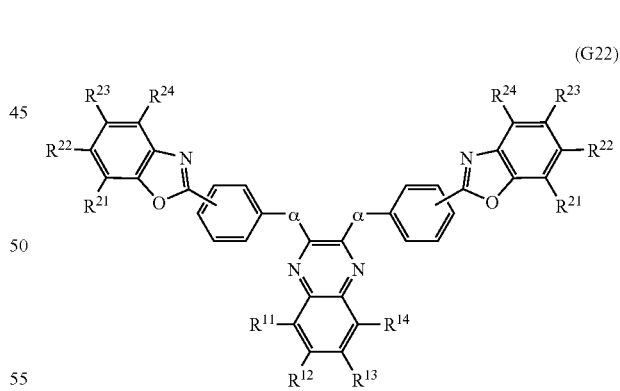

(G22)

In the formula, α represents a substituted or unsubstituted arylene group having 6 to 13 carbon atoms; $R^{21}$ to $R^{24}$ may be the same or different from each other and each represent hydrogen or an alkyl group having 1 to 4 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

Another aspect of the present invention is a quinoxaline derivative represented by a general formula (G23).

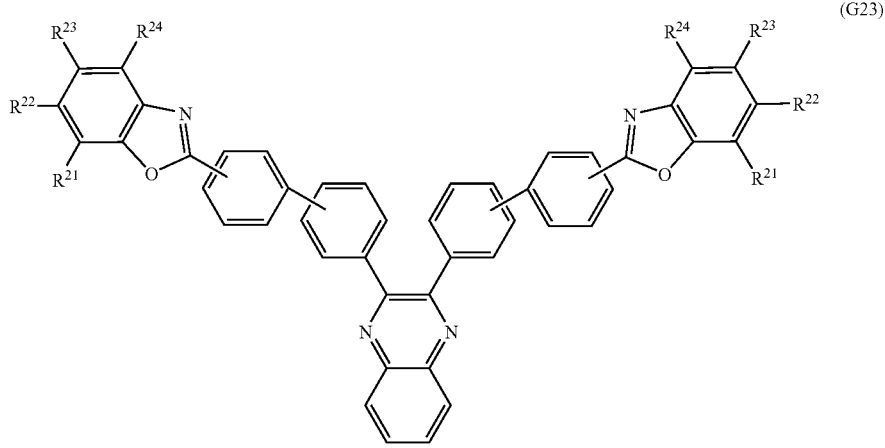

(G23)

In the formula, $R^{21}$ to $R^{24}$ may be the same or different from each other and each represent hydrogen or an alkyl group having 1 to 4 carbon atoms.

Another aspect of the present invention is a quinoxaline derivative represented by a general formula (G24).

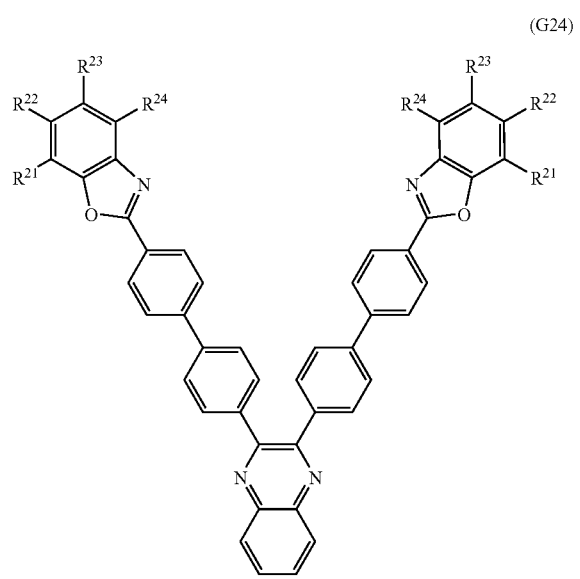

(G24)

In the formula, $R^{21}$ to $R^{24}$ may be the same or different from each other and each represent hydrogen or an alkyl group having 1 to 4 carbon atoms.

In addition, the above-described quinoxaline derivative can be used preferably for a light-emitting element.

Another aspect of the present invention is a light-emitting element including the quinoxaline derivative between a pair of electrodes.

Further, another aspect of the present invention is a light-emitting element having a light-emitting layer and a layer including any of the quinoxaline derivatives described above between an anode and a cathode, in which the layer including the quinoxaline derivative is provided between the light-emitting layer and the cathode.

In that case, the quinoxaline derivatives described above are superior in an electron transporting property; thus, it is preferable that the quinoxaline derivative be particularly used as an electron transporting layer.

In addition, a light-emitting device including the above-described light-emitting element is also within the present invention.

Therefore, another aspect of the present invention is a light-emitting element including the quinoxaline derivatives described above and a control circuit which controls light emission from the light-emitting element.

Note that a light-emitting device in this specification includes an image display device, a light-emitting device, and a light source (including a lighting device). In addition, the light-emitting device includes all of the following modules: modules in which a connector such as an FPC (flexible printed circuit), a TAB (tape automated bonding) tape, or a TCP (tape carrier package) is attached to a panel in which a light-emitting element is formed; modules having a TAB tape or a TCP provided with a printed wiring board at the end thereof; and modules having an IC (integrated circuit) directly mounted on a light-emitting device by a COG (chip on glass) method.

Further, an electronic device using the light-emitting element of the present invention in a display portion is also included in the scope of the present invention. Accordingly, an aspect of the present invention is an electronic device having a display portion, where the display portion includes the above-described light-emitting element and a control circuit configured to control light emission from the light-emitting element.

A quinoxaline derivative of the present invention is superior in an electron transporting property; thus, the quinoxaline derivative is suitably used for a light-emitting element. In addition, by using a quinoxaline derivative of the present invention for a light-emitting element, a light-emitting element with low driving voltage can be obtained. In addition, a light-emitting element with less power consumption can be obtained.

Further, by applying a light-emitting element of the present invention to a light-emitting device and an electronic device, a light-emitting device and an electronic device each having less power consumption can be obtained.

BRIEF DESCRIPTION OF THE DRAWINGS

FIG. 4A is a top view illustrating a light-emitting device according to an aspect of the present invention and FIG. 4B is a cross-sectional view thereof.

DETAILED DESCRIPTION OF THE INVENTION

Figure 1:
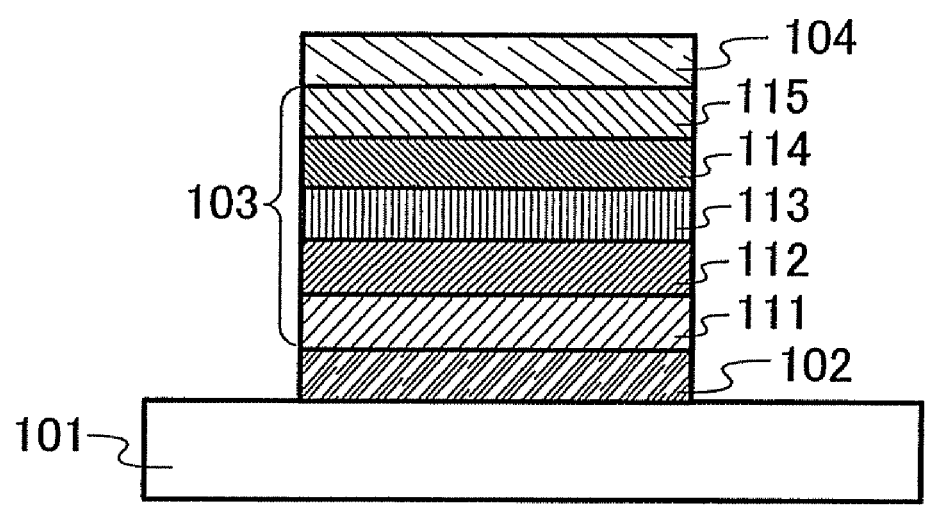
FIG. 1 illustrates a light-emitting element according to an aspect of the present invention.

The embodiment modes according to the present invention will hereinafter be described in detail with reference to the drawings. However, the present invention is not limited to the following description, and it is easily understood by those skilled in the art that the mode and detail can be variously changed without departing from the scope and spirit of the present invention. Therefore, the present invention is not interpreted as being limited to the following description of the embodiment modes.

Embodiment Mode 1

In this embodiment mode, a quinoxaline derivative of the present invention will be described.

A quinoxaline derivative of the present invention has a structure in which at least one of carbon at a 2-position and carbon at a 3-position of quinoxaline, and carbon at a 2-position of benzoxazole are bound via an arylene group so that a quinoxaline derivative which is superior in an electron transporting property can be obtained.

Specifically, a quinoxaline derivative of the present invention is broadly divided into monosubstituted quinoxaline and disubstituted quinoxaline. That is, a quinoxaline derivative of the present invention can be broadly divided into two mode, i.e., a case of a quinoxaline derivative in which one of carbon at a 2-position and carbon at a 3-position of quinoxaline, and carbon at a 2-position of benzoxazole are bound via an arylene group, and a case of a quinoxaline derivative in which both carbon at a 2-position and carbon at a 3-position of quinoxaline, and carbon at a 2-position of benzoxazole are bound via an arylene group. Further, the former monosubstituted quinoxaline derivative is a quinoxaline derivative represented by a general formula (G11).

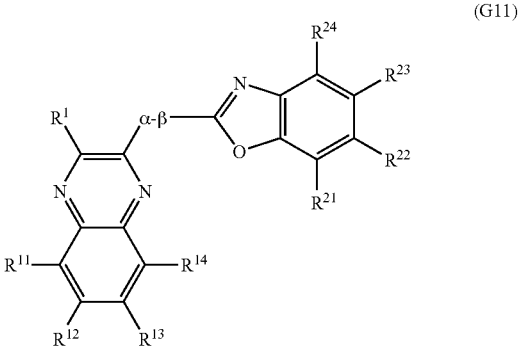

(G11)

In the formula, α represents a substituted or unsubstituted arylene group having 6 to 13 carbon atoms; β represents a substituted or unsubstituted arylene group having 6 to 13 carbon atoms; $R^{21}$ to $R^{24}$ may be the same or different from each other and each represent hydrogen or an alkyl group having 1 to 4 carbon atoms; $R^1$ represents an alkyl group having 1 to 4 carbon atoms or a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms. Further, the number of substituents of an aryl group may be either one or more than one, more than one substituent may be bound to each other to form a ring, and a ring structure may be spiro ring.

On the other hand, the latter disubstituted quinoxaline derivative is a quinoxaline derivative represented by a general formula (G21).

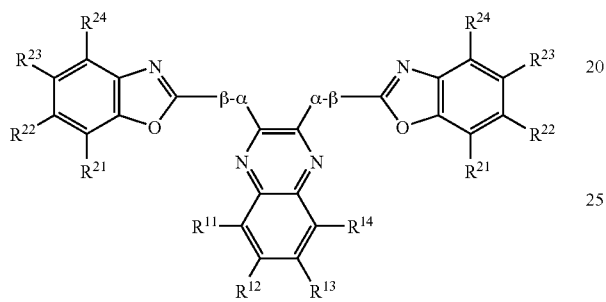

(G21)

In the formula, α represents a substituted or unsubstituted arylene group having 6 to 13 carbon atoms; β represents a substituted or unsubstituted arylene group having 6 to 13 carbon atoms; $R^{21}$ to $R^{24}$ may be the same or different from each other and each represent hydrogen or an alkyl group having 1 to 4 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

A quinoxaline derivative represented by the general formula (G21) has a structure in which carbon at a 2-position and carbon at a 3-position of quinoxaline, and carbon at a 2-position of benzoxazole are bound via an arylene group. Thus, the molecular weight of the quinoxaline derivative represented by the general formula (G21) is larger than that of a quinoxaline derivative represented by the general formula (G11), and a thermophysical property of the monosubstituted quinoxaline derivative represented by the general formula (G21) is higher. In addition, since the thermophysical property is higher, improvement in stability of a film quality (crystallization can be suppressed) is expected. Further, in the general formulae (G11) and (G21), as a substituent represented by α, for example, an arylene group represented by structural formulae (12-1) to (12-10) can be given. As shown in structural formulae (12-4), (12-8) to (12-10), and the like, an arylene group represented by α may include a substituent.

Note that the carbon atoms of an aryl group or an arylene group shown in this specification represent carbon atoms which form a ring of the main skeleton, and carbon atoms of a substituent bound thereto are not included therein. Note that the number of substituents of an aryl group or an arylene group may be either one or more than one. In particular, more than one substituent may be bound to each other to form a ring. For example, in a case where an arylene group is a fluorene-diyl group, carbon at a 9-position may include two phenyl groups, and the two phenyl groups may be bound to each other to form a spiro ring structure. The structural formula (12-9) is an example in which a spiro ring structure is formed.

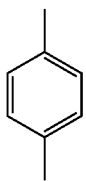

(12-1)

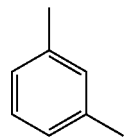

(12-2)

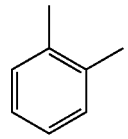

(12-3)

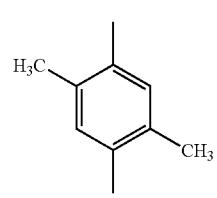

(12-4)

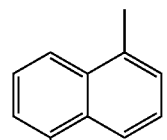

(12-5)

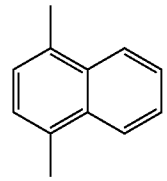

(12-6)

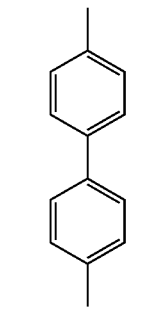

(12-7)

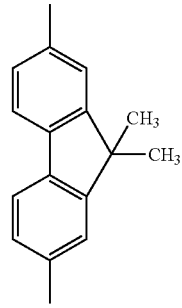

(12-8)

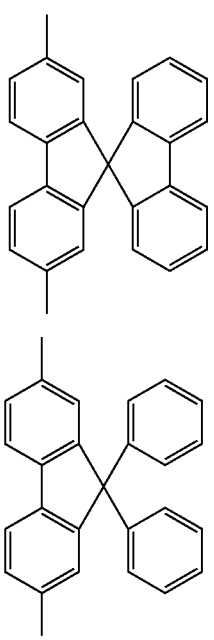

Further, in the general formulae (G11) and (G21), as a substituent represented by β, for example, an arylene group represented by structural formulae (13-1) to (13-10) can be given. As shown in the structural formulae (13-4), (13-8) to (13-10), and the like, an arylene group represented by β may include a substituent.

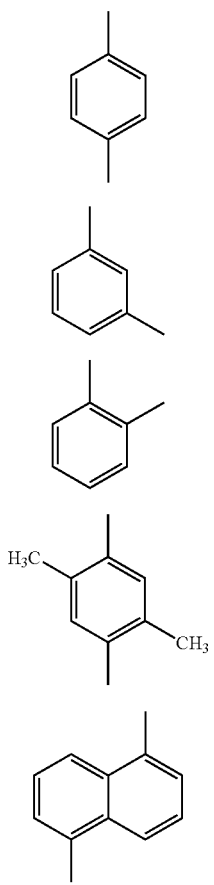

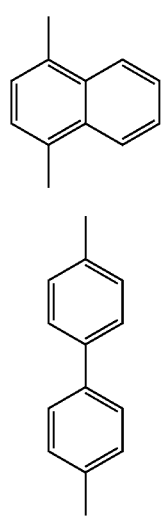

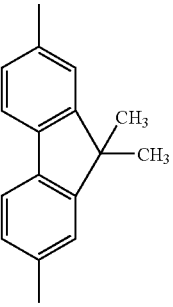

Further, in the general formulae (G11) and (G21), as substituents represented by $R^{11}$ to $R^{14}$, for example, hydrogen, an alkyl group or an aryl group, which are represented by structural formulae (14-1) to (14-22), or the like can be given. As shown in the structural formulae (14-16) to (14-22) and the like, an aryl group represented by $R^{11}$ to $R^{14}$ may each include a substituent.

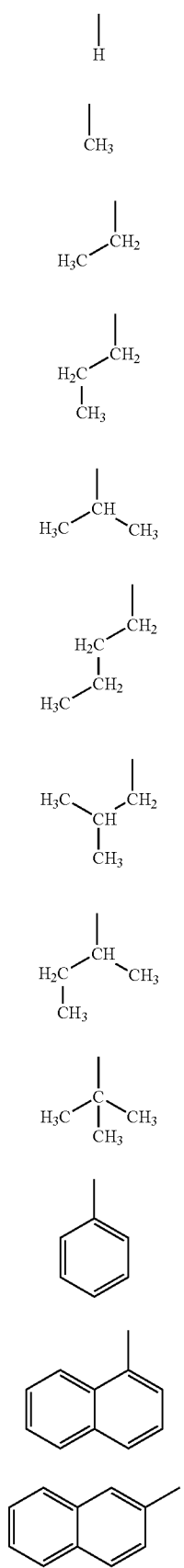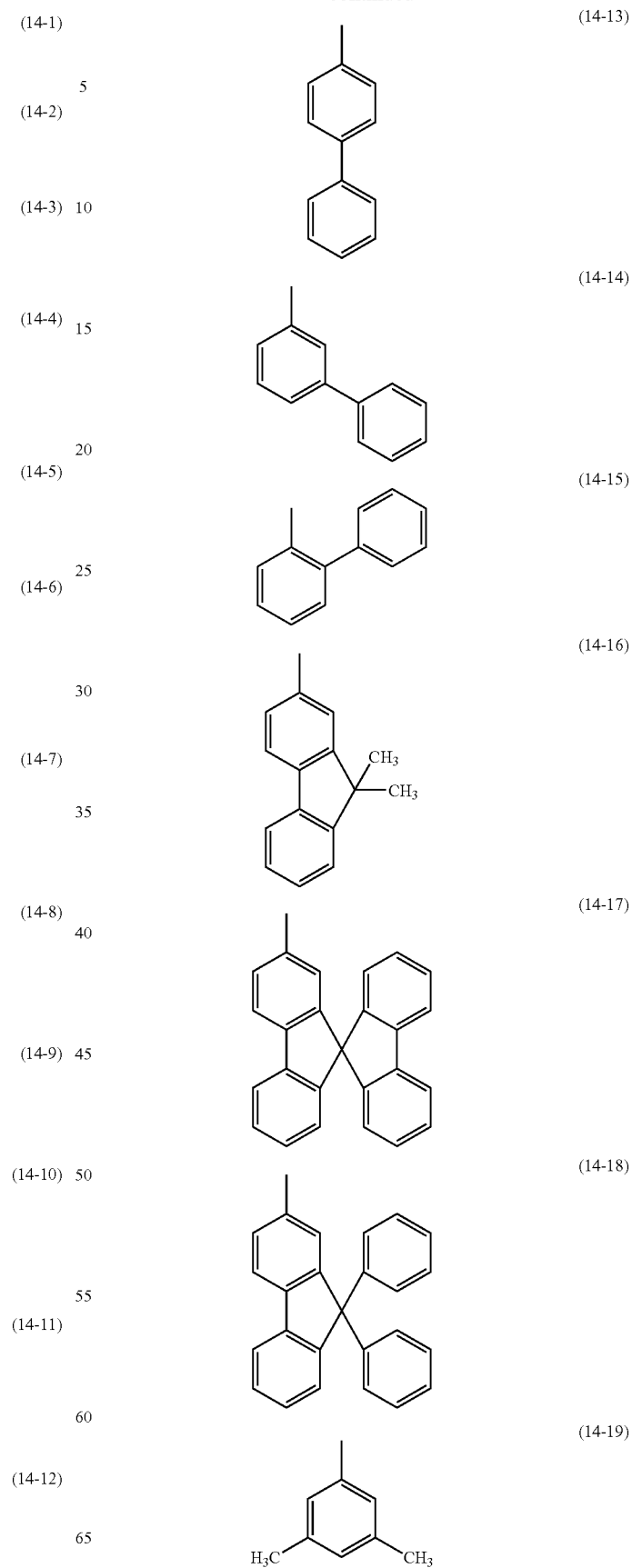

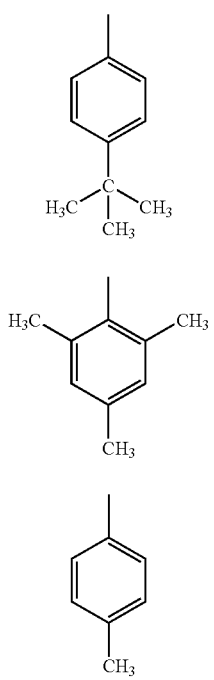

Further, in the general formulae (G11) and (G21), as substituents represented by $R^{21}$ to $R^{24}$, for example, hydrogen or an alkyl group, which are represented by structural formulae (15-1) to (15-9), or the like can be given.

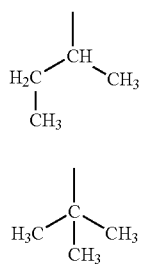

In addition, in the general formula (G11), as a substituent represented by $R^1$, for example, an alkyl group or an aryl group represented by structural formulae (16-1) to (16-21) can be given. As shown in the structural formulae (16-15) to (16-21) and the like, an aryl group represented by $R^1$ may include a substituent.

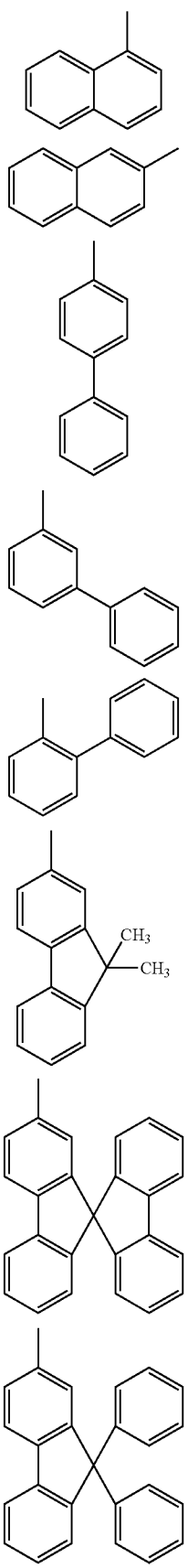
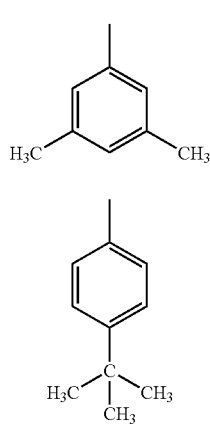
In a quinoxaline derivative represented by the general formula (G11), β is preferably a phenylene group for ease of synthesis. That is, the quinoxaline derivative represented by the general formula (G12) is preferable.
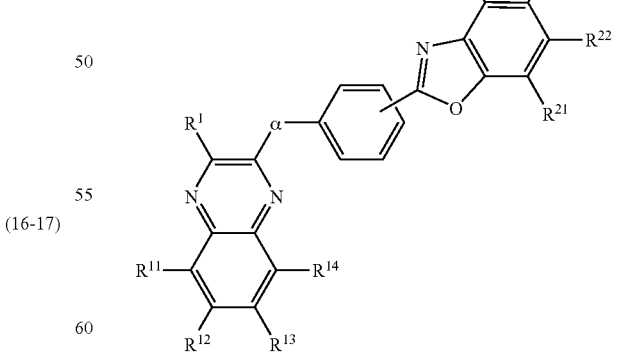
In the formula, α represents a substituted or unsubstituted arylene group having 6 to 13 carbon atoms; $R^{21}$ to $R^{24}$ may be the same or different from each other and each represent hydrogen or an alkyl group having 1 to 4 carbon atoms; $R^1$ represents an alkyl group having 1 to 4 carbon atoms, or a substituted or unsubstituted aryl group having 6 to 13 carbon atoms; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

Similarly, in a quinoxaline derivative represented by the general formula (G21), β is preferably a phenylene group for ease of synthesis. That is, a quinoxaline derivative represented by the general formula (G22) is preferable.

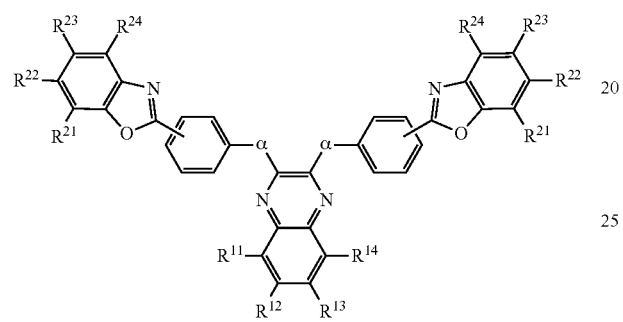

(G22)

In the formula, α represents a substituted or unsubstituted arylene group having 6 to 13 carbon atoms; $R^{21}$ to $R^{24}$ may be the same or different from each other and each represent hydrogen or an alkyl group having 1 to 4 carbon atoms;; and $R^{11}$ to $R^{14}$ may be the same or different from each other and each represent any of hydrogen, an alkyl group having 1 to 4 carbon atoms, or a substituted or unsubstituted aryl group having 6 to 13 carbon atoms.

More preferably, in a quinoxaline derivative represented by the general formula (G11), α is preferably a phenylene group for ease of synthesis and purification (purity improvement).

In that case, a bonding relationship between two phenylene groups may be any of an ortho position, a meta position, or a para position. Further, $R^{11}$ to $R^{14}$ are preferably hydrogen for ease of synthesis and purification (purity improvement). That is, a quinoxaline derivative represented by a general formula (G13) is preferably used.

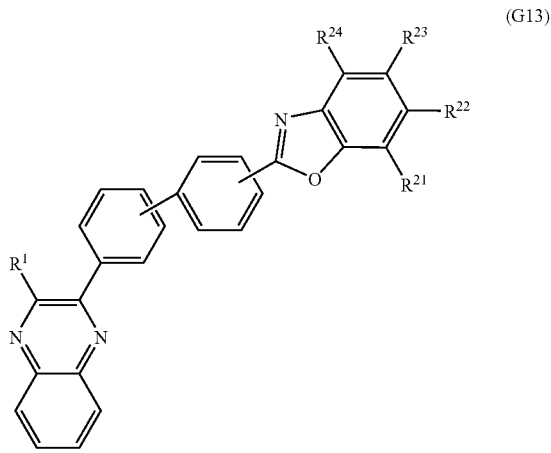

(G13)

In the formula, $R^{21}$ to $R^{24}$ may be the same or different from each other and each represent hydrogen or an alkyl group having 1 to 4 carbon atoms; and $R^1$ represents an alkyl group having 1 to 4 carbon atoms, or a substituted or unsubstituted aryl group having 6 to 13 carbon atoms.

Similarly, in the quinoxaline derivative represented by the general formula (G21), α is preferably a phenylene group for ease of synthesis and purification (improvement in purity). In that case, two phenylene groups may be bound at any of an ortho position, a meta position, or a para position. Further, each of $R^{11}$ to $R^{14}$ is preferably hydrogen for ease of synthesis and purification (improvement in purity). That is, a quinoxaline derivative represented by a general formula (G23) is preferable.

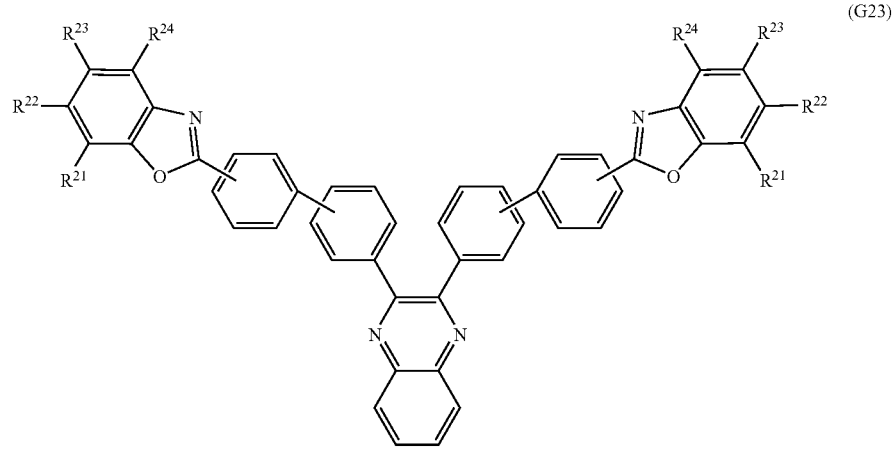

(G23)

In the formula, $R^{21}$ to $R^{24}$ may be the same or different from each other, and each represent hydrogen or an alkyl group having 1 to 4 carbon atoms.

More preferably, in the quinoxaline derivative represented by the general formula (G11), when both α and β are phenylene groups, they are bound at a para position. With such a structure, steric hindrance is reduced, and synthesis becomes easier. That is, the quinoxaline derivative represented by a general formula (G14) is preferable.

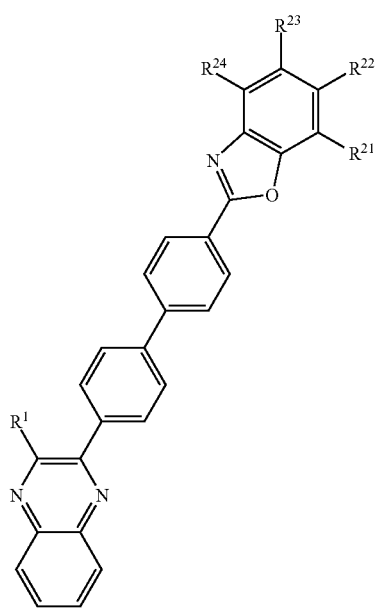

(G14)

In the formula, $R^{21}$ to $R^{24}$ may be the same or different from each other, and each represent hydrogen or an alkyl group having 1 to 4 carbon atoms; and $R^1$ represents any of an alkyl group having 1 to 4 carbon atoms, or a substituted or unsubstituted aryl group having 6 to 13 carbon atoms.

Similarly, in the quinoxaline derivative represented by the general formula (G21), when both α and β are phenylene groups, they are preferable to be bound at a para position. With such a structure, steric hindrance is reduced, and synthesis becomes easier. That is, the quinoxaline derivative represented by a general formula (G24) is preferable.

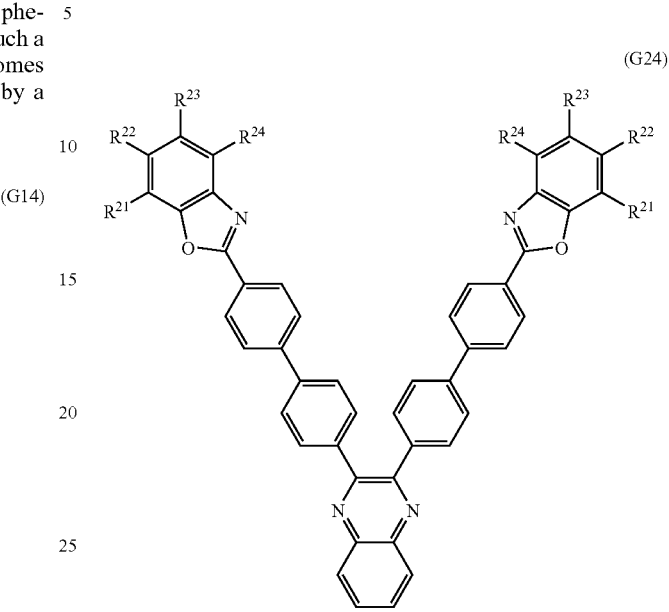

(G24)

In the formula, $R^{21}$ to $R^{24}$ may be the same or different from each other, and each represent hydrogen or an alkyl group having 1 to 4 carbon atoms.

Further, in the quinoxaline derivative represented by the general formula (G11), $R^1$ is preferably a phenyl group or a biphenyl group for ease of synthesis and purification (improvement in purity).

As the quinoxaline derivative represented by the general formula (G11), for example, quinoxaline derivatives represented by structural formulae (101) to (191) can be given. Further, as the quinoxaline derivative represented by the general formula (G21), for example, quinoxaline derivatives represented by structural formulae (201) to (268) can be given. However, the present invention is not limited to the following structural formulae.

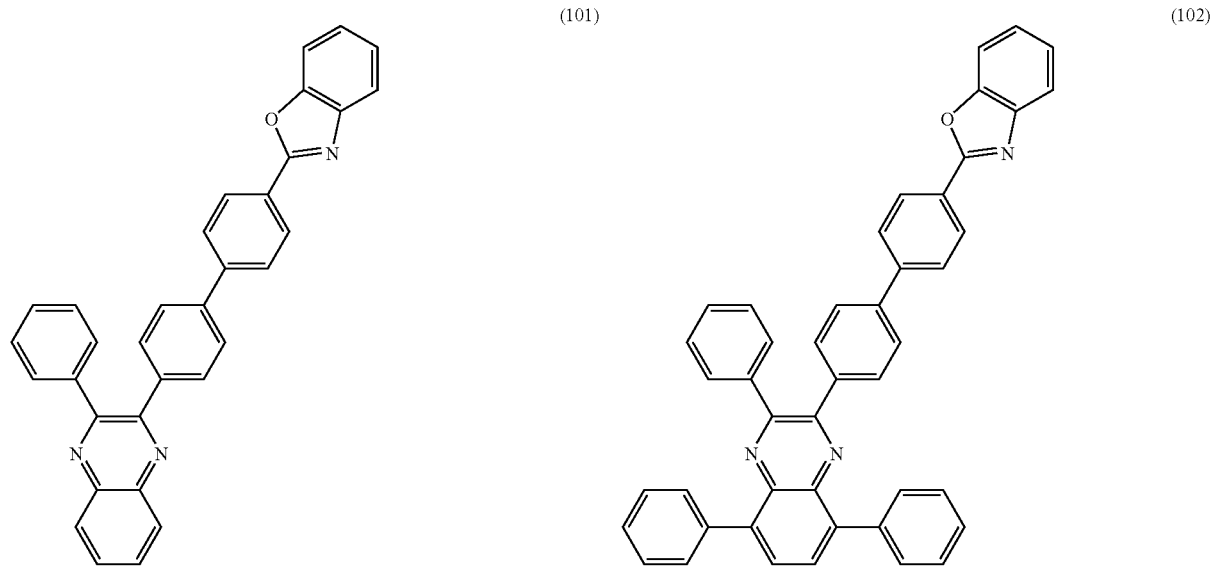

(101)    (102)

(103)
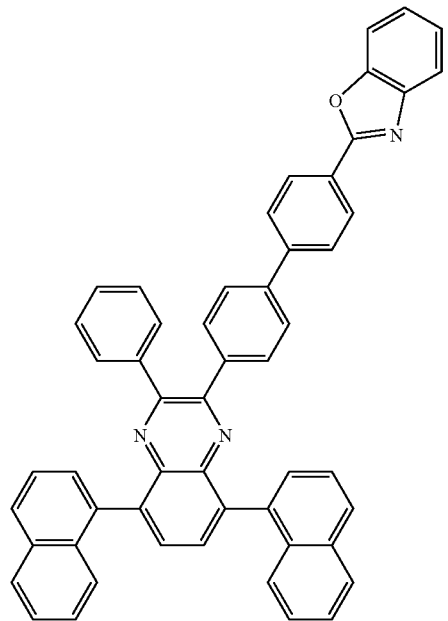
(104)
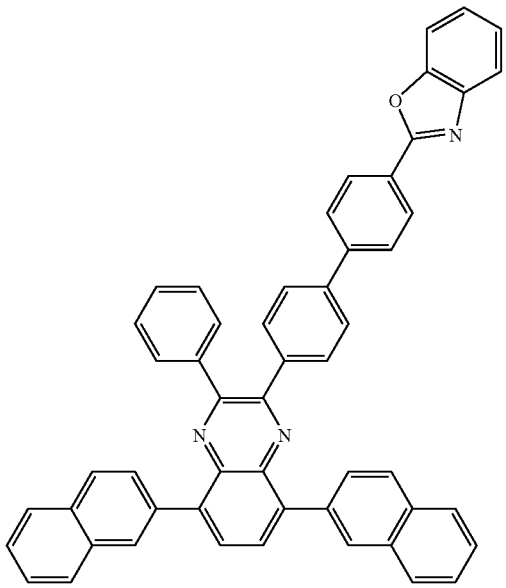
(105)
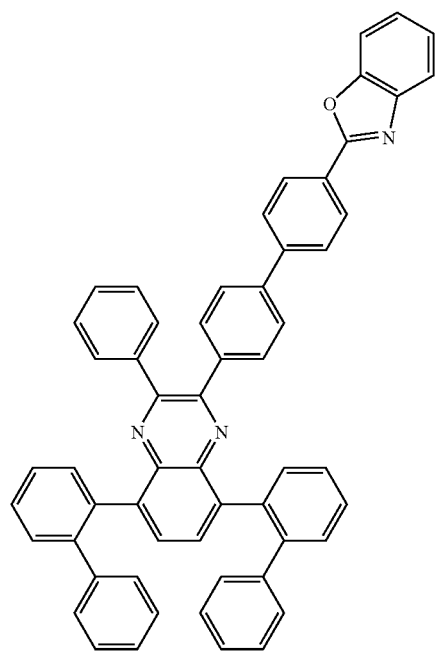
(106)
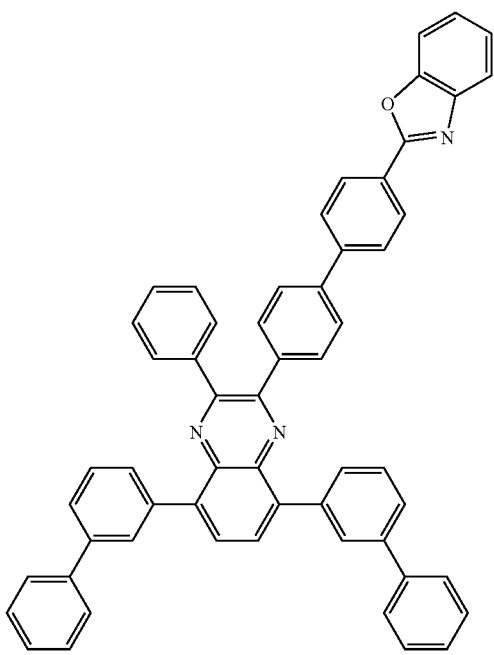

(107)
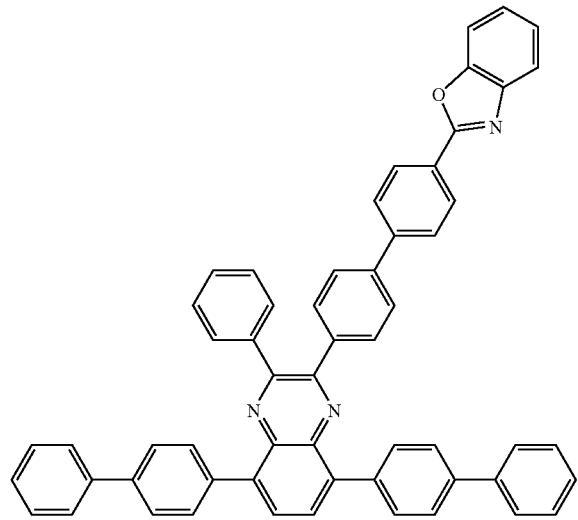
(108)
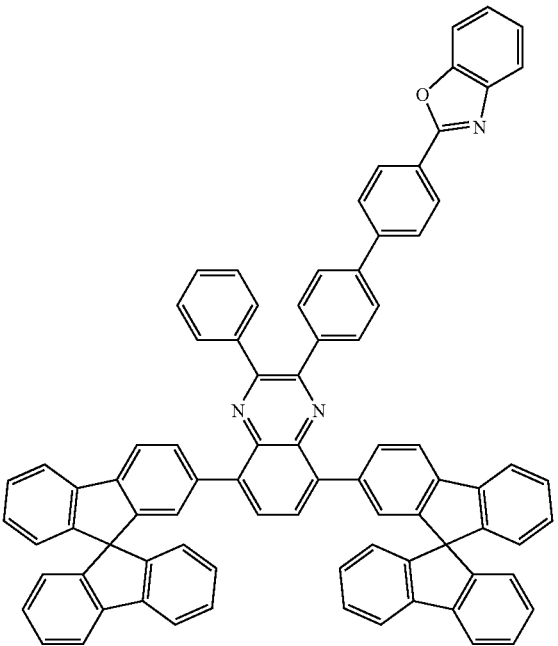
(109)
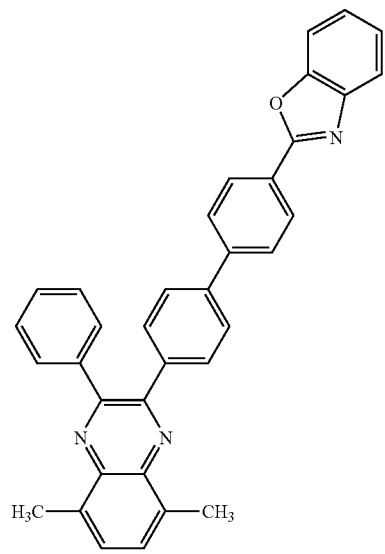
(110)
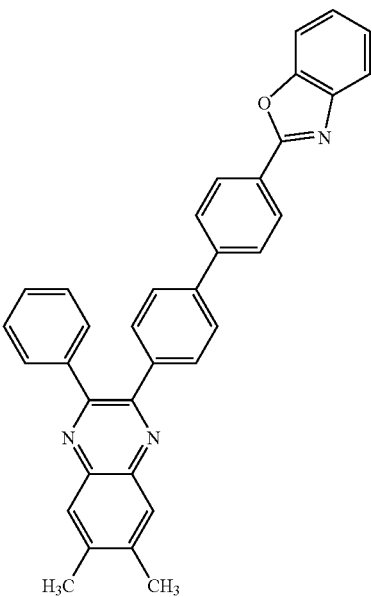

-continued
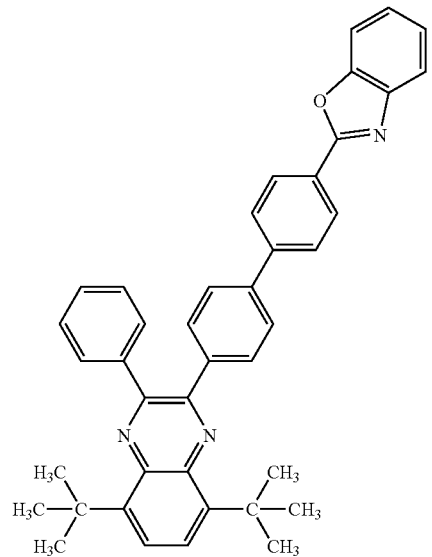
(111)
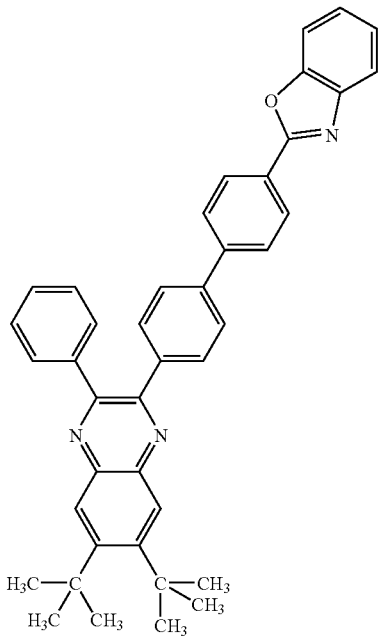
(112)
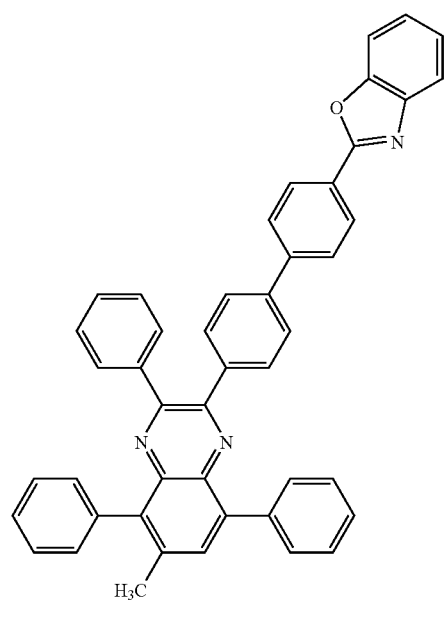
(113)
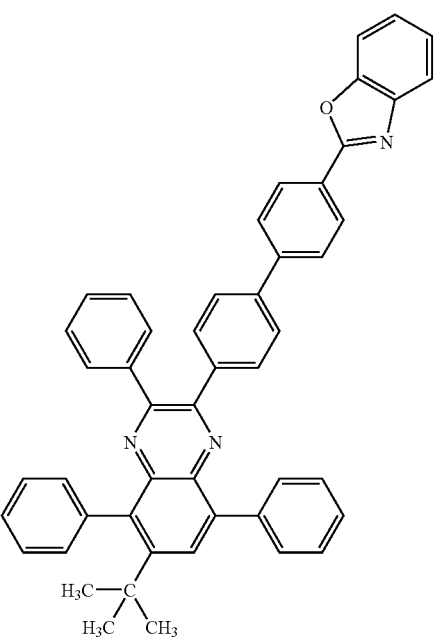
(114)

-continued
(115)
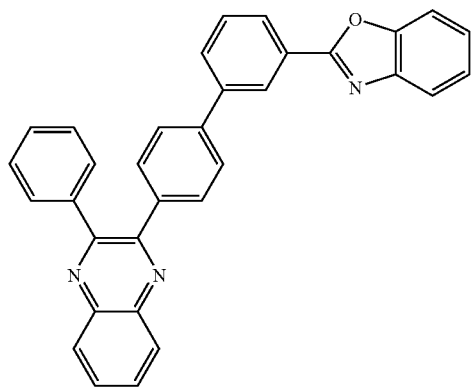
(116)
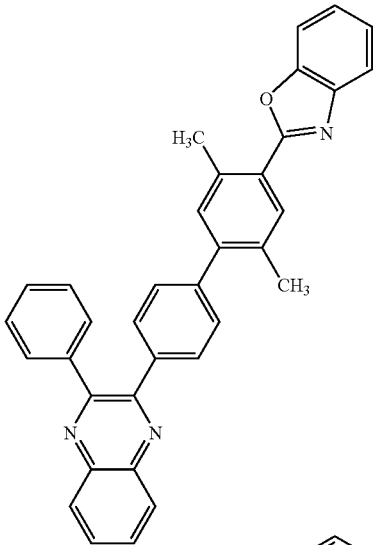
(117)
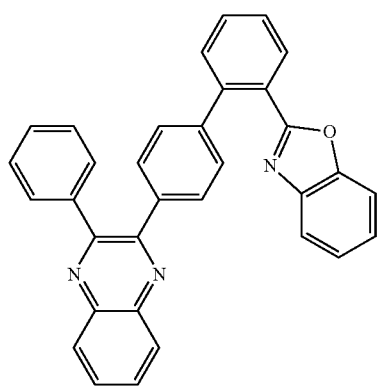
(118)
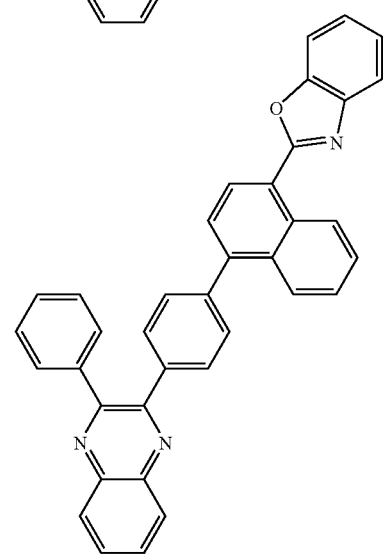
(119)
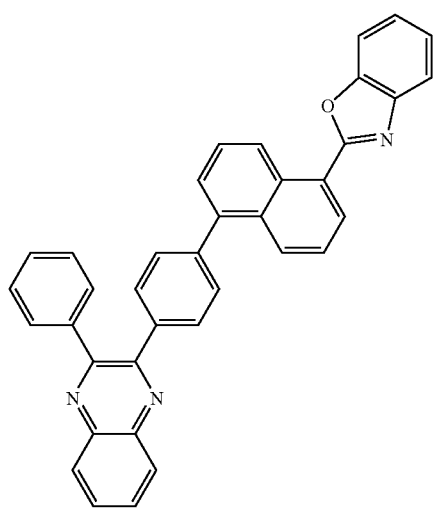
(120)
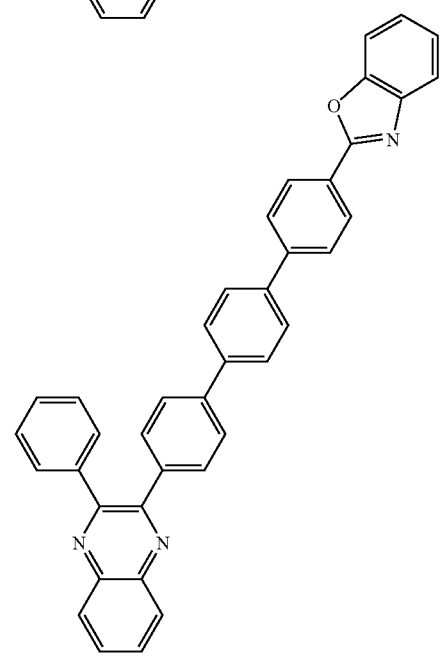

-continued
(121)
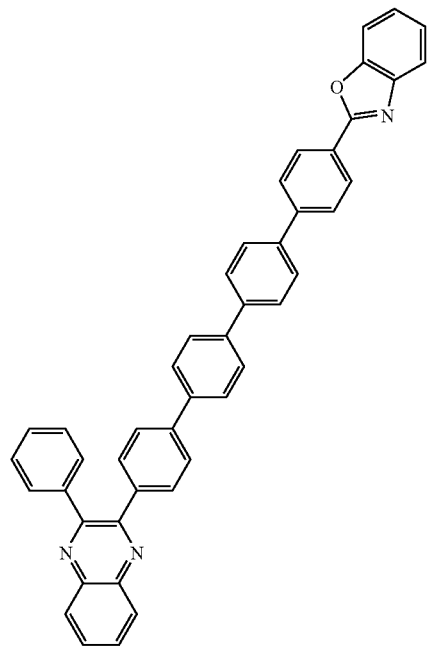
(123)
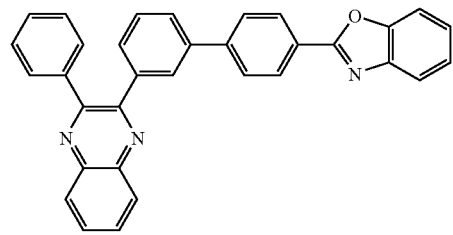
(122)
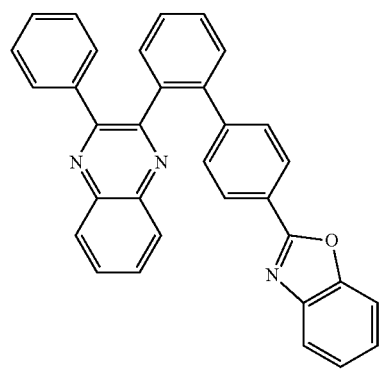
(124)
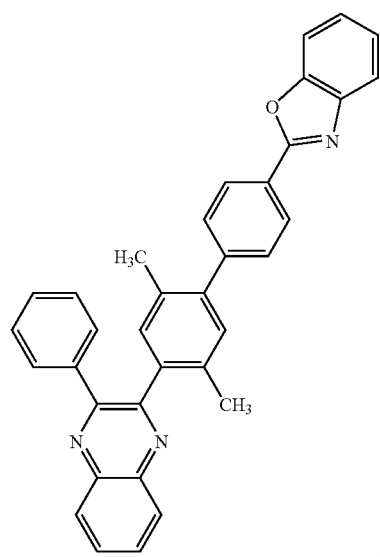
(125)
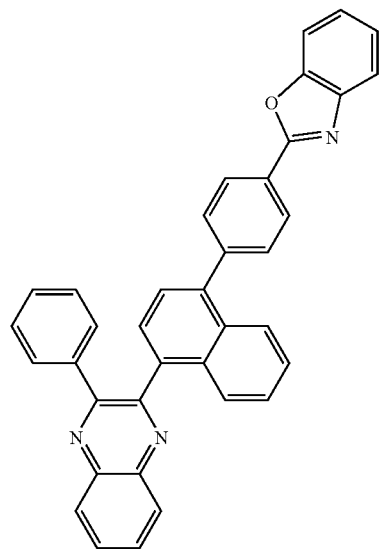
(126)
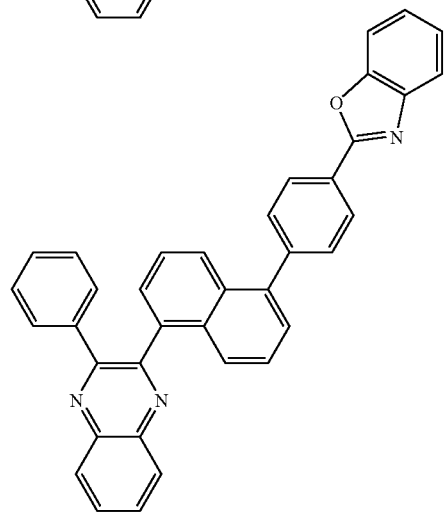

(127)
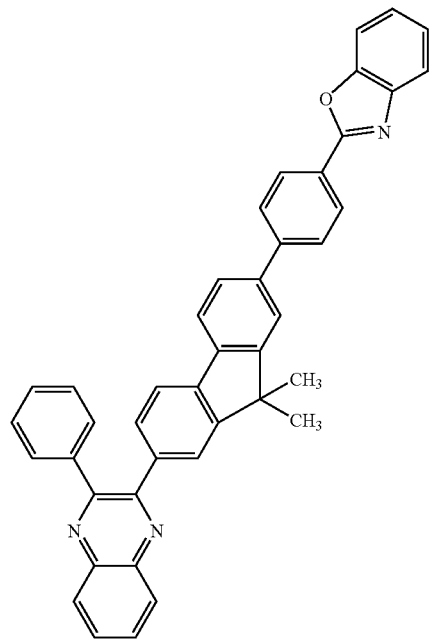
(128)
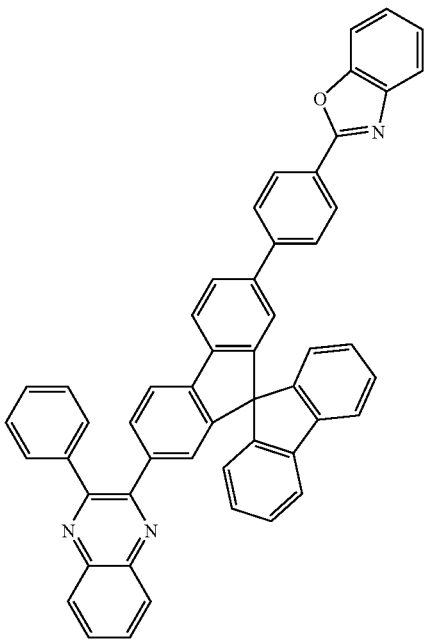
(129)
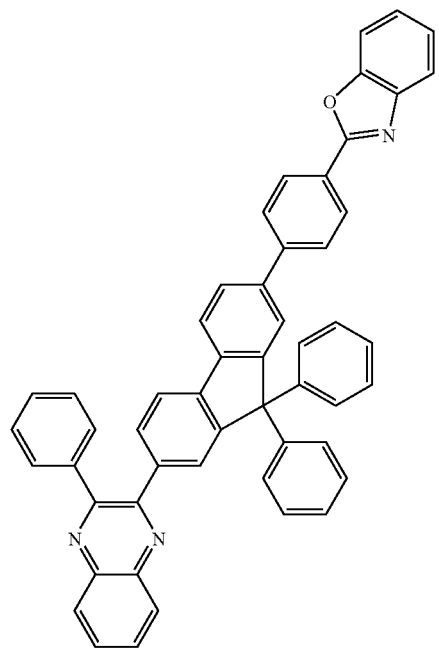
(130)
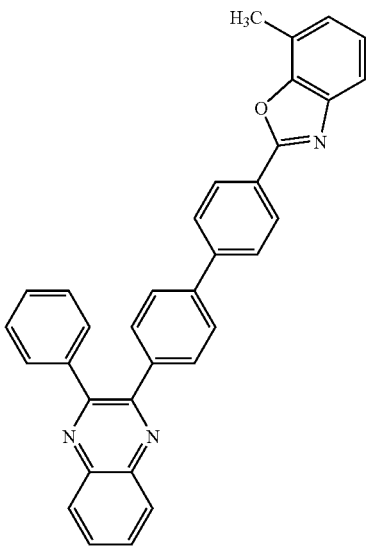

-continued
(131) 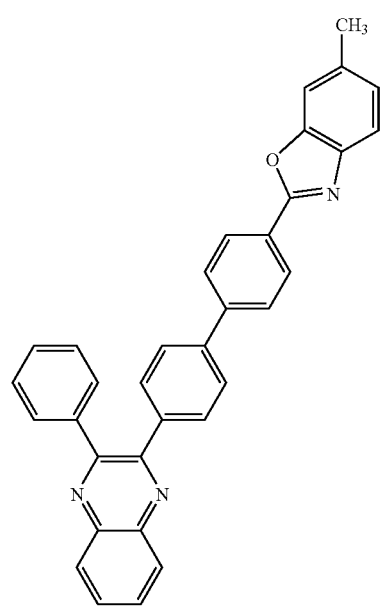
(132) 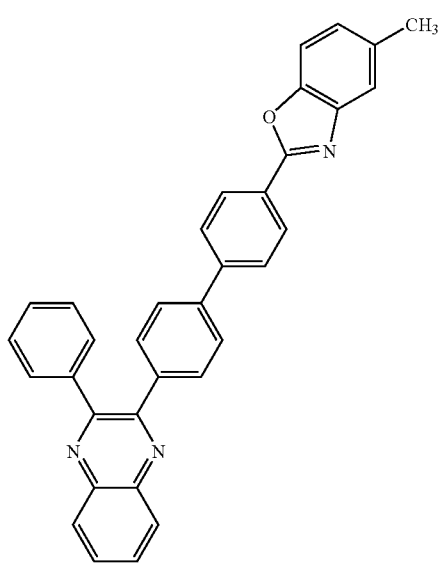
(133) 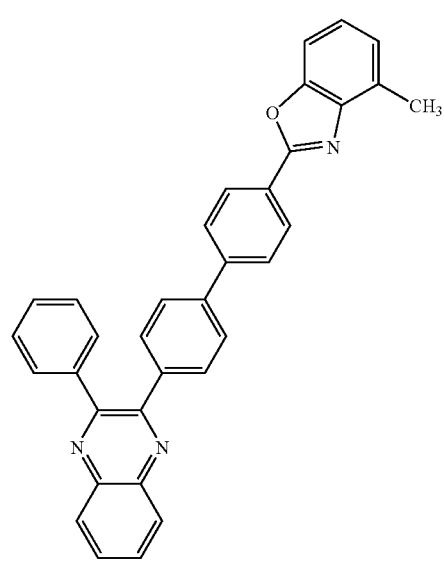
(134) 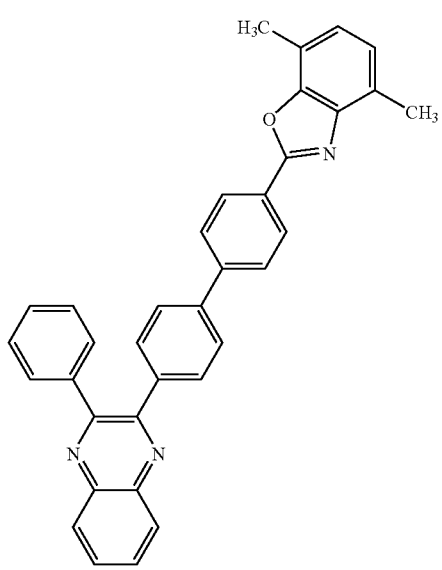

-continued
(135)
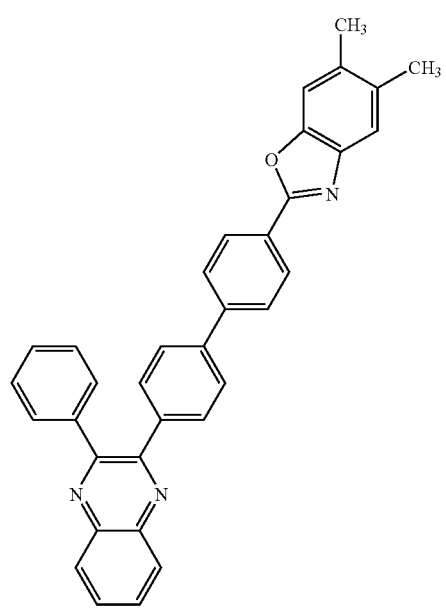
(136)
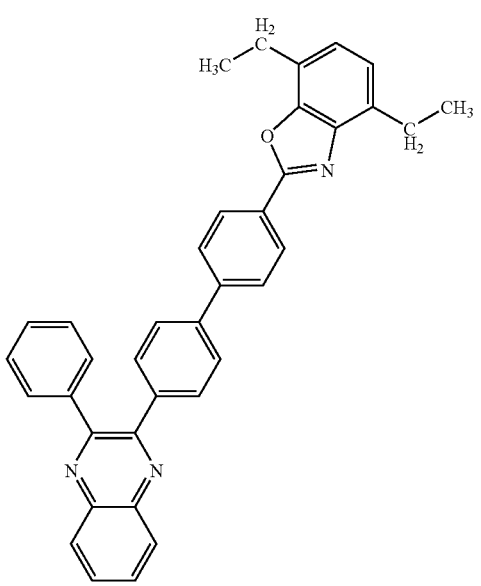
(137)
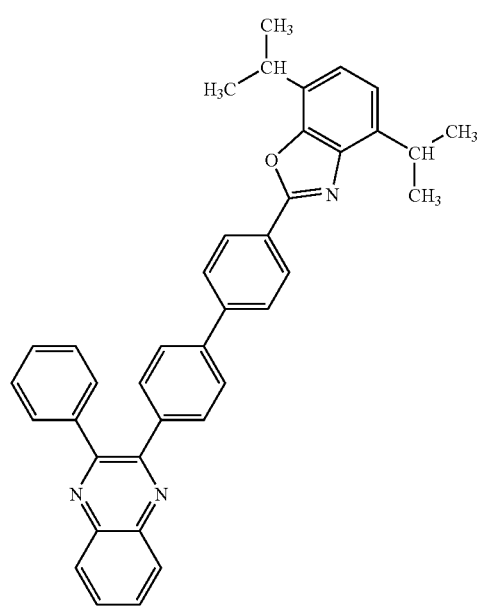
(138)
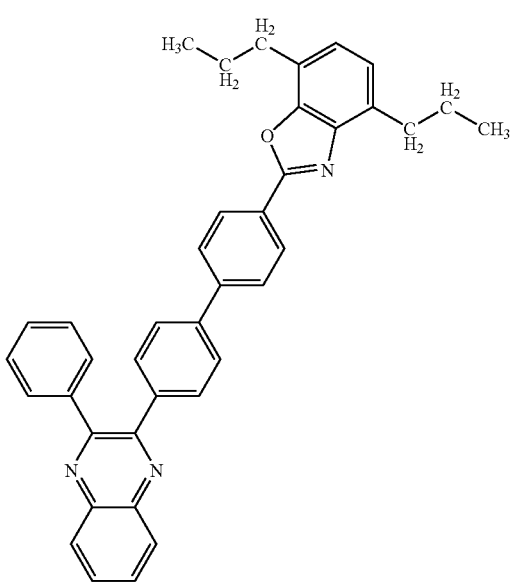

-continued
(139)
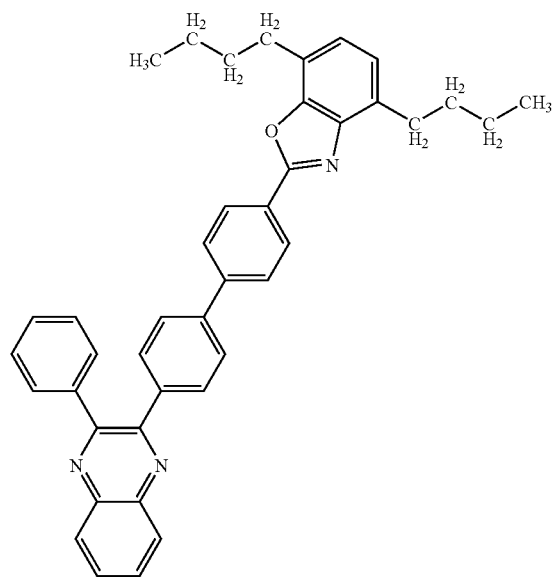
(140)
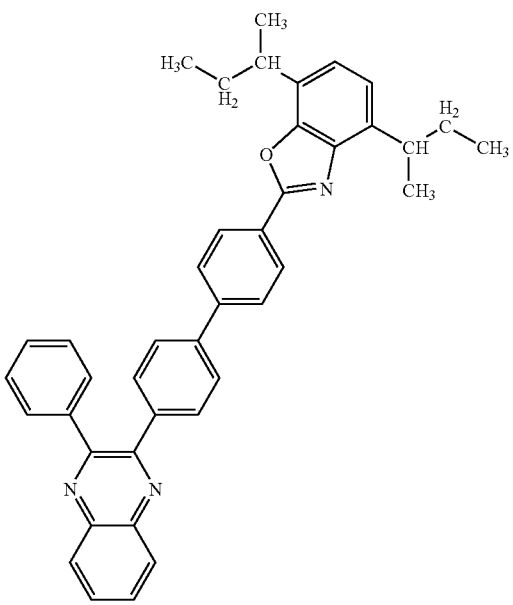
(141)
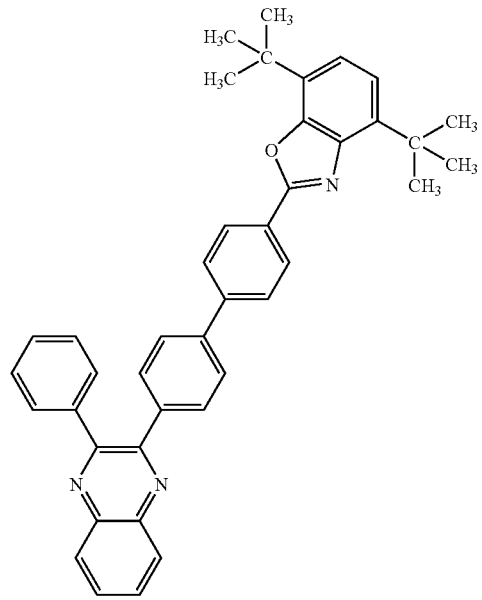
(142)
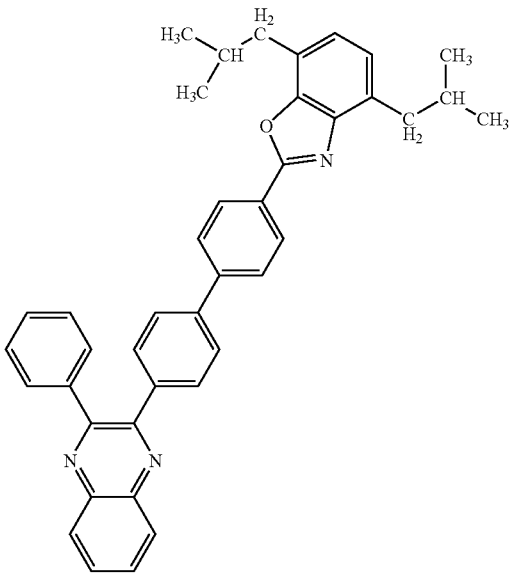

(143)
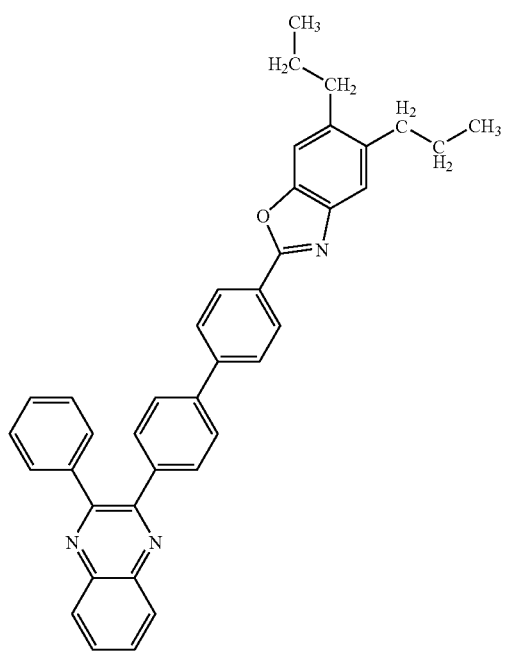
(144)
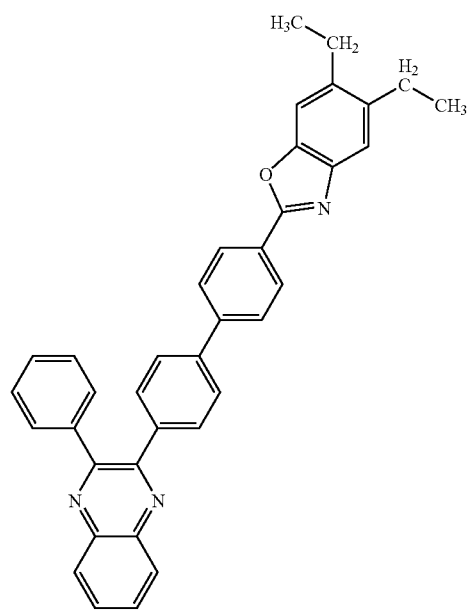
(145)
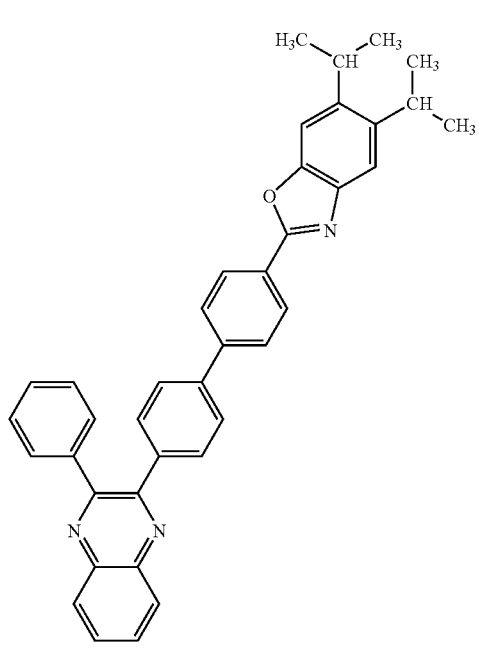
(146)
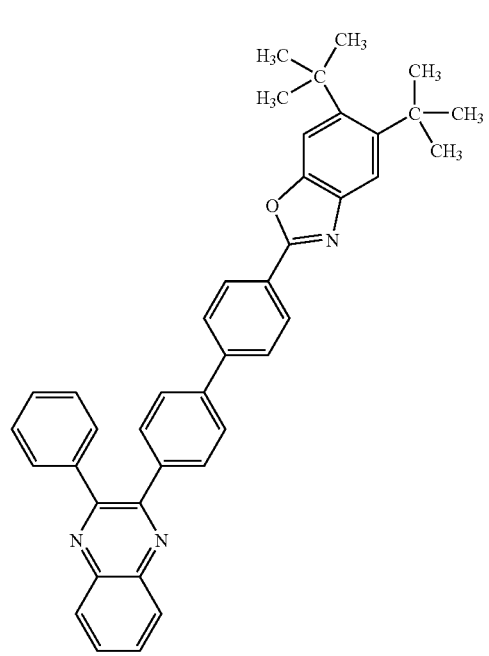

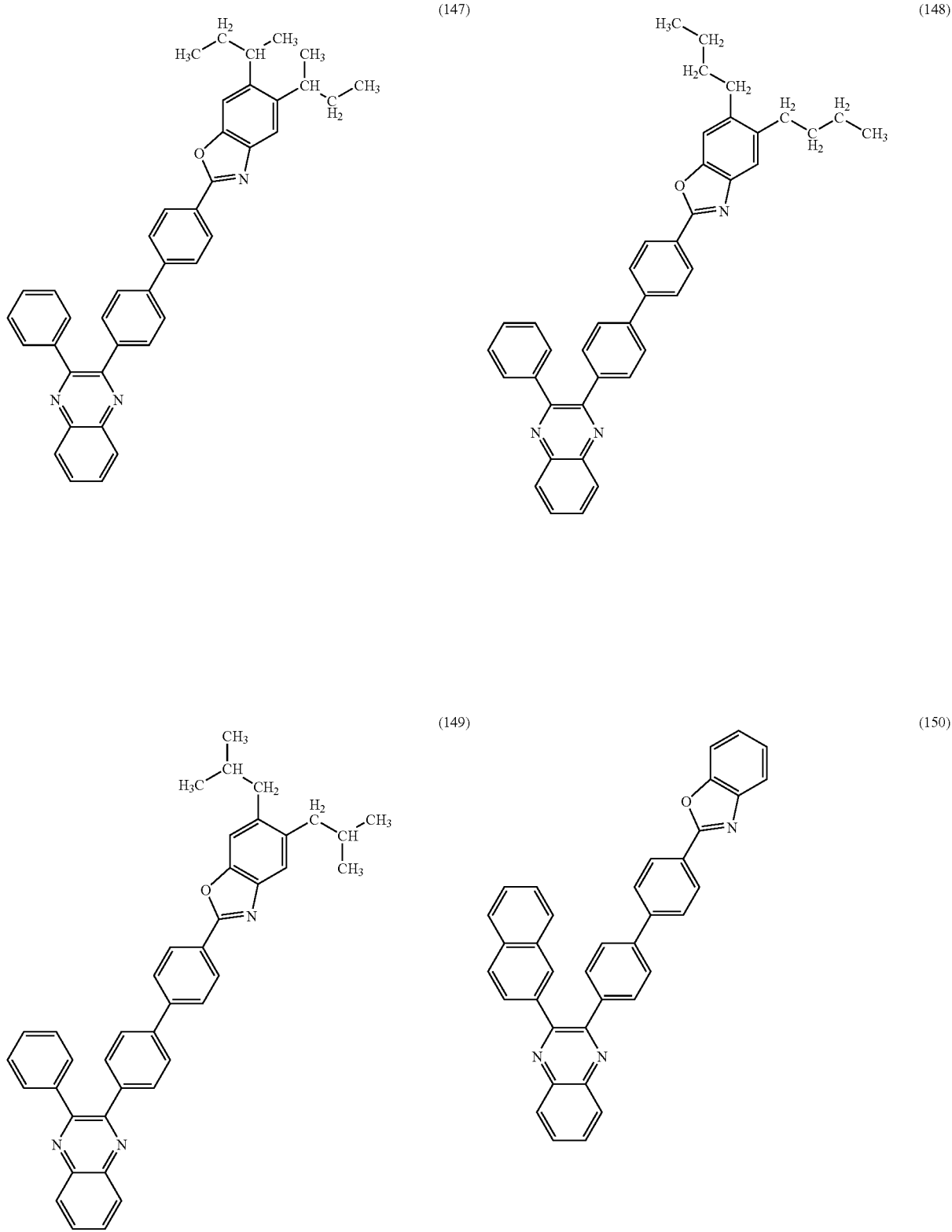

(151)
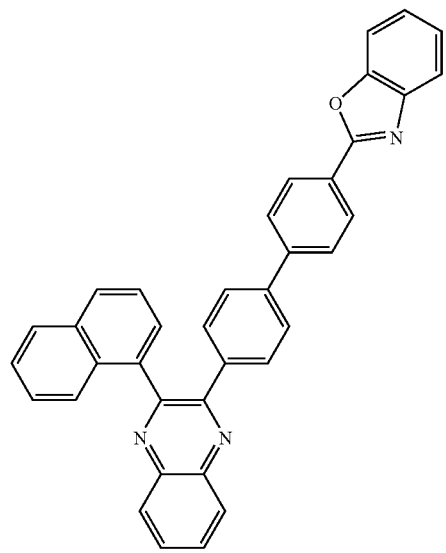
(152)
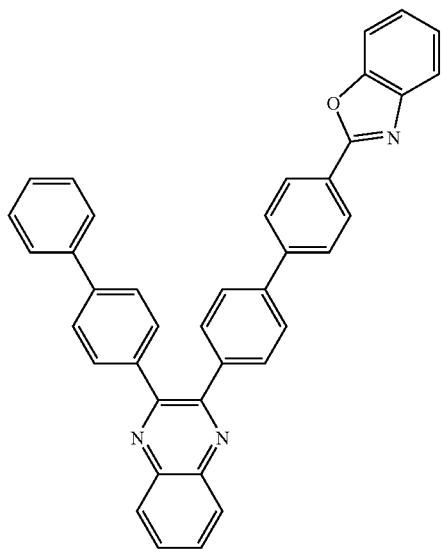
(153)
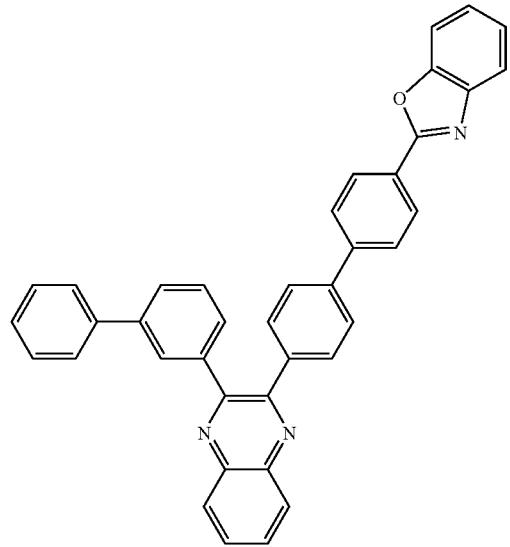
(154)
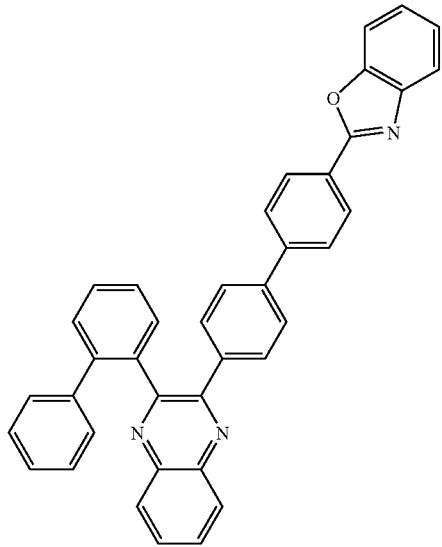
(155)
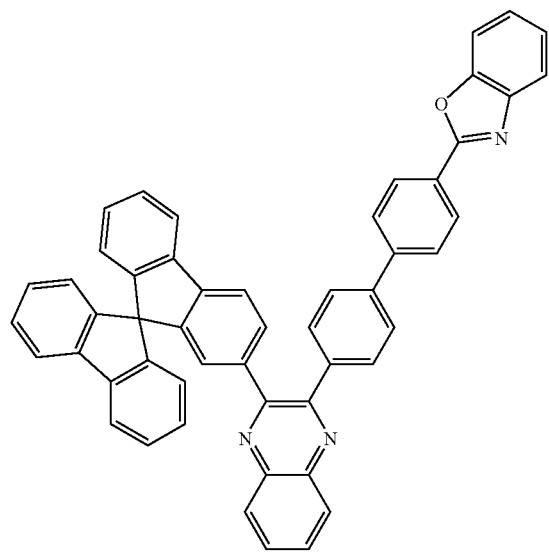
(156)
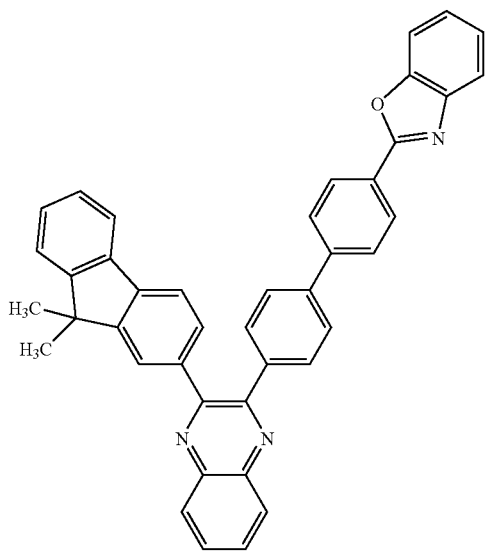

-continued
(157)
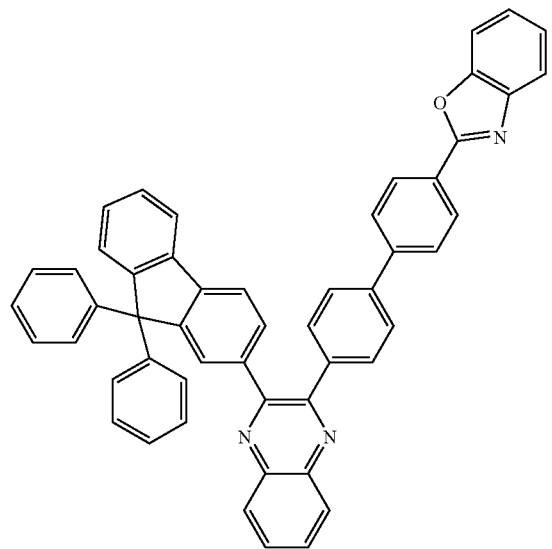
(158)
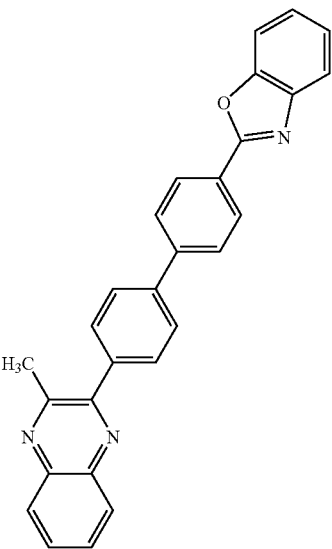
(159)
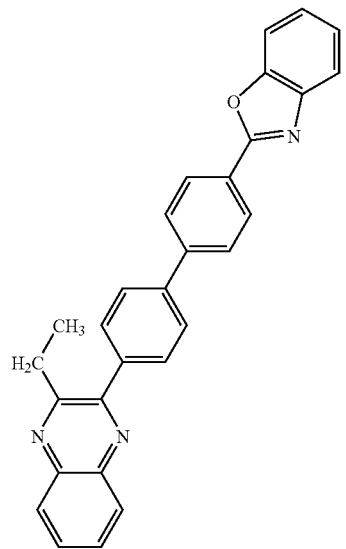
(160)
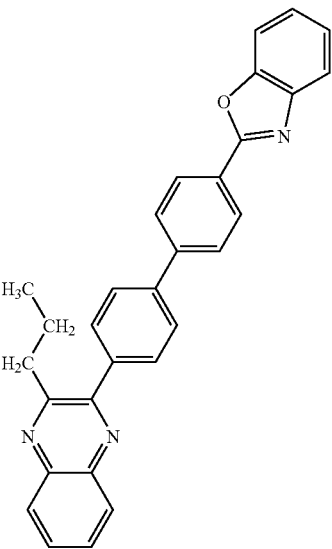
(161)
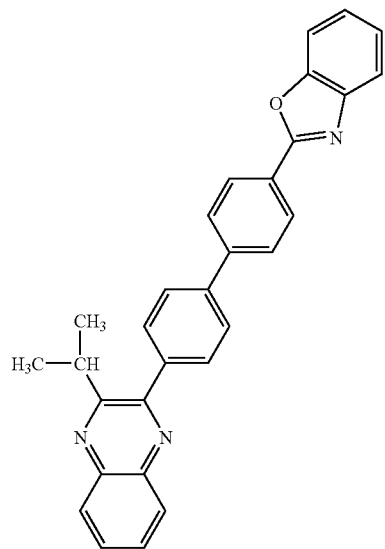
(162)
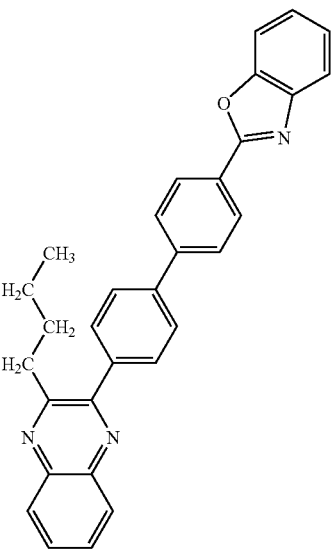

-continued
(163)
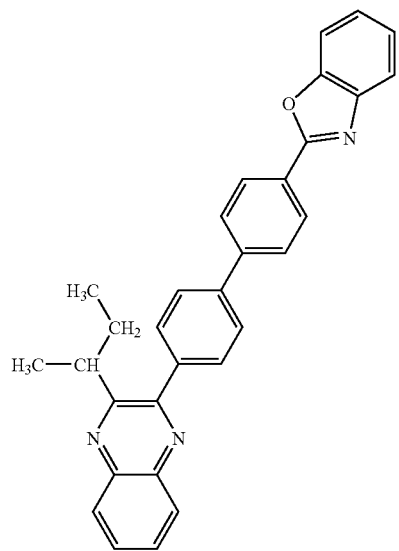
(164)
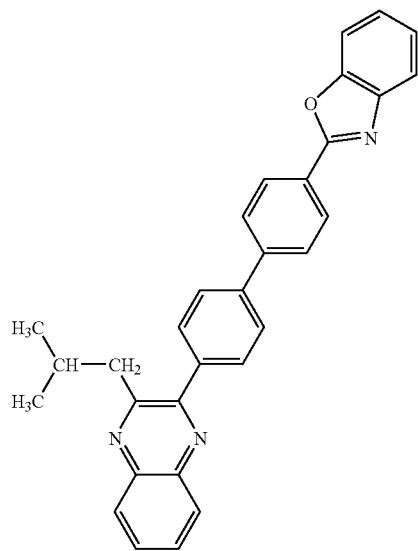
(165)
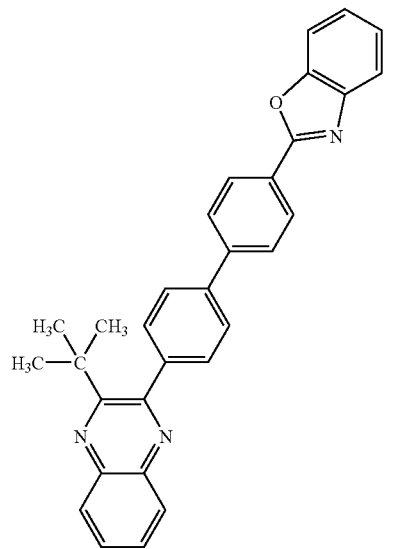
(166)
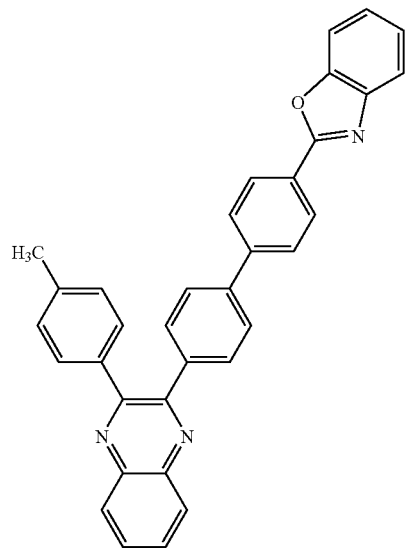
(167)
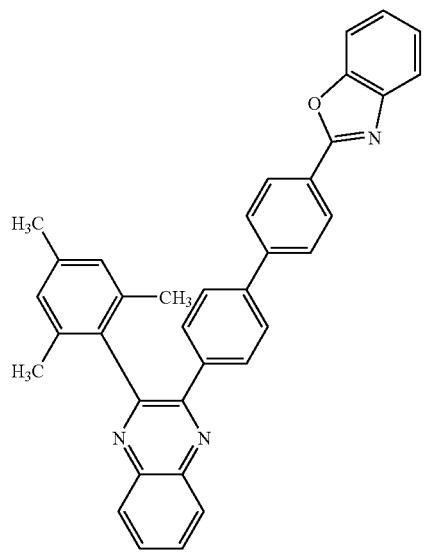
(168)
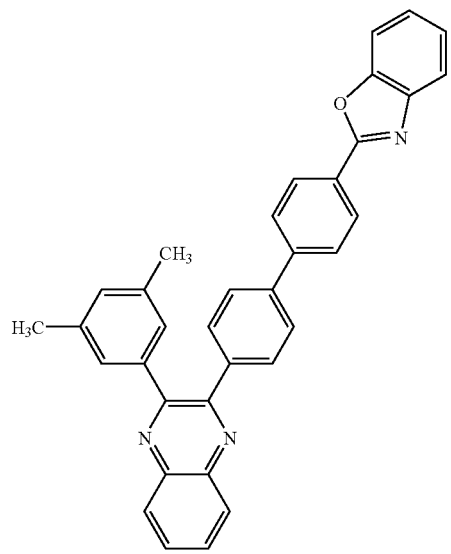

-continued
(169)
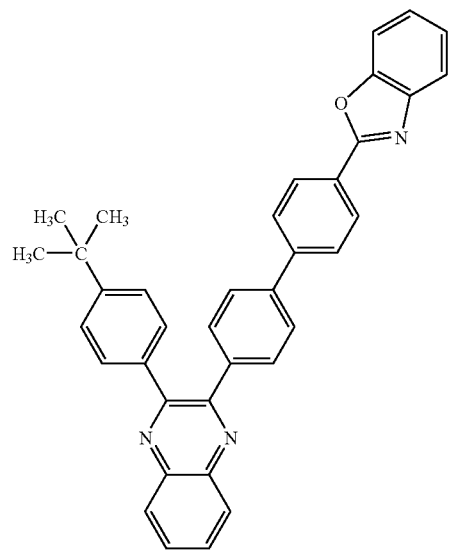
(170)
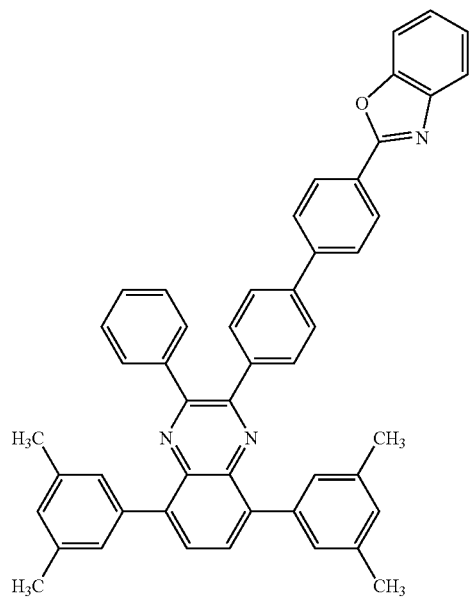
(171)
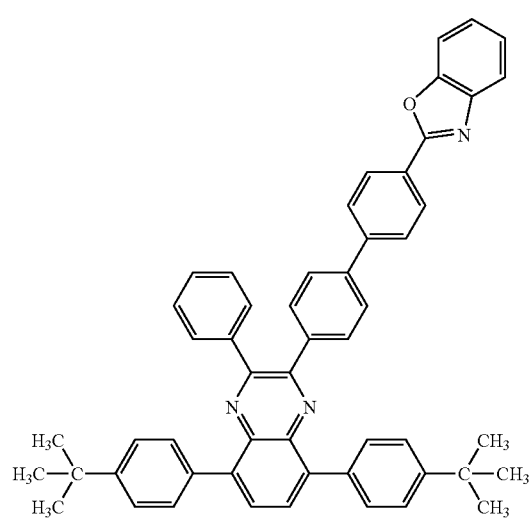
(172)
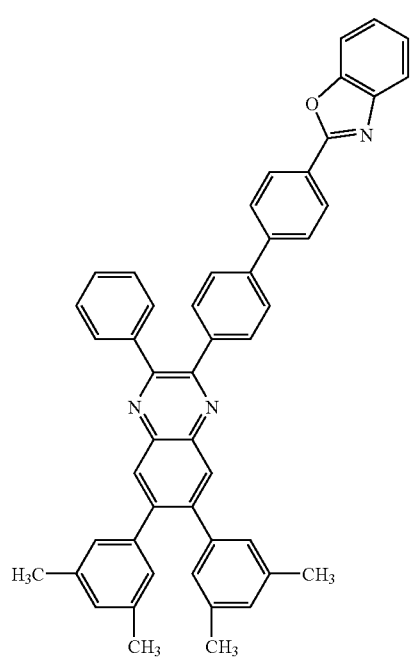

(173)
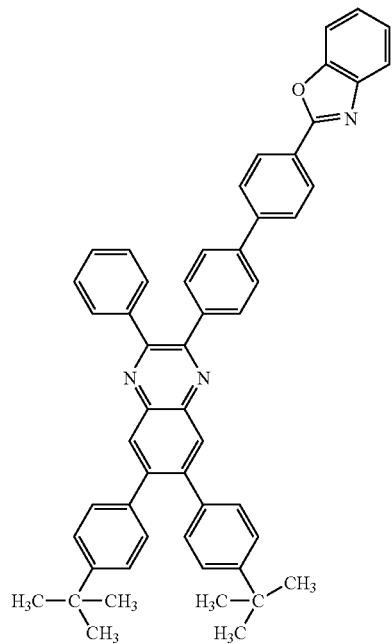
(174)
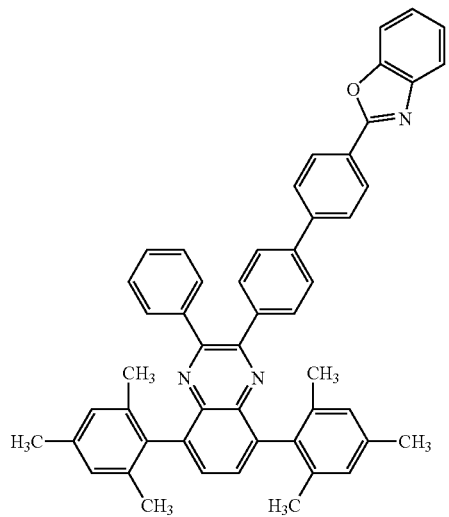
(175)
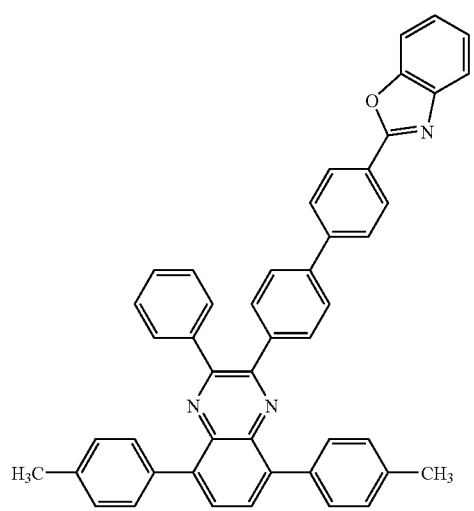
(176)
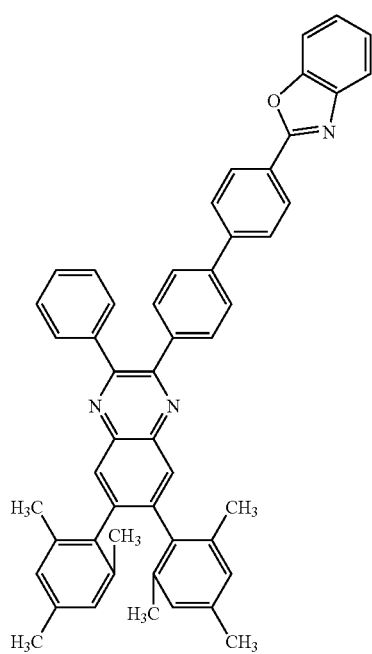

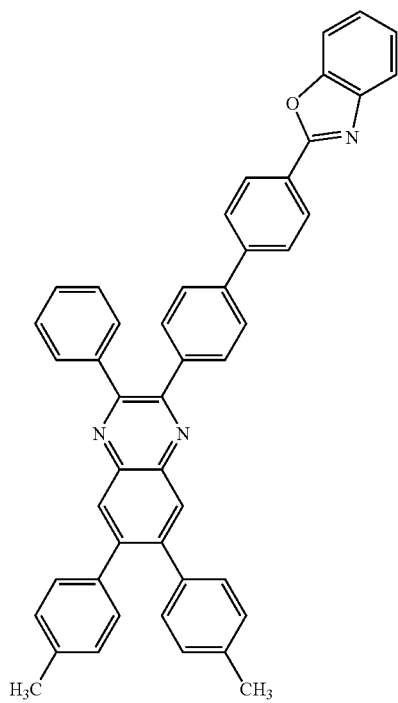
(177)
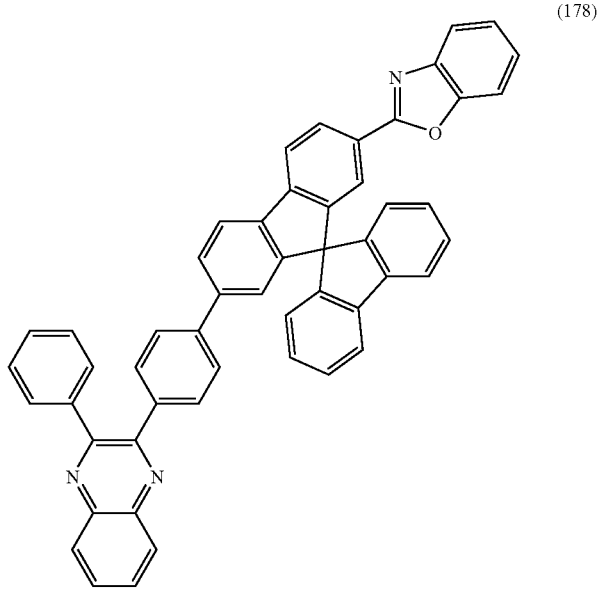
(178)
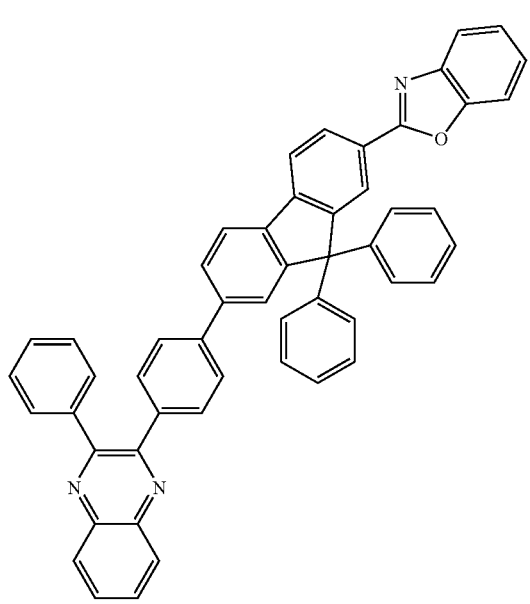
(179)
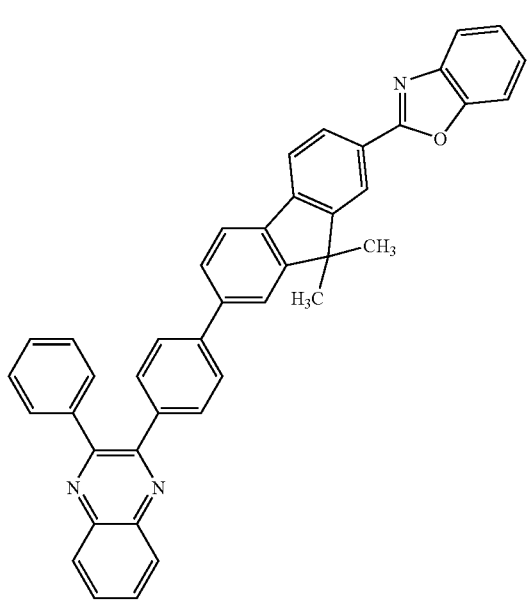
(180)

-continued
(181)
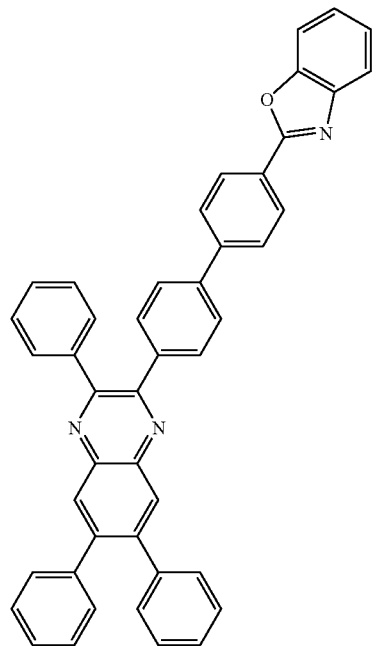
(182)
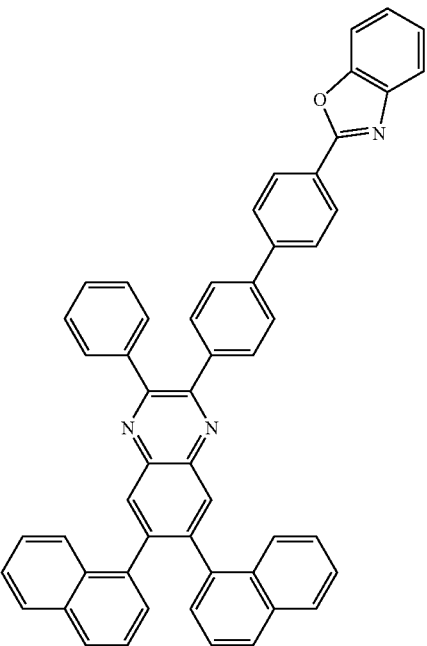
(183)
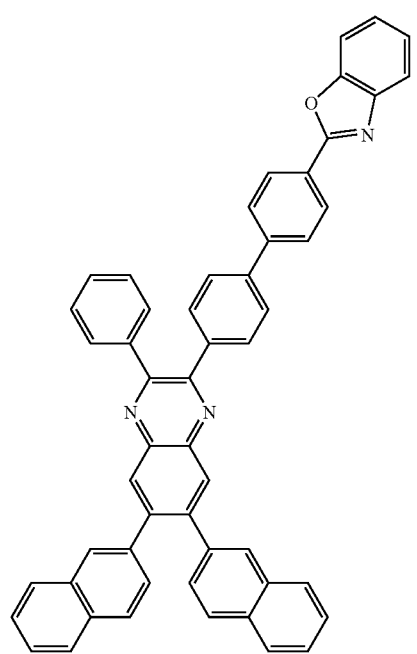
(184)
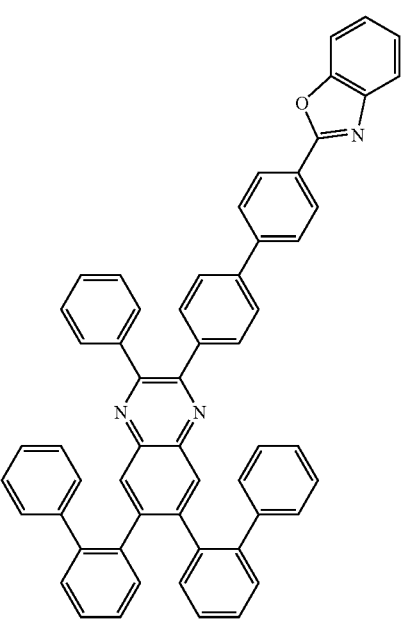

-continued
(185)
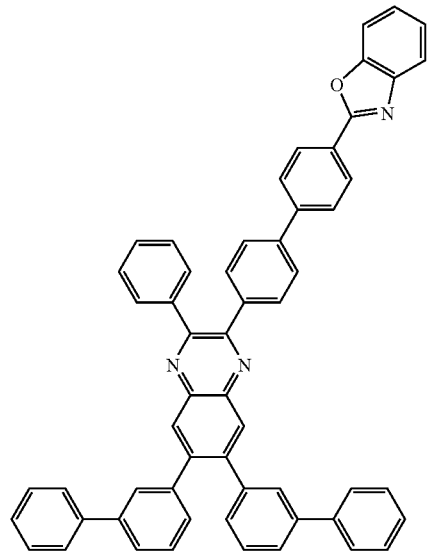
(186)
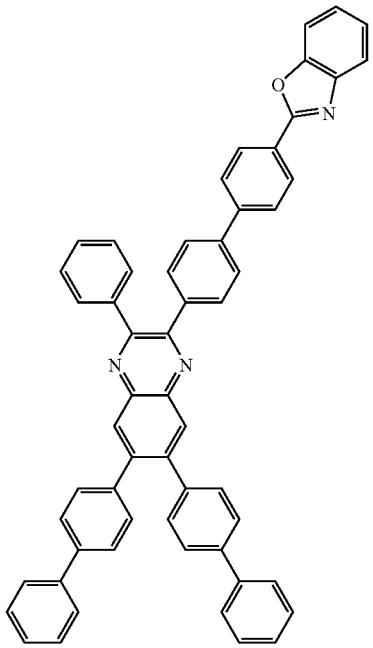
(187)
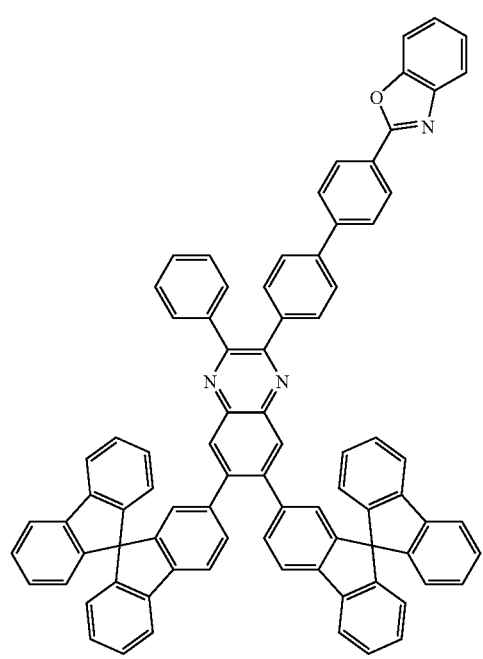
(188)
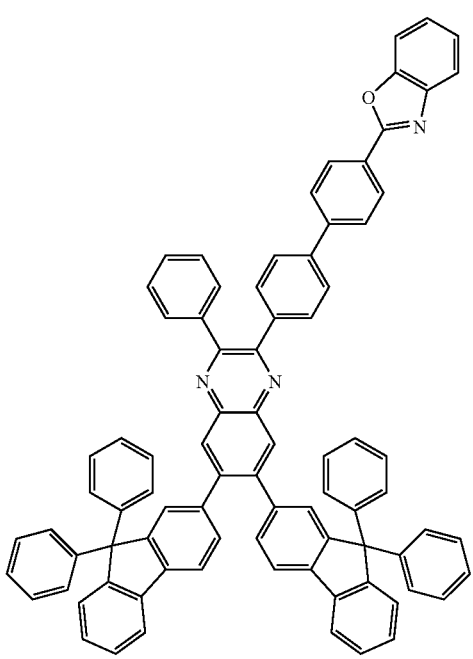

(189)
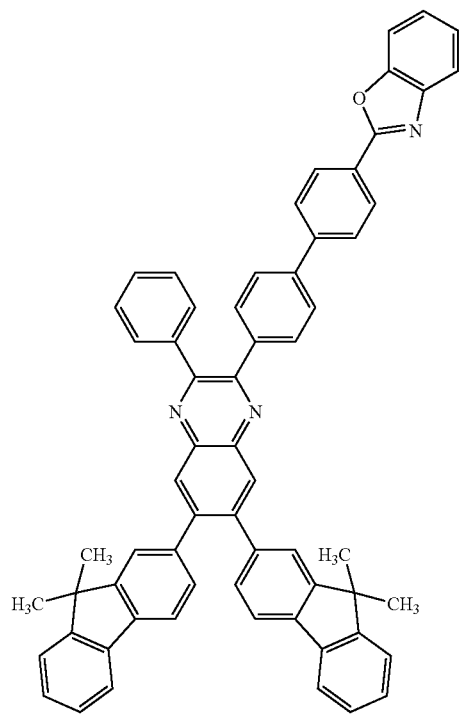
(190)
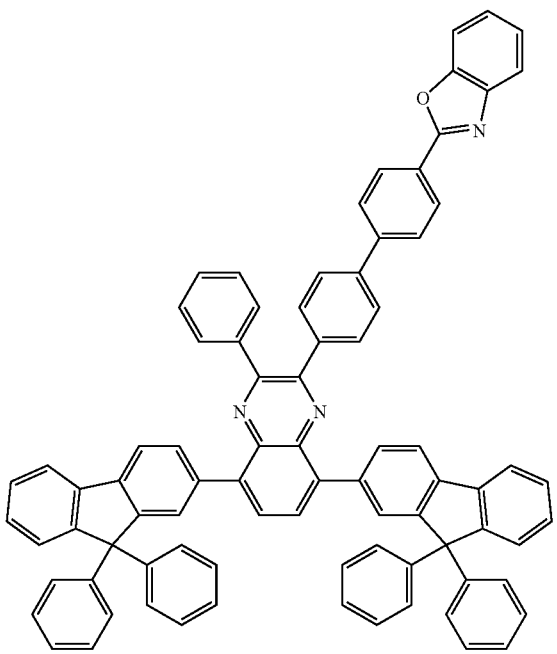
(191)
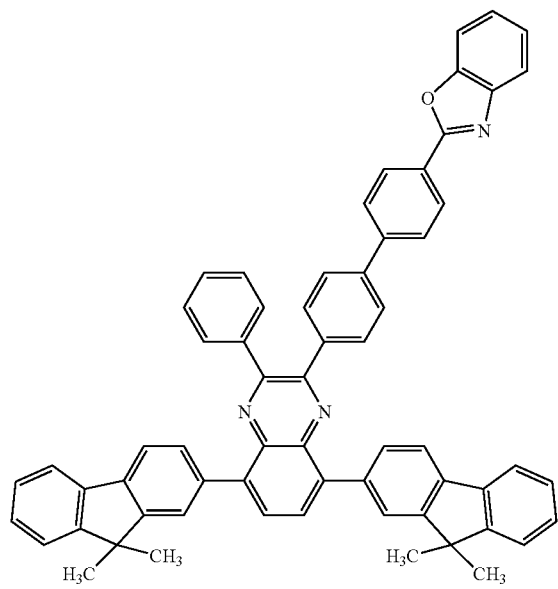
(201)
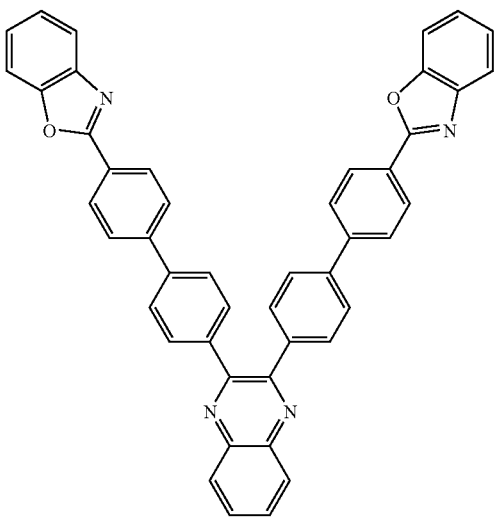

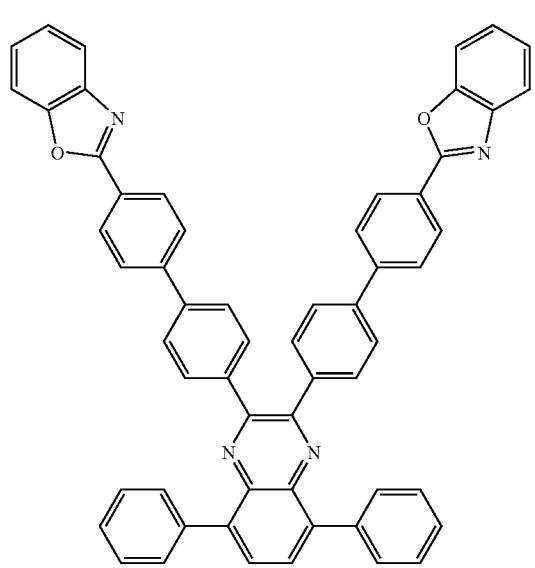 (202)
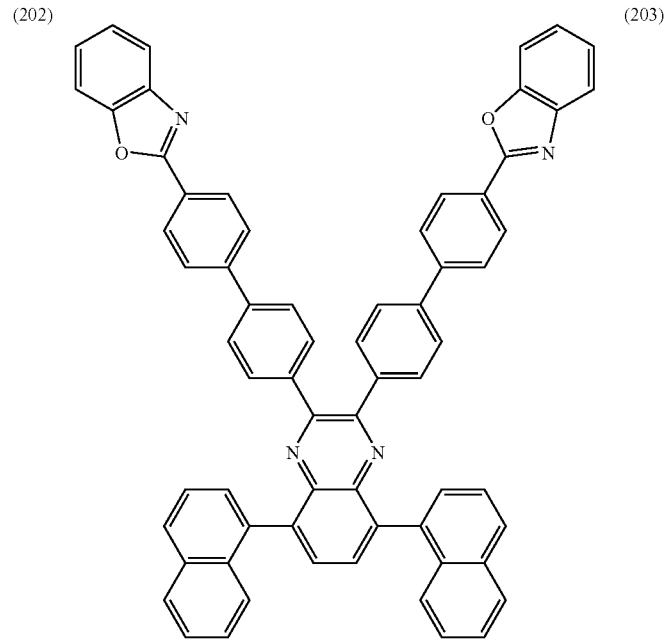 (203)
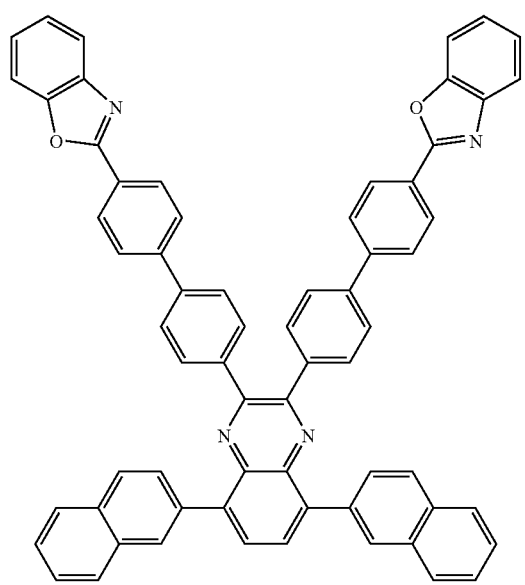 (204)
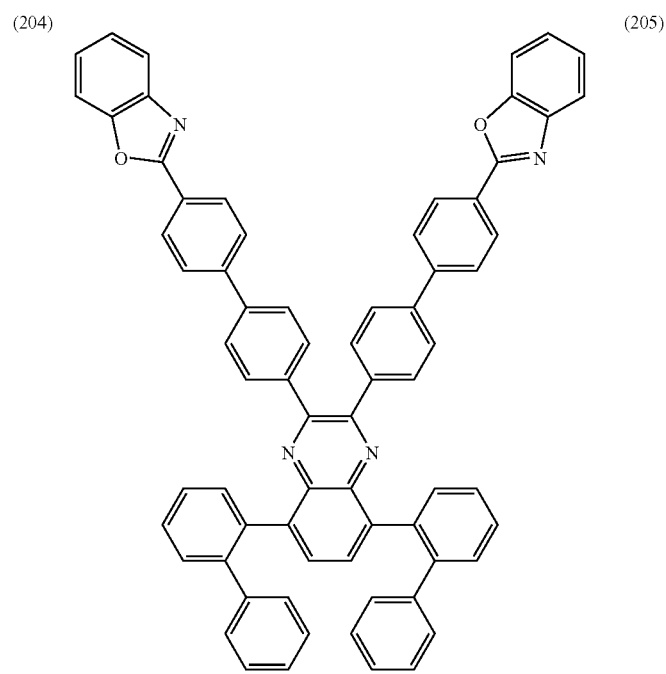 (205)

(206)
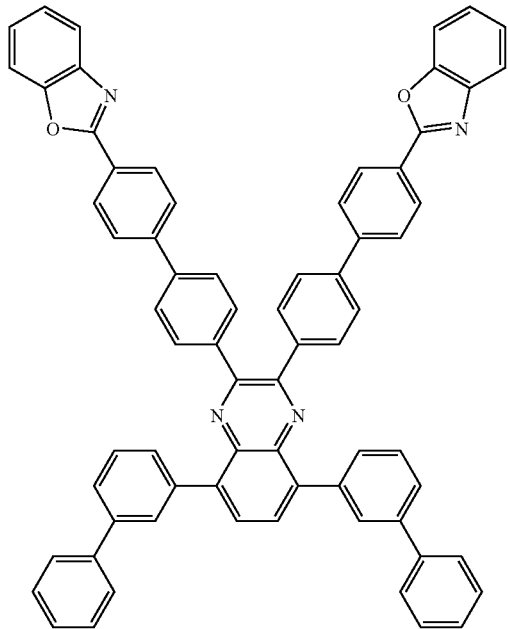
(207)
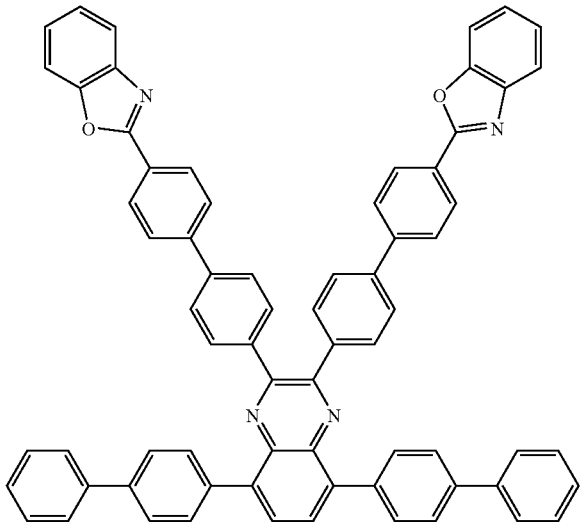
(208)
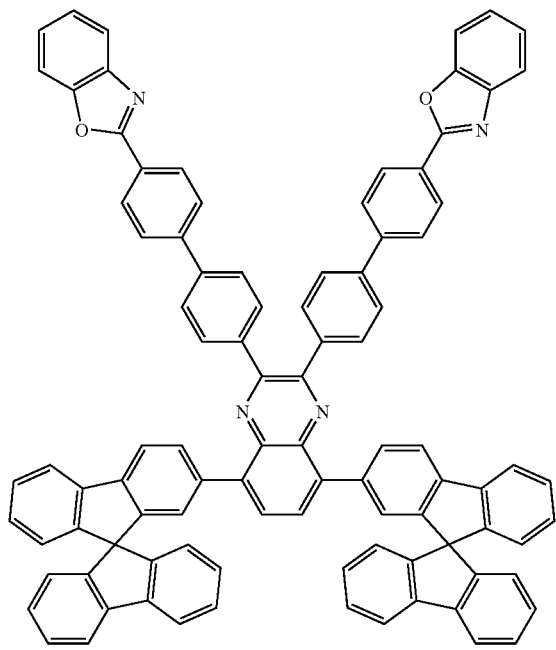
(209)
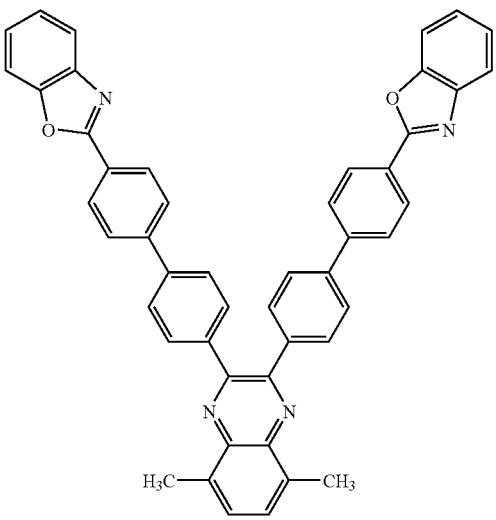

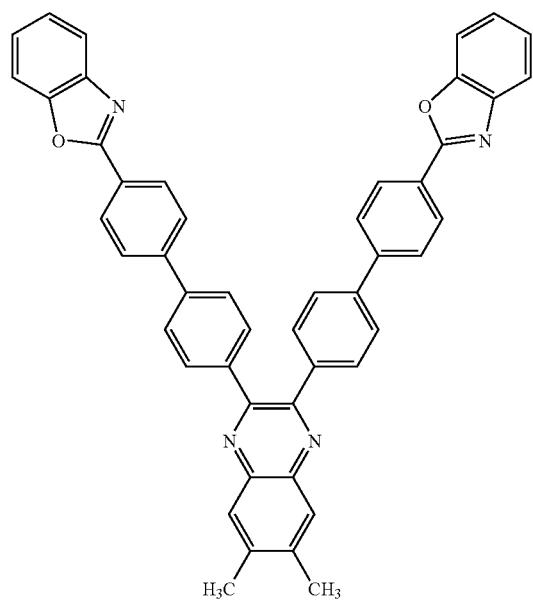 (210)
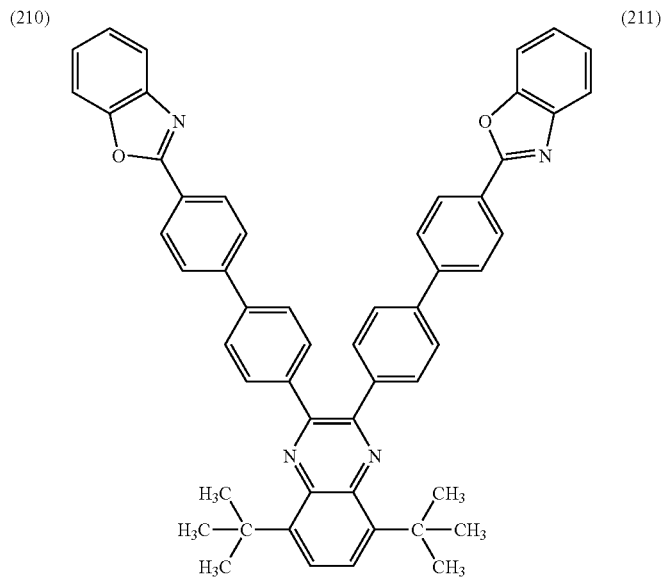 (211)
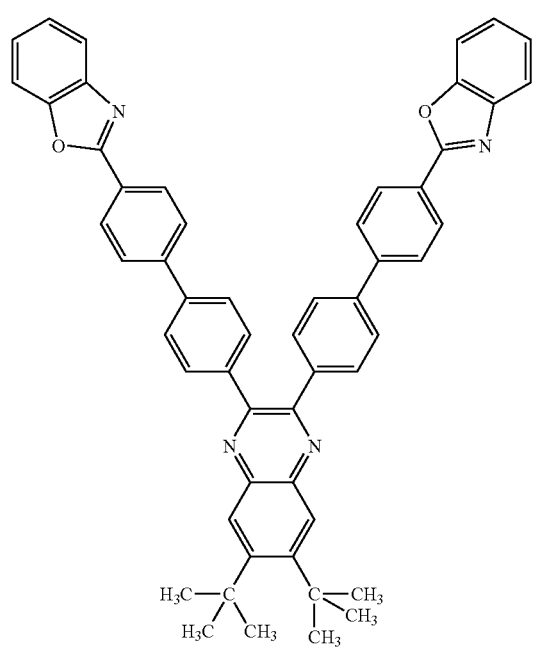 (212)
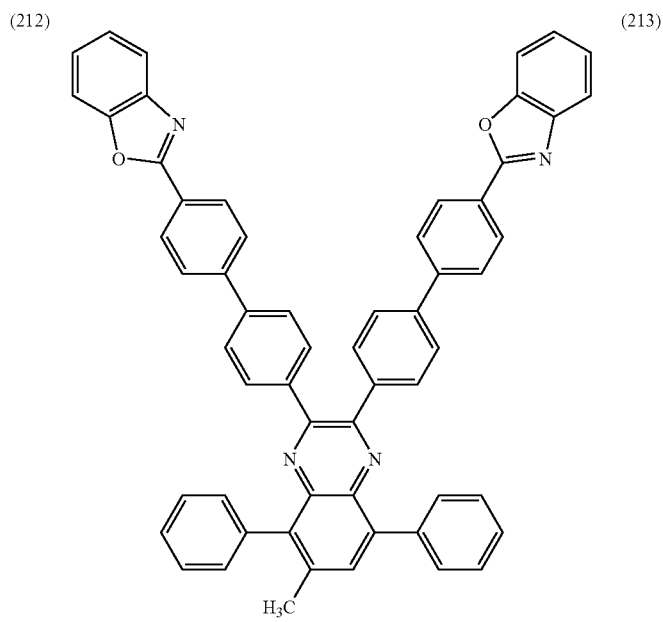 (213)

-continued
(214)
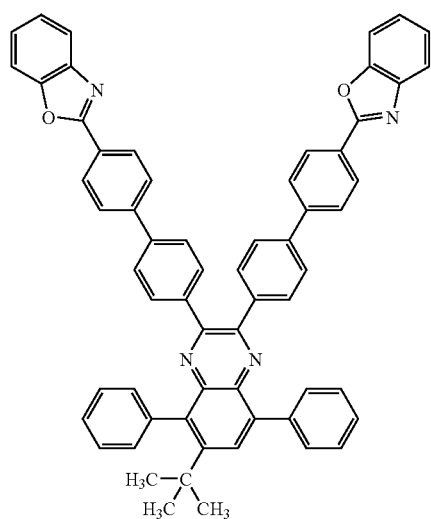
(215)
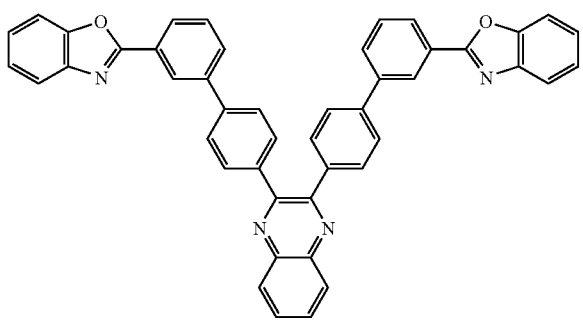
(216)
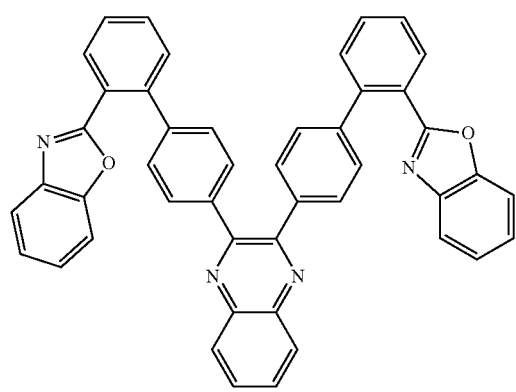
(217)
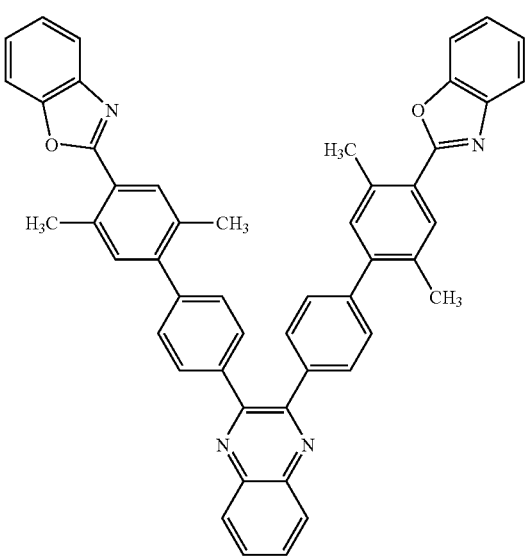
(218)
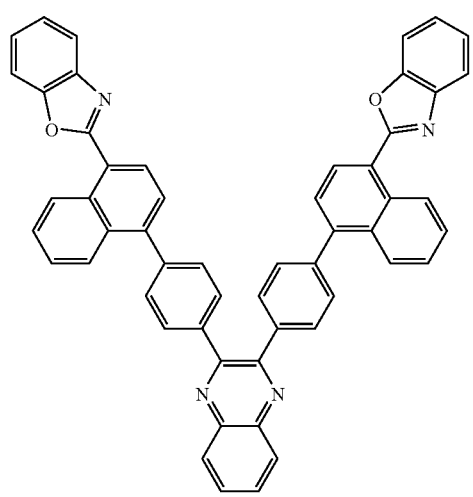
(219)
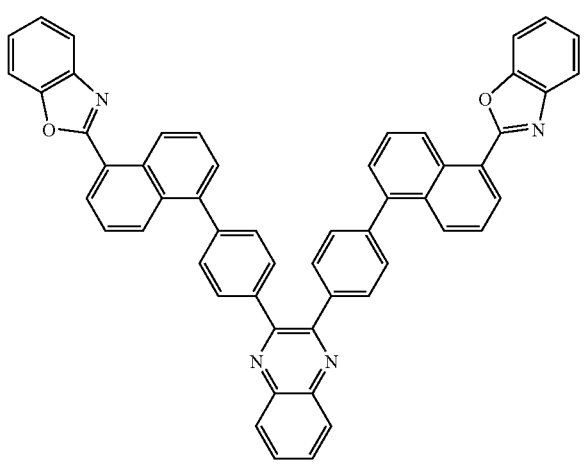

(220)
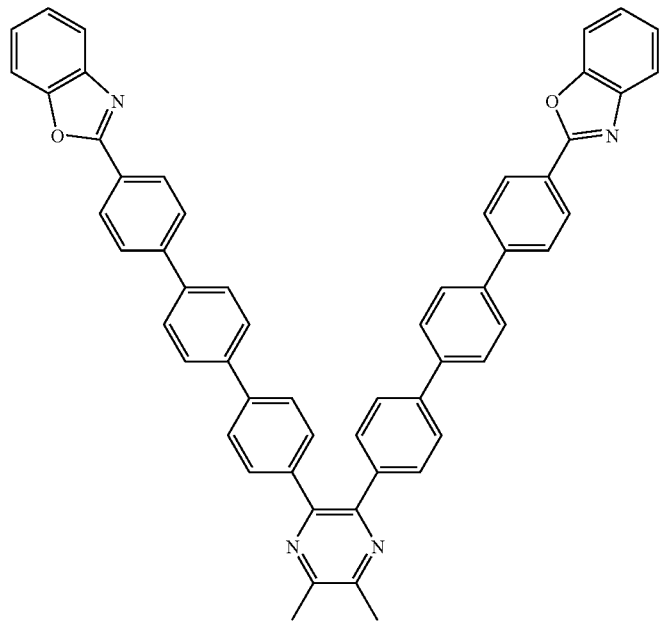
(221)
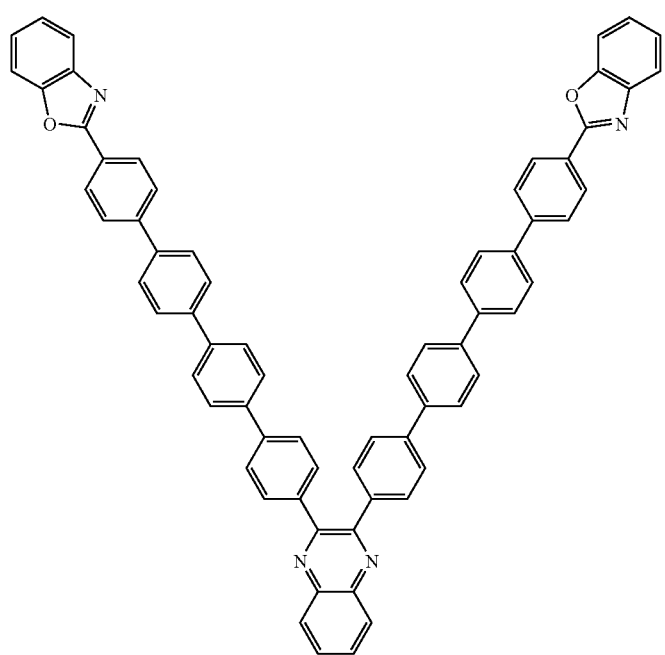
(222)
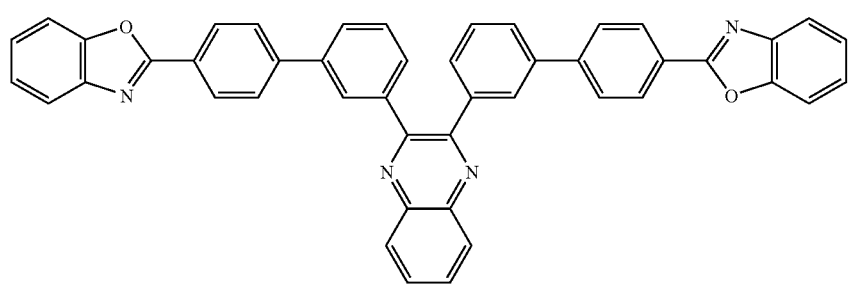

-continued
(223)
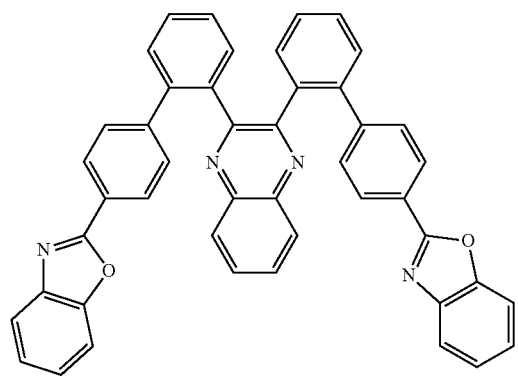
(224)
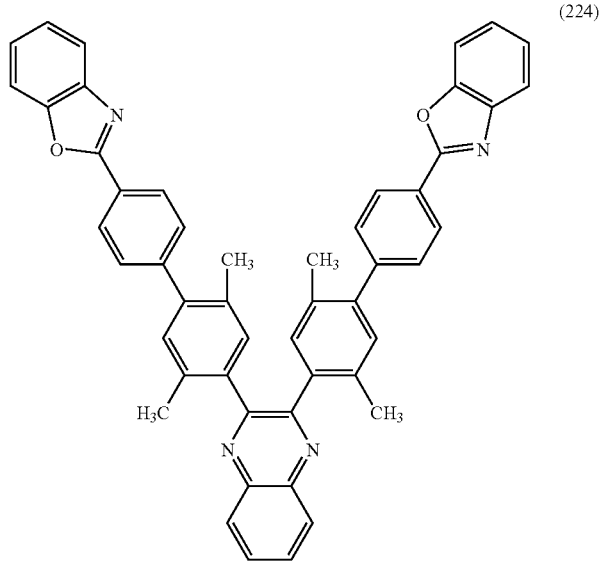
(225)
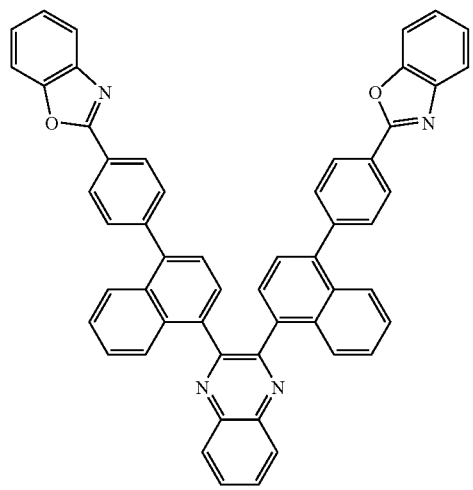
(226)
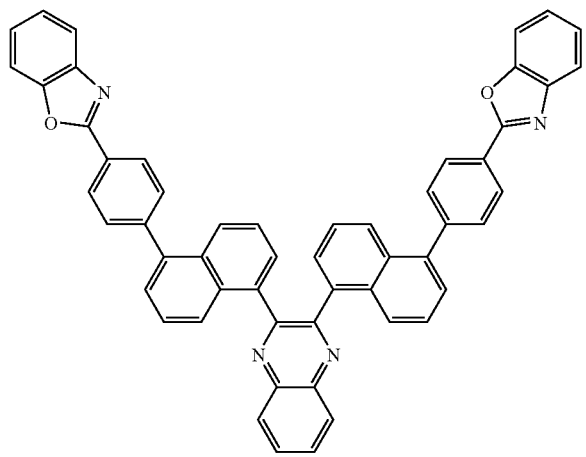
(227)
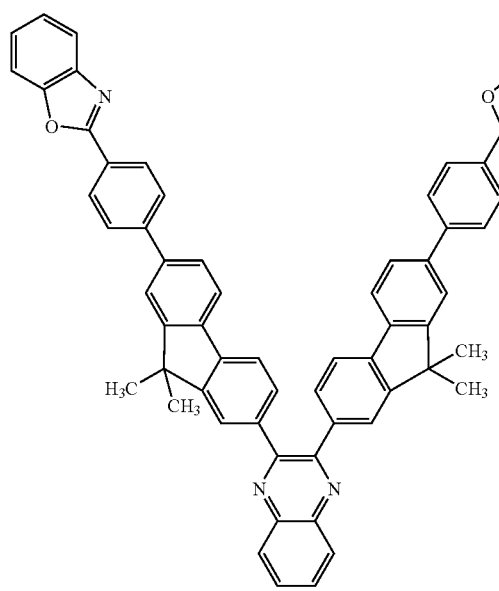
(228)
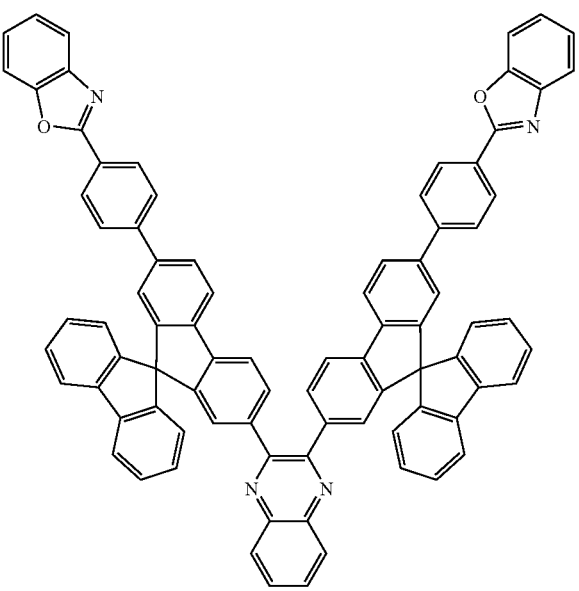

(229)
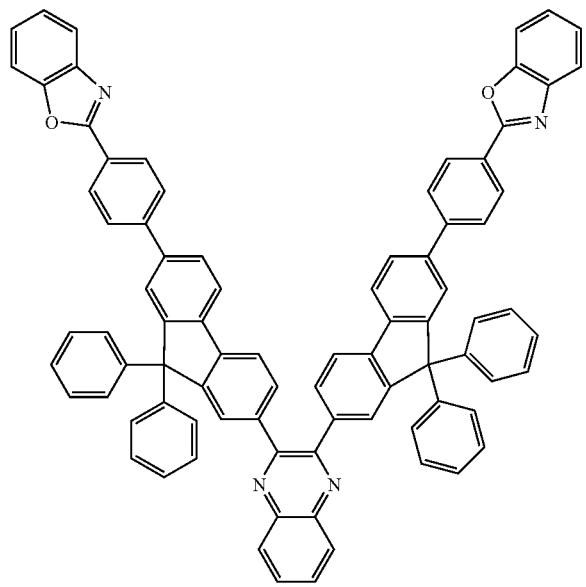
(230)
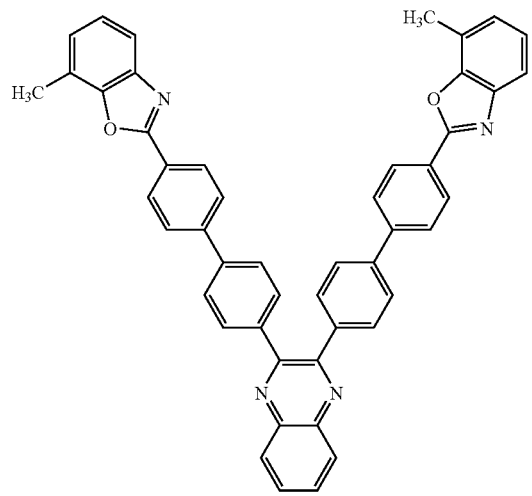
(231)
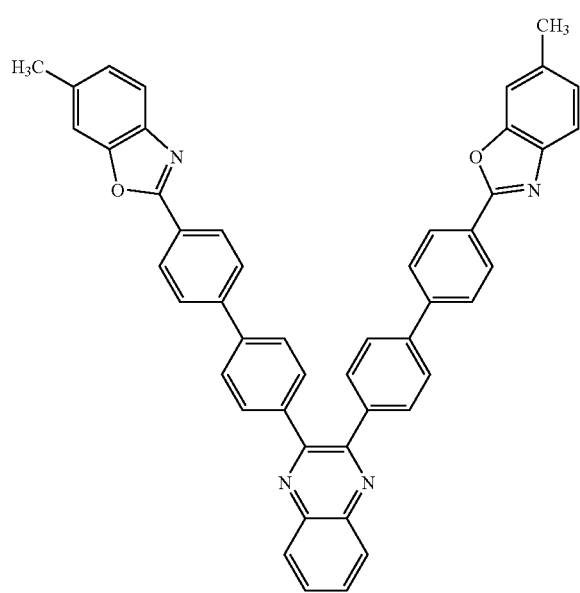
(232)
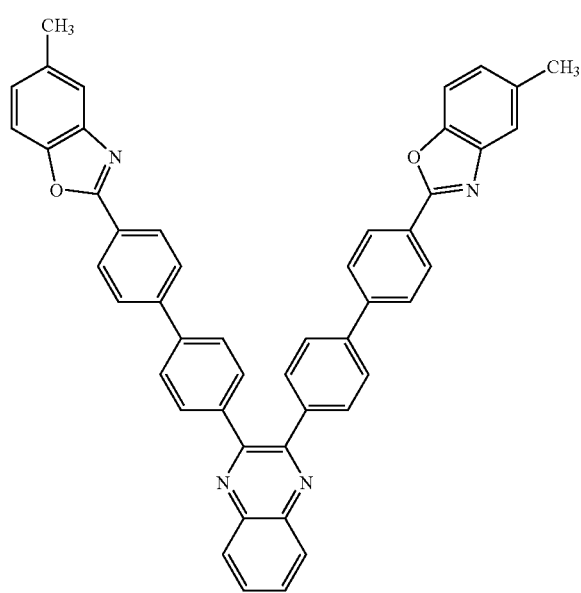

-continued
(233)
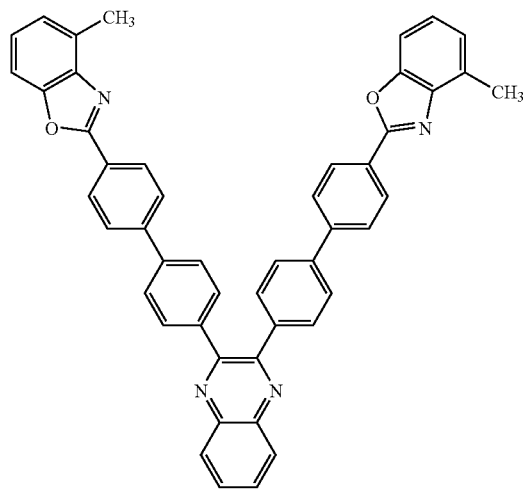
(234)
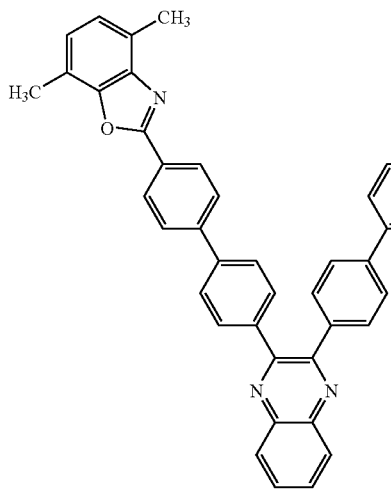
(235)
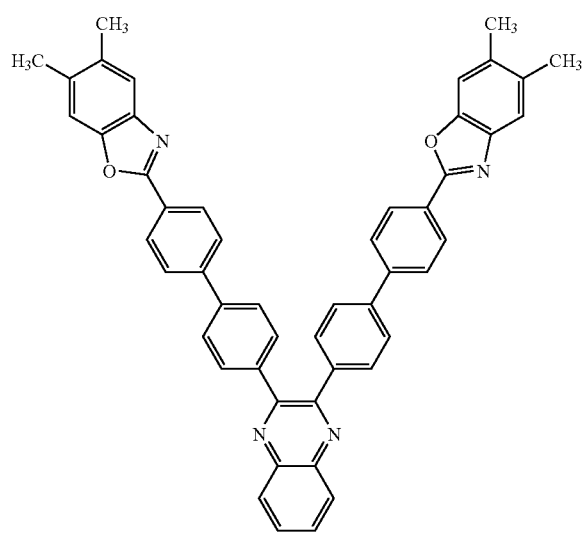
(236)
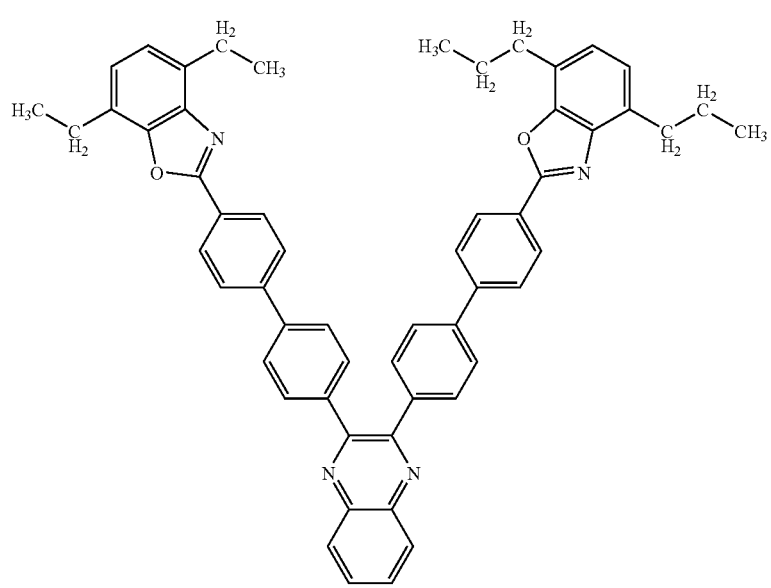

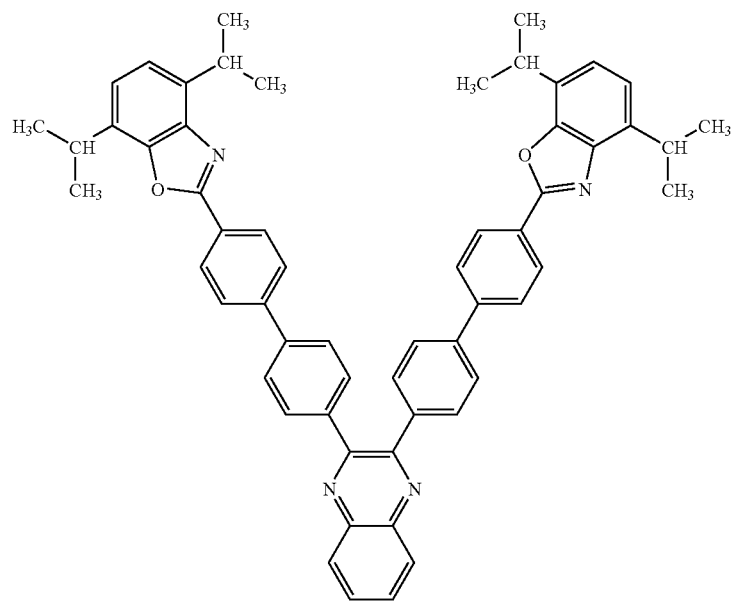
(237)
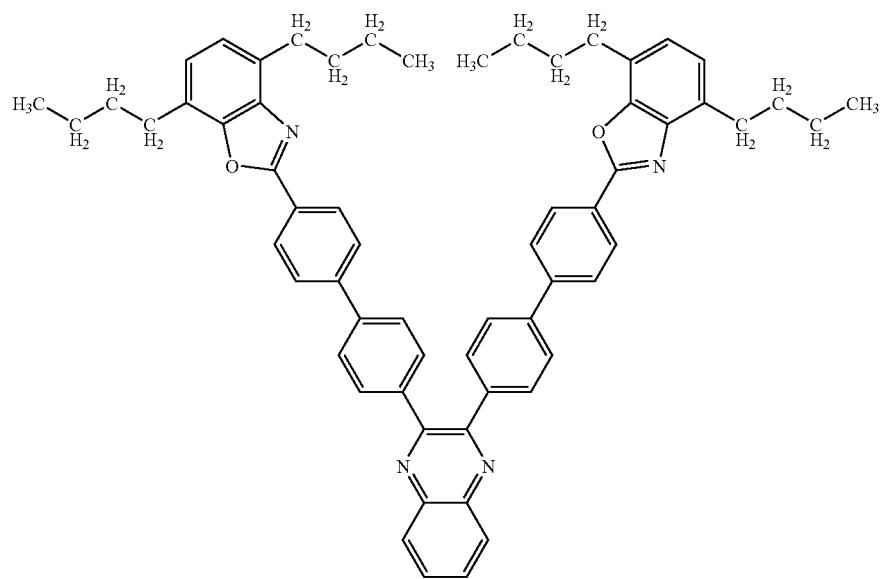
(238)

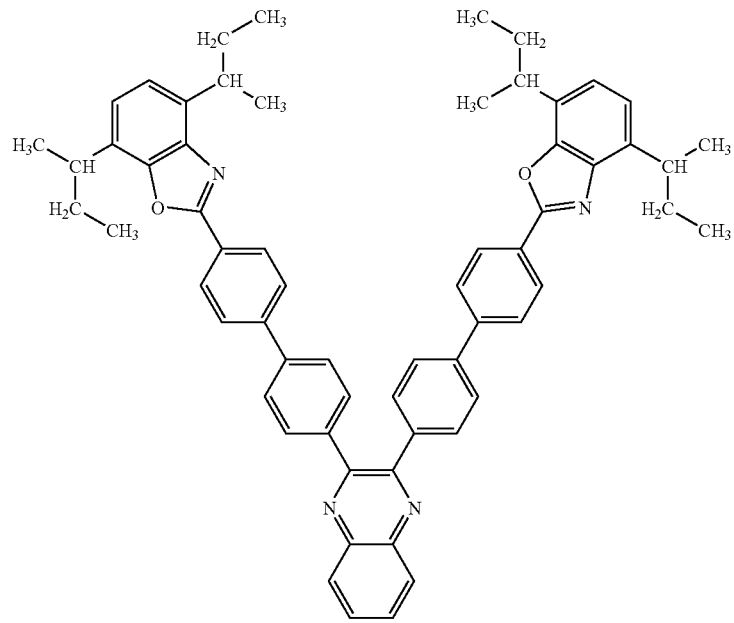
(239)
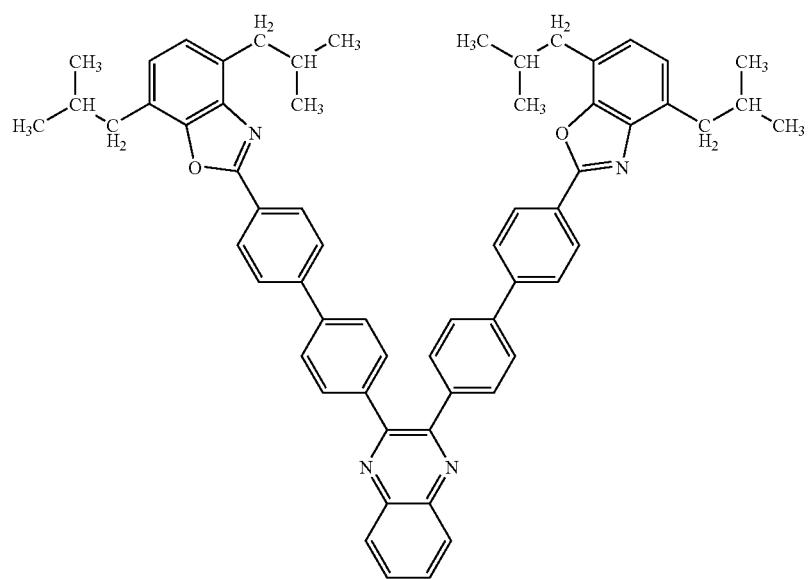
(240)

-continued
(241)
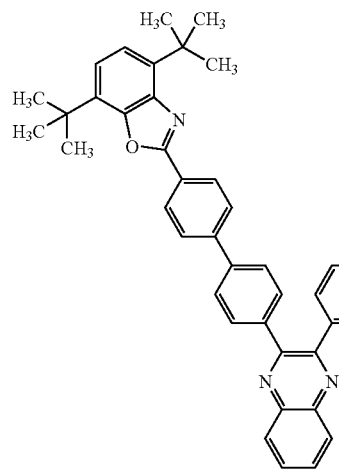
(242)
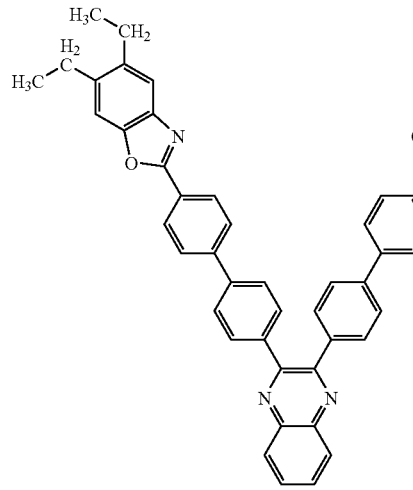
(243)
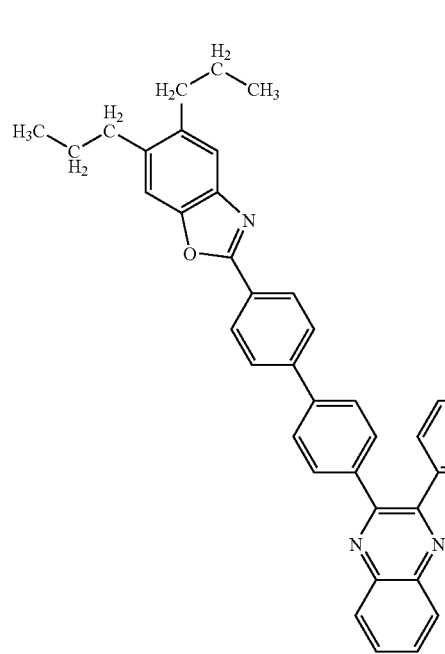

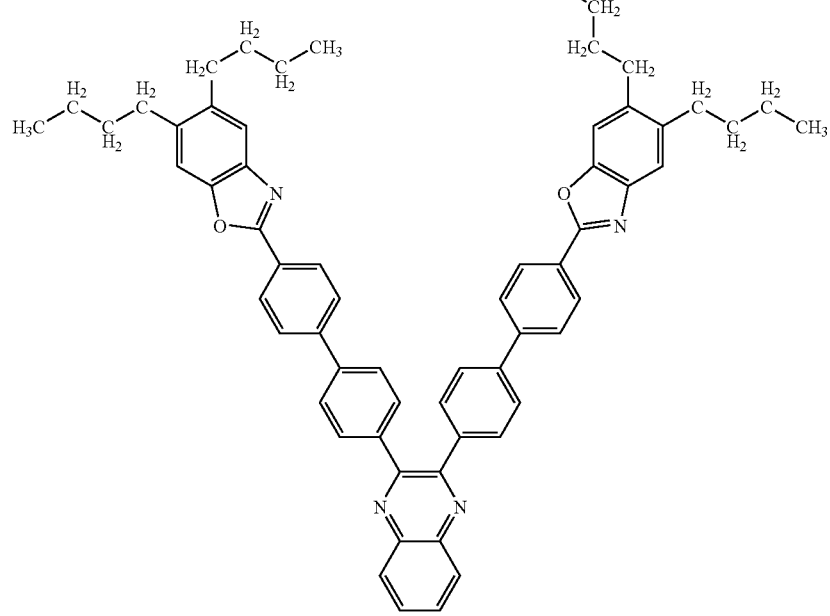
(244)
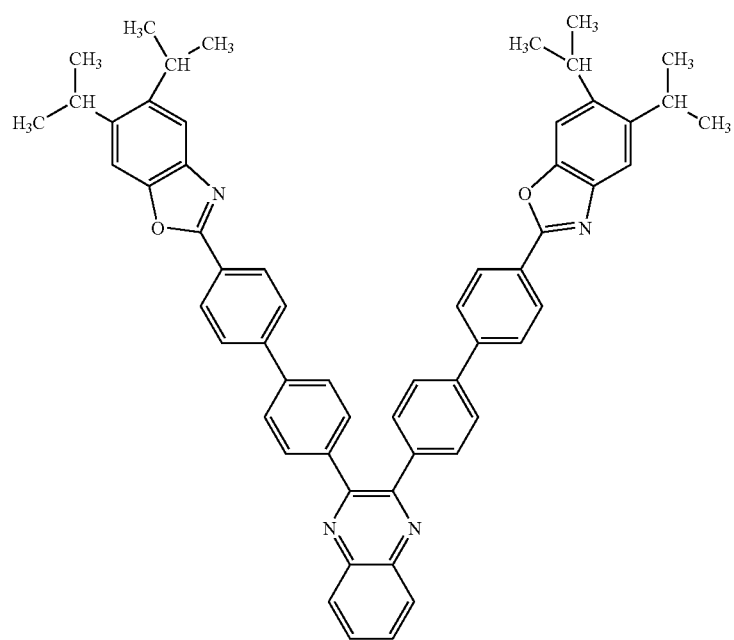
(245)

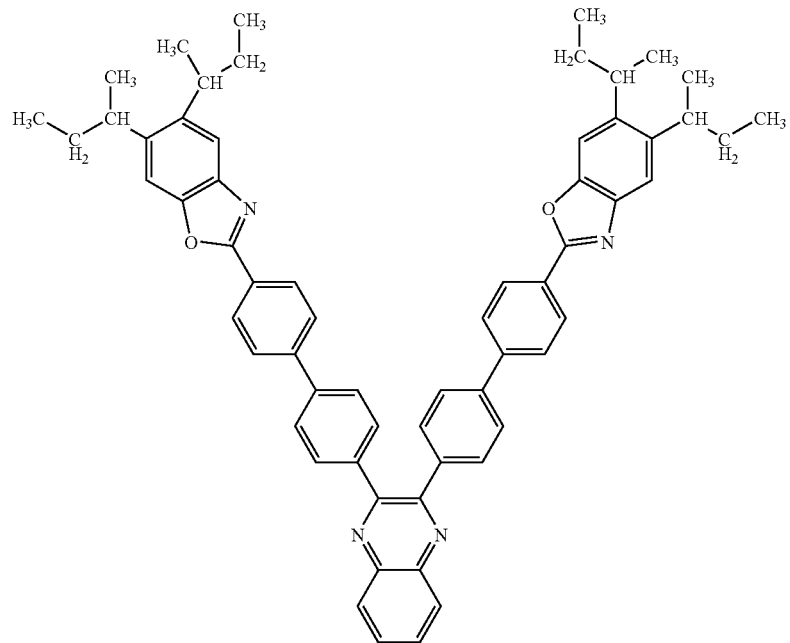
(246)
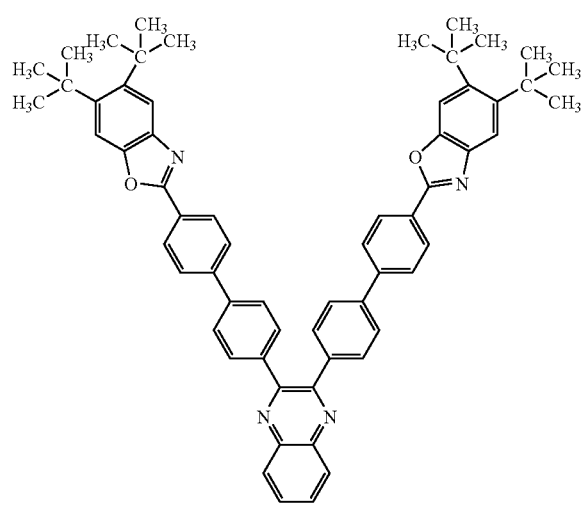
(247)
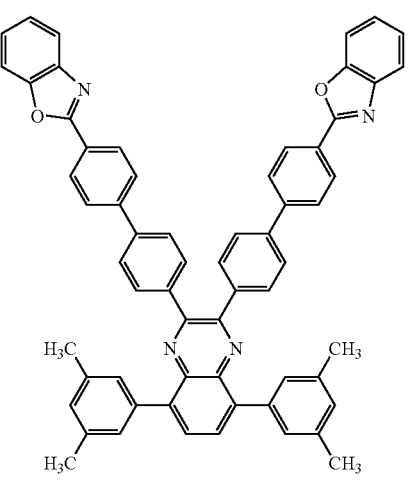
(248)

-continued
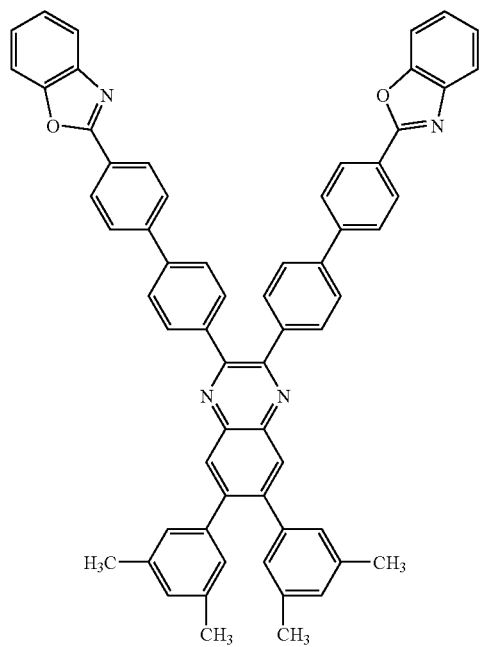 (249)
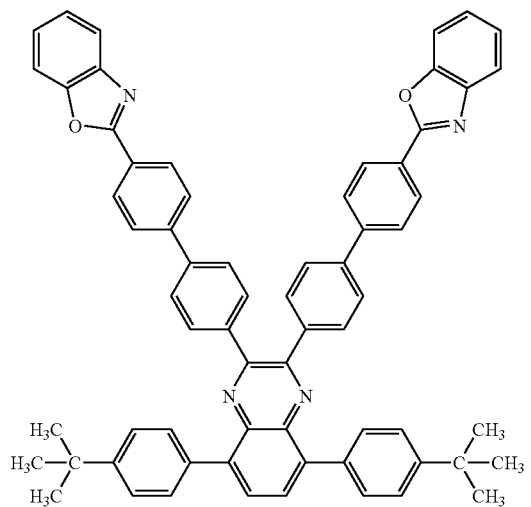 (250)
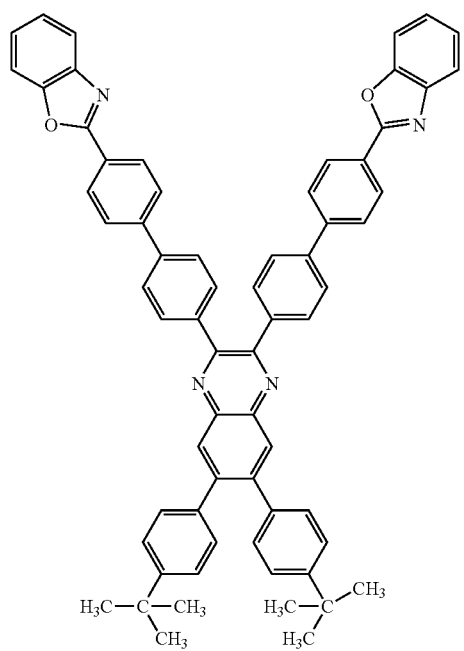 (251)
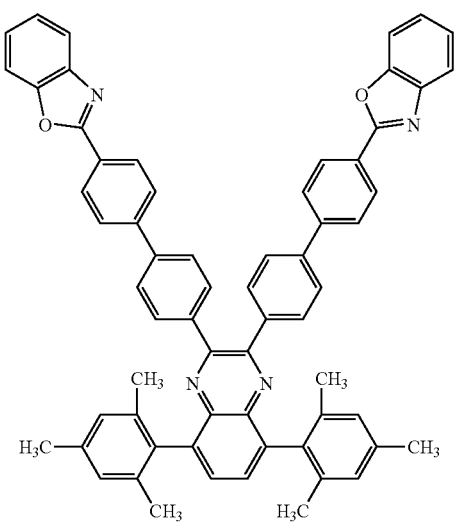 (252)

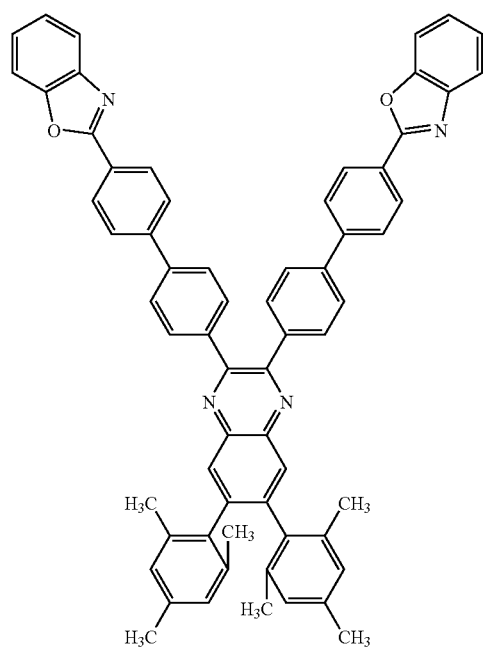
(253)
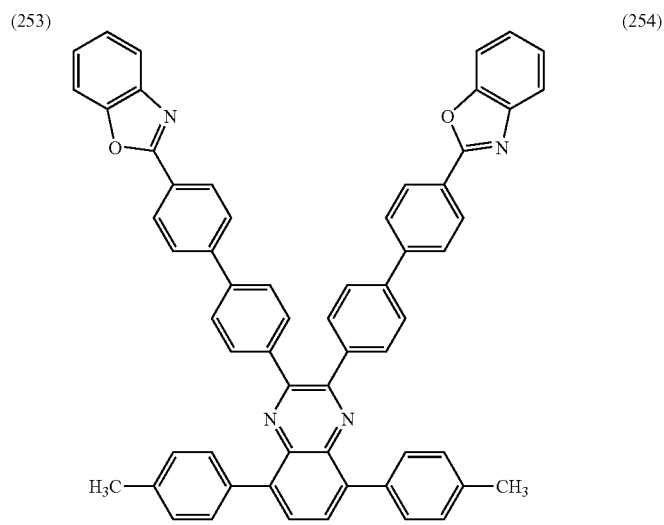
(254)
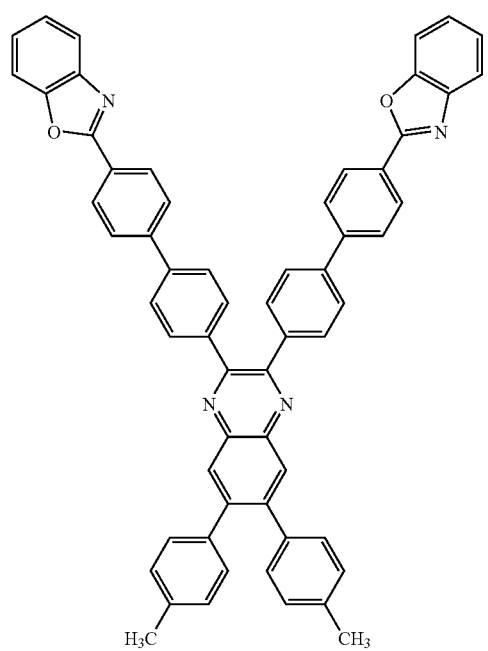
(255)

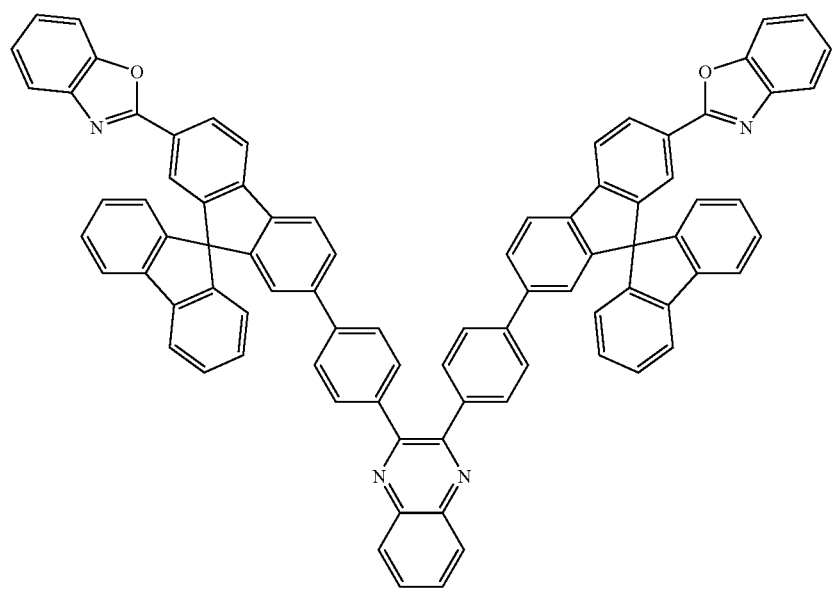
(256)
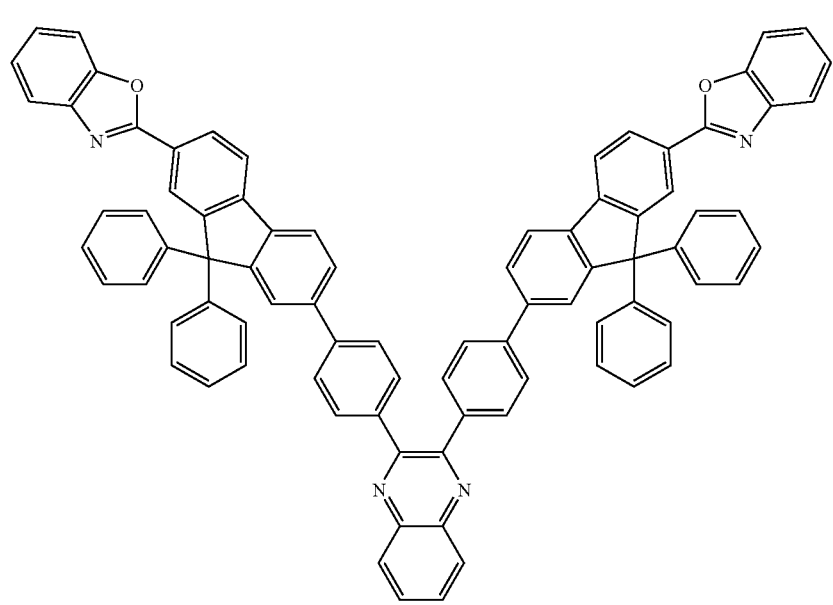
(257)

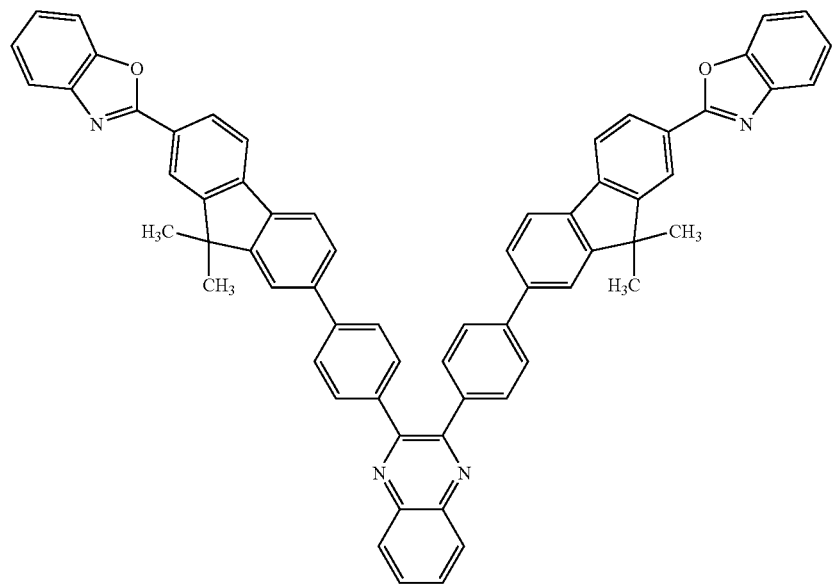
(258)
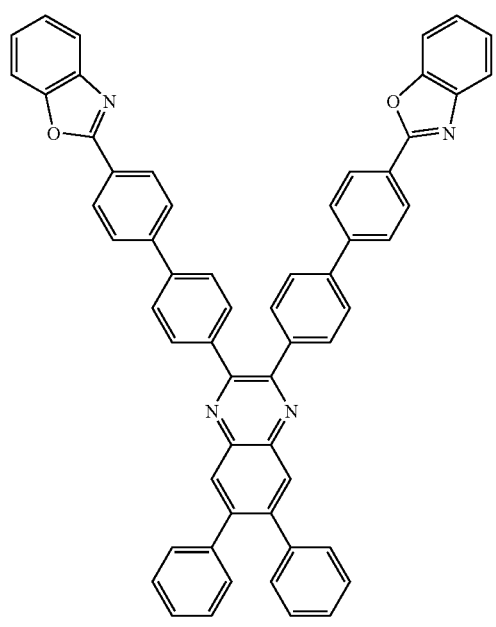
(259)
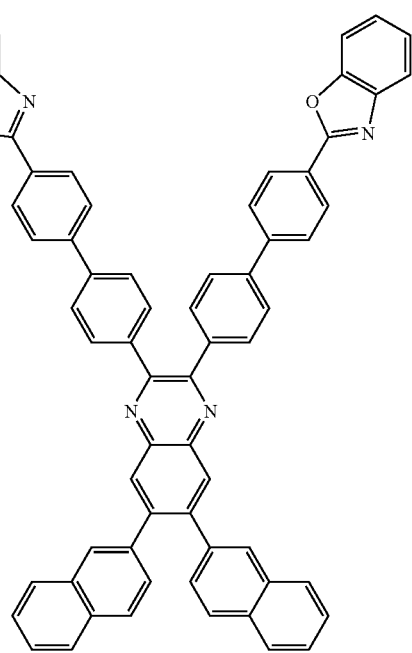
(260)

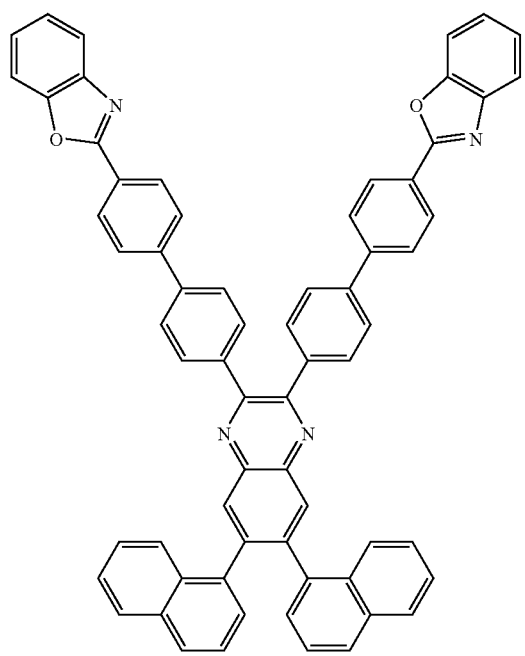 (261)
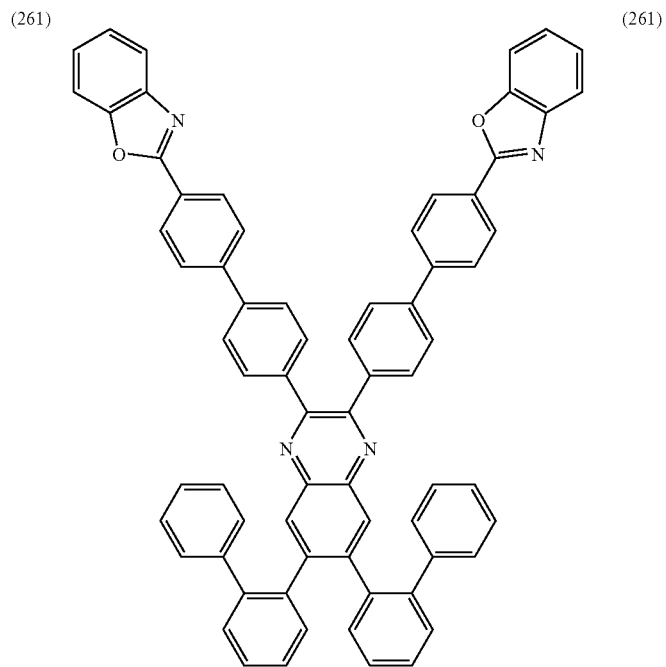 (261)
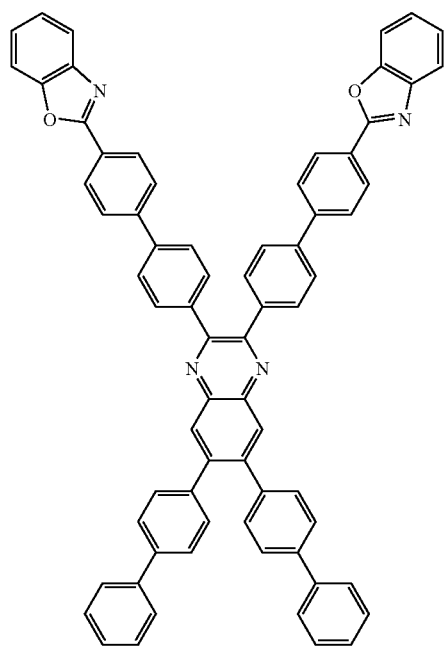 (262)
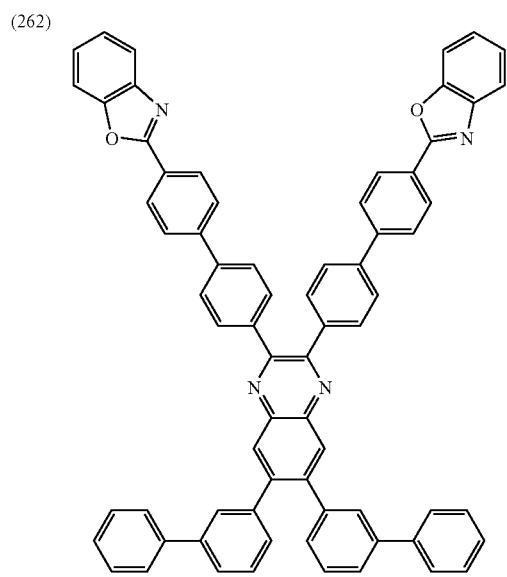 (263)

-continued
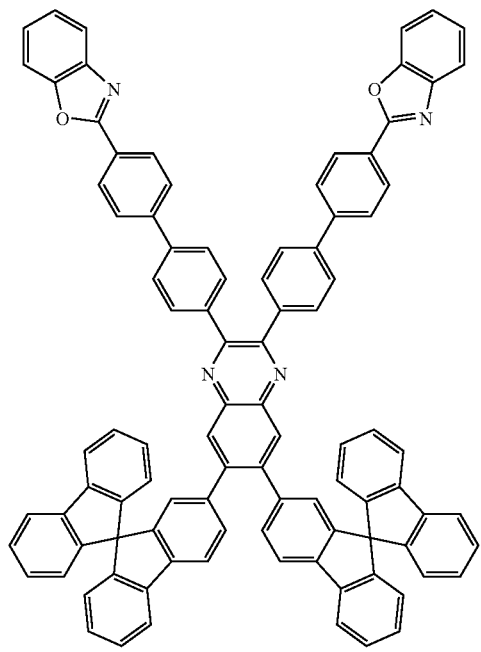 (264)
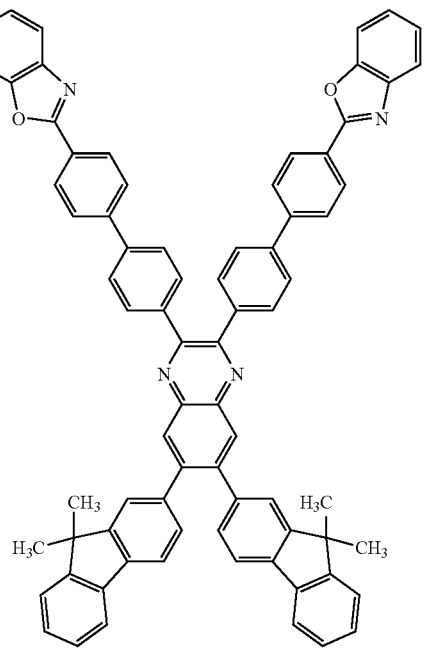 (265)
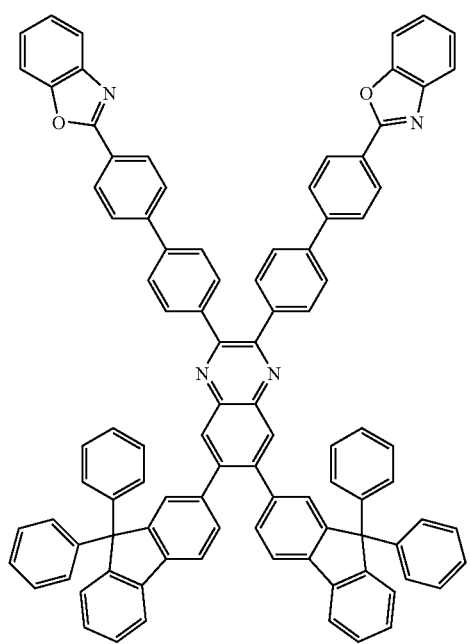 (266)
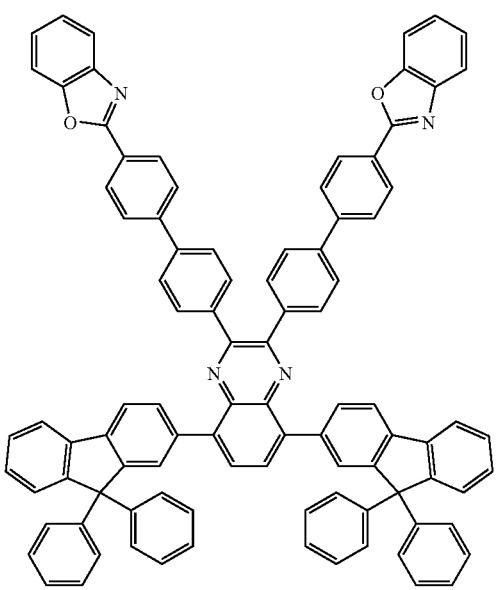 (267)

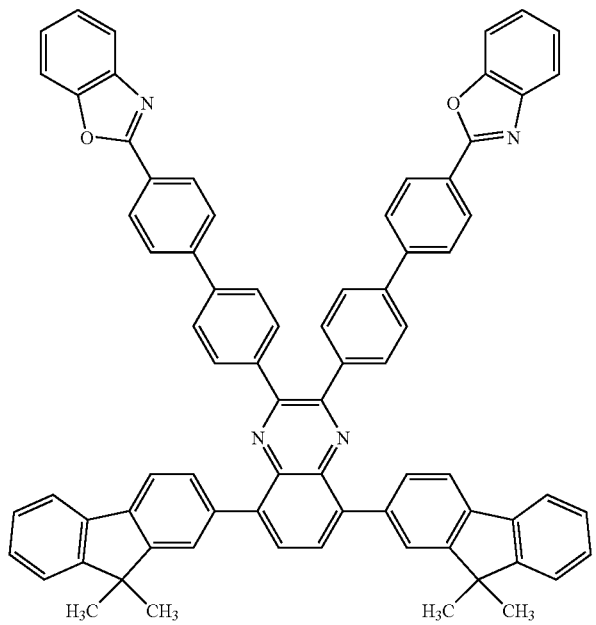

(268)

Various kinds of reactions can be applied to a synthesis method of the quinoxaline derivative of the present invention. For example, the quinoxaline derivative of the present invention can be synthesized by synthesis reactions shown below.

<Synthesis Method of Compound Represented by General Formula (G11)>

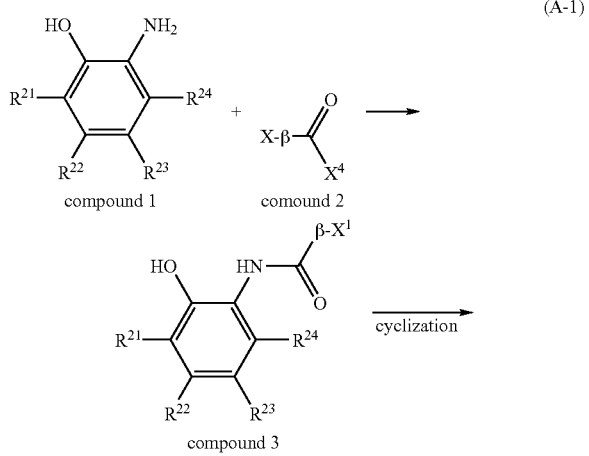

(A-1)

First, as shown in a synthesis scheme (A-1), an ortho-aminophenol derivative (a compound 1) which may include a substituent and an acyl halide (a compound 2) are reacted, so that a N-(2-hydroxyphenyl)arylamide derivative (a compound 3) is synthesized. A solvent used in this case can be an ether-based solvent such as diethyl ether or tetrahydrofuran or a halogen-based solvent such as chloroform, dichloromethane, or tetrachloromethane.

Next, the N-(2-hydroxyphenyl)arylamide derivative (the compound 3) is subjected to cyclodehydration, whereby a benzoxazole ring is formed. A dehydrating agent used at this time can be inorganic acid such as hydrochloric acid, sulfuric acid, or phosphoric acid or organic acid such as para-toluenesulfonic acid or trifuluoroacetic acid. A solvent used in this case can be a halogen-based solvent such as chloroform, dichloromethane, or tetrachloromethane or hydrocarbon such as benzene, toluene, or xylene. In such a manner, a 2-aryl-benzoxazole derivative (a compound 4) can be obtained. In the synthesis scheme (A-1), $R^{21}$ to $R^{24}$ may be the same or different from each other and each represent hydrogen or an alkyl group having 1 to 4 carbon atoms; and β represents an arylene group having 6 to 14 carbon atoms. $X^1$ represents halogen for which chlorine, bromine, or iodine is preferable. $X^4$ represents a halogen group for which chloride is particularly preferable.

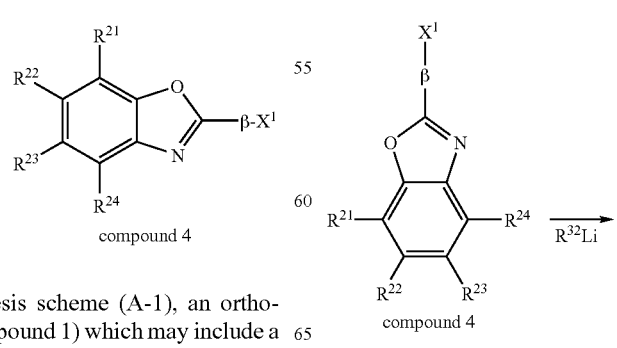

(A-2)

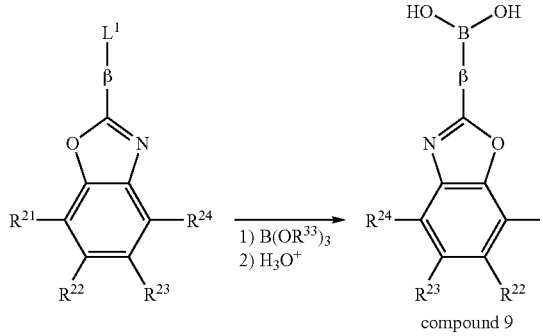

compound 9

Next, as shown in a synthesis scheme (A-2), the 2-arylbenzoxazole derivative (the compound 4) is lithiated with use of an alkyl lithium reagent and hydrolyzed with acid or water using a boron aregent, whereby a boronic acid of the benzoxazole derivative (a compound 9) can be obtained. In the synthesis scheme (A-2), β represents an arylene group having 6 to 13 carbon atoms; $R^{21}$ to $R^{24}$ each represent hydrogen or an alkyl group having 1 to 4 carbon atoms; $R^{32}$ represents an alkyl group having 1 to 6 carbon atoms; and $R^{33}$ represents an alkyl group having 1 to 6 carbon atoms. Further, $X^1$ represents halogen for which chlorine, bromine, or iodine is preferable. In the synthesis scheme (A-2), as a solvent that can be used, an ether-based solvent such as diethyl ether, tetrahydrofuran (THF), or cyclopentyl methyl ether can be given. As an alkyl lithium reagent, n-butyllithium, tert-butyllithium, methyl lithium, or the like can be given when $R^{32}$ is an n-butyl group, a tert-butyl group, a methyl group, or the like, respectively. As a boron reagent, trimethyl borate, triisopropyl borate, or the like can be given when $R^{33}$ is a methyl group, an isopropyl group, or the like, respectively. Further, the boronic acid obtained by the synthesis scheme (A-2) may be protected by ethyl alcohol, propyl alcohol, or the like to form an organoboron compound or may be protected by diol like ethylene glycol or pinacol to form an organoboron compound which forms a ring.

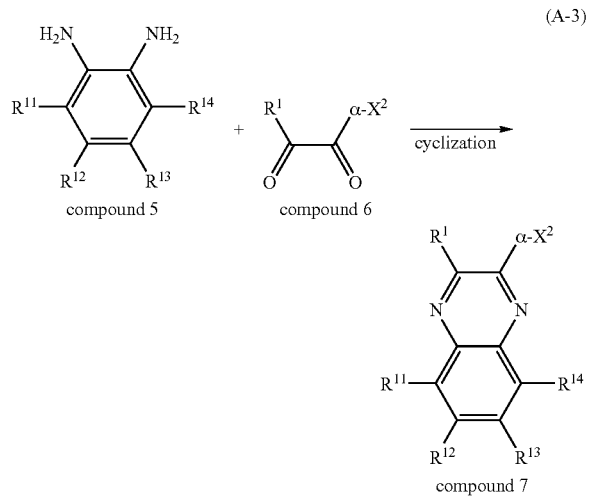

Next, as shown in a synthesis scheme (A-3), a 1,2-phenylenediamine derivative (a compound 5) which may include a substituent and a diketone derivative (a compound 6) are subjected to cyclodehydration, so that a quinoxaline derivative (a compound 7) can be obtained. In the synthesis scheme (A-3), α represents an arylene group having 6 to 13 carbon atoms; $R^1$ represents an alkyl group having 1 to 4 carbon atoms or an aryl group having 6 to 13 carbon atoms; and $R^{11}$ to $R^{14}$ each represent any of hydrogen, an alkyl group having 1 to 4 carbon atoms, or an aryl group having 6 to 13 carbon atoms. Further, $X^2$ represents halogen or a triflate group. In a case where $X^2$ is halogen, chlorine, bromine, or iodine is preferable. In the synthesis scheme (A-3), as a solvent that can be used, a halogen-based solvent such as dichloromethane, chloroform, or carbon tetrachloride, alcohol such as ethanol, methanol, or isopropanol, acetic acid, a sodium carbonate aqueous solution, a sodium hydrogen sulfate aqueous solution, a sodium acetate aqueous solution, a mixed solvent of sodium acetate aqueous solution and acetic acid, or the like can be given. Further, in a case where the halogen-based solvent is used, chloroform or carbon tetrachloride having higher boiling point is preferably used.

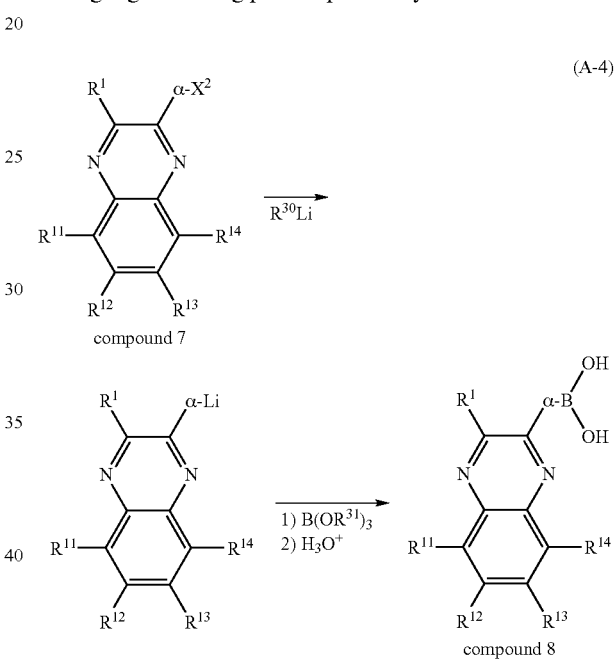

Next, as shown in a synthesis scheme (A-4), the quinoxaline derivative (the compound 7) is lithiated with use of an alkyl lithium reagent and hydrolyzed with acid or water using a boron reagent, whereby a boronic acid of the quinoxaline derivative (a compound 8) can be obtained. In the synthesis scheme (A-4), α represents an arylene group having 6 to 13 carbon atoms; $R^1$ represents an alkyl group having 1 to 4 carbon atoms or an aryl group having 6 to 13 carbon atoms; $R^{11}$ to $R^{14}$ each represent any of hydrogen, an alkyl group having 1 to 4 carbon atoms, or an aryl group having 6 to 13 carbon atoms; $R^{30}$ represents an alkyl group having 1 to 6 carbon atoms; and $R^{31}$ represents an alkyl group having 1 to 6 carbon atoms. $X^2$ represents halogen. In the synthesis scheme (A-4), as a solvent that can be used, an ether-based solvent such as diethyl ether, tetrahydrofuran (THF), or cyclopentyl methyl ether can be given. As an alkyl lithium reagent, n-butyllithium, tert-butyllithium, methyl lithium, or the like can be given when $R^{30}$ is an n-butyl group, a tert-butyl group, a methyl group, or the like, respectively. As a boron reagent, trimethyl borate, triisopropyl borate, or the like can be given when $R^{31}$ is a methyl group, an isopropyl group, or the like, respectively. Further, the boronic acid obtained by the synthesis scheme (A-4) may be protected by ethyl alcohol, propyl alcohol, or the like to form an organoboron compound or may be protected by diol like ethylene glycol or pinacol to form an organoboron compound which forms a ring.

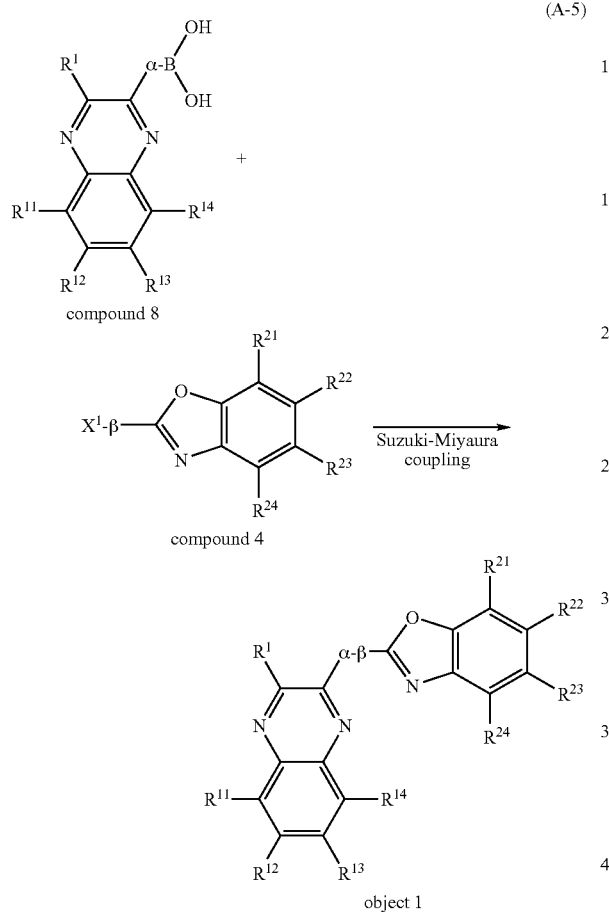

Next, as shown in a synthesis scheme (A-5), the boronic acid of the quinoxaline derivative (the compound 8) and the 2-arylbenzoxazole derivative (the compound 4) are coupled by Suzuki-Miyaura Coupling using a palladium catalyst, so that a 2-arylbenzoxazole-substituted quinoxaline derivative (an object 1) of a target can be obtained. In the synthesis scheme (A-5), $R^1$ represents an alkyl group having 1 to 4 carbon atoms or an aryl group having 6 to 13 carbon atoms; $R^{11}$ to $R^{14}$ may be the same or different from each other and each represent any of hydrogen, an alkyl group having 1 to 4 carbon atoms, or a substituted or unsubstituted aryl group having 6 to 13 carbon atoms; and $R^{21}$ to $R^{24}$ may be the same or different from each other and each represent hydrogen or an alkyl group having 1 to 4 carbon atoms. Further, $X^1$ represents halogen or a triflate group; α represents an arylene group having 6 to 13 carbon atoms; and β represents an arylene group having 6 to 13 carbon atoms. In the case where $X^1$ is halogen, chlorine, bromine, or iodine is preferable, and in particular, bromine or iodine is more preferable. In the synthesis scheme (A-5), as the palladium catalyst that can be used, palladium(II) acetate, tetrakis(triphenylphosphine)palladium(0), bis(triphenylphosphine)palladium(II) dichloride, or the like can be given. In the synthesis scheme (A-5), as a ligand of the palladium catalyst that can be used, tri(ortho-tolyl)phosphine, triphenylphosphine, tricyclohexylphosphine, or the like can be given. In the synthesis scheme (A-5), as a base that can be used, an organic base such as sodium tert-butoxide, an inorganic base such as potassium carbonate, or the like can be given. In the synthesis scheme (A-5), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferably. In the synthesis scheme (A-5), instead of the compound 8, an organoboron compound may be used, which is obtained by protecting the boronic acid of the compound 8 by ethyl alcohol, propyl alcohol, or the like. Alternatively, an organoboron compound which forms a ring may be used, which is obtained by protecting the boronic acid of the compound 8 by diol like ethylene glycol or pinacol. Further, instead of Suzuki-Miyaura Coupling, Cross Coupling Reaction using an organoaluminum compound, an organozirconium compound, an organozinc compound, an organotin compound, or the like may be used.

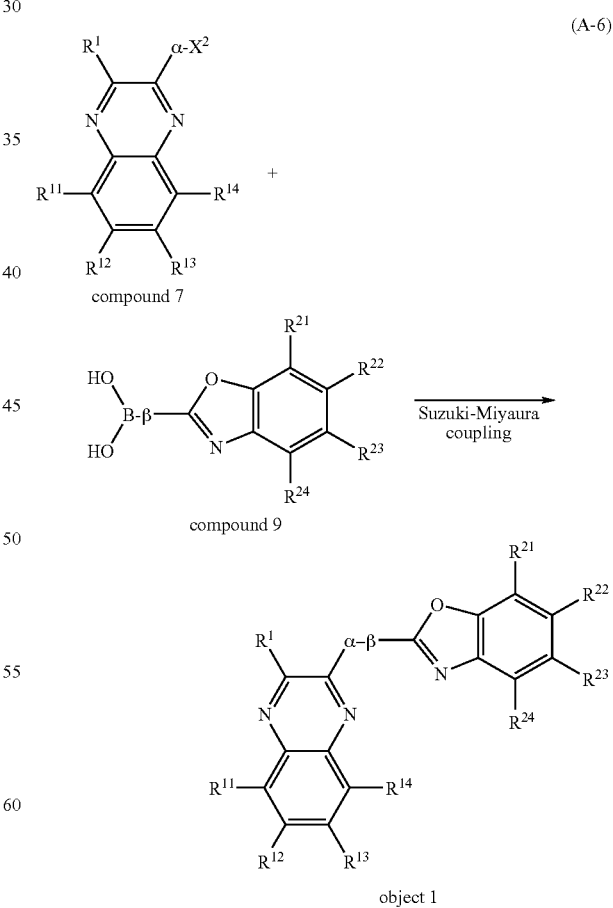

As shown in a synthesis scheme (A-6), the quinoxaline derivative (the compound 7) and the boronic acid of the 2-arylbenzoxazole derivative (the compound 9) are coupled by Suzuki-Miyaura Coupling using a palladium catalyst, so that the 2-arylbenzoxazole-substituted quinoxaline derivative (the object 1) can also be obtained. In the synthesis scheme (A-6), $R^1$ represents an alkyl group having 1 to 4 carbon atoms or an aryl group having 6 to 13 carbon atoms; $R^{11}$ to $R^{14}$ may be the same or different from each other and each represent any of hydrogen, an alkyl group having 1 to 4 carbon atoms, or a substituted or unsubstituted aryl group having 6 to 13 carbon atoms; and $R^{21}$ to $R^{24}$ may be the same or different from each other and each represent hydrogen or an alkyl group having 1 to 4 carbon atoms. Further, $X^2$ represents halogen or a triflate group; α represents an arylene group having 6 to 13 carbon atoms; and β represents an arylene group having 6 to 13 carbon atoms. When $X^2$ is halogen, chlorine, bromine, or iodine is preferable, and in particular, bromine or iodine is more preferable. In the synthesis scheme (A-6), as the palladium catalyst that can be used, palladium (II) acetate, tetrakis(triphenylphosphine)palladium(0), bis (triphenylphosphine)palladium(II) dichloride, or the like can be given. In the synthesis scheme (A-6), as a ligand of the palladium catalyst that can be used, tri(ortho-tolyl)phosphine, triphenylphosphine, tricyclohexylphosphine, or the like can be given. In the synthesis scheme (A-6), as a base that can be used, an organic base such as sodium tert-butoxide, an inorganic base such as potassium carbonate, or the like can be given. In the synthesis scheme (A-6), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. In the synthesis scheme (A-6), instead of the compound 9, an organoboron compound may be used, which is obtained by protecting the boronic acid of the compound 9 by ethyl alcohol, propyl alcohol, or the like. Alternatively, an organoboron compound which forms a ring may be used, which is obtained by protecting the boronic acid of the compound 9 by diol like ethylene glycol or pinacol. Further, instead of Suzuki-Miyaura Coupling, Cross Coupling Reaction using an organoaluminum compound, an organozirconium compound, an organozinc compound, an organotin compound, or the like may be used.

<Synthesis Method of Compound Represented by General Formula (G21)>

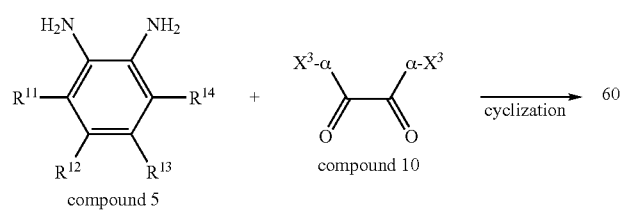

(A-7)

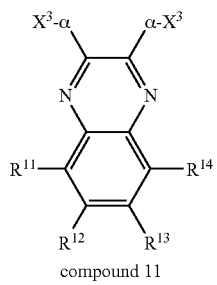

compound 11

First, as shown in a synthesis scheme (A-7), the 1,2-phenylenediamine derivative (the compound 5) which may include a substituent and a diketone derivative (a compound 10) are subjected to cyclodehydration, whereby a quinoxaline derivative (a compound 11) can be obtained. In the synthesis scheme (A-7), $R^{11}$ to $R^{14}$ may be the same or different from each other and each represent any of haydrogen, an alkyl group having 1 to 4 carbon atoms, or an aryl group having 6 to 13 carbon atoms. Further, $X^3$ represents halogen or a triflate group. When $X^3$ is halogen, chlorine, bromine, or iodine is preferable. In the synthesis scheme (A-7), as a solvent that can be used, a halogen-based solvent such as dichloromethane, chloroform, or carbon tetrachloride, alcohols such as ethanol, methanol, or isopropanol, acetic acid, a sodium carbonate aqueous solution, a sodium hydrogensulfate aqueous solution, a sodium acetate aqueous solution, a mixed solvent of sodium acetate aqueous solution and acetic acid, or the like can be given. Further, in a case where the halogen-based solvent is used, chloroform having the higher boiling point or carbon tetrachloride is preferably used.

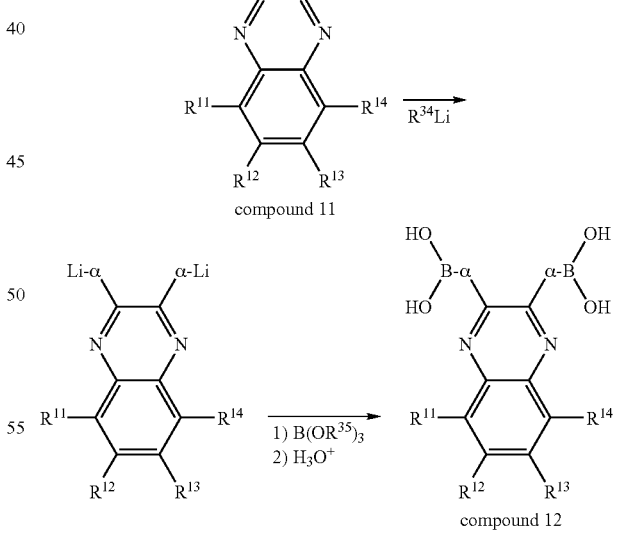

(A-8)

Next, as shown in a synthesis scheme (A-8), the quinoxaline derivative (the compound 11) is lithiated with use of an alkyl lithium reagent and hydrolyzed with acid or water using a boron reagent, whereby a boronic acid of the quinoxaline derivative (a compound 12) can be obtained. In the synthesis scheme (A-8), α represents an arylene group having 6 to 13 carbon atoms; $R^{11}$ to $R^{14}$ each represent any of hydrogen, an alkyl group having 1 to 4 carbon atoms, or an aryl group having 6 to 13 carbon atoms; $R^{34}$ represents an alkyl group having 1 to 6 carbon atoms; and $R^{35}$ represents an alkyl group having 1 to 6 carbon atoms. Further, $X^3$ represents halogen. In the synthesis scheme (A-8), as a solvent that can be used, an ether-based solvent such as diethyl ether, tetrahydrofuran (THF), or cyclopentyl methyl ether can be given. As an alkyl lithium reagent, n-butyllithium, tert-butyllithium, methyl lithium, or the like can be given when $R^{34}$ is an n-butyl group, a tert-butyl group, a methyl group, or the like, respectively. As a boron reagent, trimethyl borate, triisopropyl borate, or the like can be given when $R^{35}$ is a methyl group, an isopropyl group, or the like, respectively. Further, the boronic acid obtained by the synthesis scheme (A-8) may be protected by ethyl alcohol, propyl alcohol, or the like to form an organoboron compound or may be protected by diol like ethylene glycol or pinacol to form an organoboron compound which forms a ring.

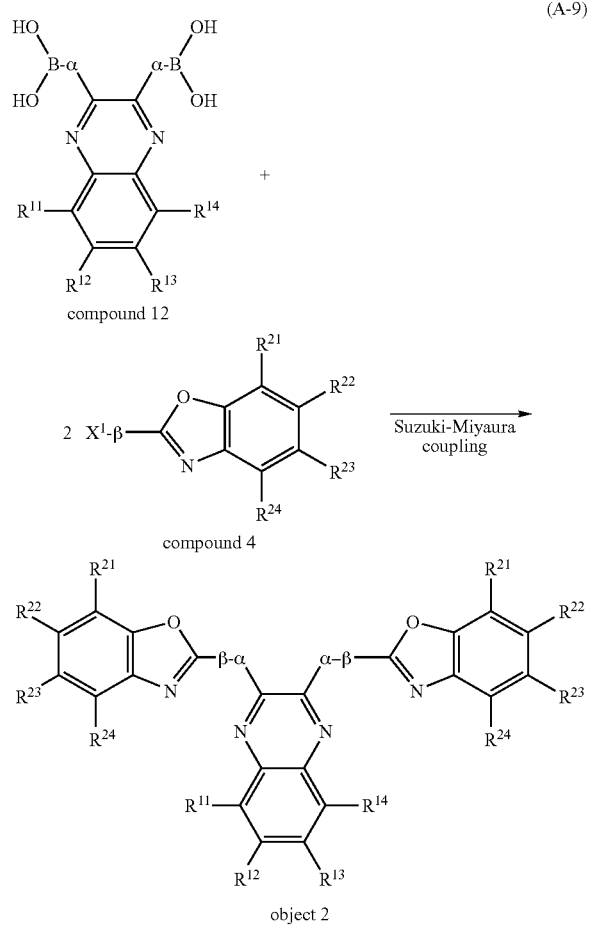

other and each represent hydrogen or an alkyl group having 1 to 4 carbon atoms. Further, $X^1$ represents halogen or a triflate group; α represents an arylene group having 6 to 13 carbon atoms; and β represents an arylene group having 6 to 13 carbon atoms. When $X^1$ is halogen, chlorine, bromine, or iodine is preferable, and in particular, bromine or iodine is more preferable. In the synthesis scheme (A-9), as the palladium catalyst that can be used, palladium(II) acetate, tetrakis(triphenylphosphine)palladium(0), bis(triphenylphosphine)palladium(II) dichloride, or the like can be given. In the synthesis scheme (A-9), as a ligand of the palladium catalyst that can be used, tri(ortho-tolyl)phosphine, triphenylphosphine, tricyclohexylphosphine, or the like can be given. In the synthesis scheme (A-9), as a base that can be used, an organic base such as sodium tert-butoxide, an inorganic base such as potassium carbonate, or the like can be given. In the synthesis scheme (A-9), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. In the synthesis scheme (A-9), instead of the compound 12, an organoboron compound may be used, which is obtained by protecting the boronic acid of the compound 12 by ethyl alcohol, propyl alcohol, or the like. Alternatively, an organoboron compound which forms a ring may be used, which is obtained by protecting the boronic acid of the compound 12 by diol like ethylene glycol or pinacol. Further, instead of Suzuki-Miyaura Coupling, Cross Coupling Reaction using an organoaluminum compound, an organozirconium compound, an organozinc compound, an organotin compound, or the like may be used.

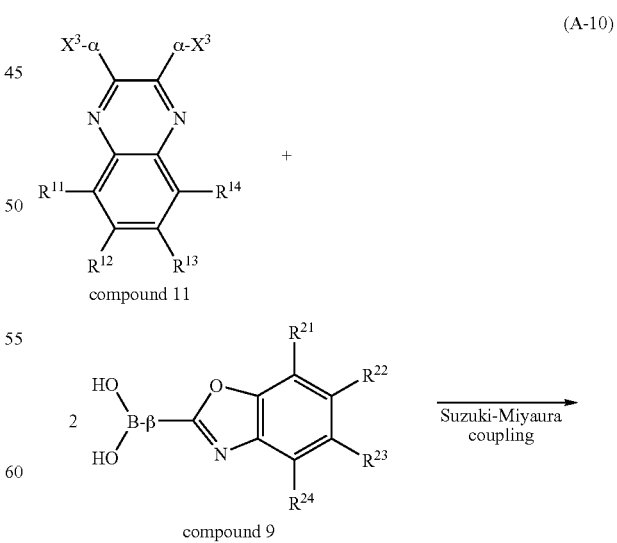

Next, as shown in a synthesis scheme (A-9), the boronic acid of the quinoxaline derivative (the compound 12) and the 2-arylbenzoxazole derivative (the compound 4) are coupled by Suzuki-Miyaura Coupling using a palladium catalyst, so that a quinoxaline derivative (an object 2) of a target can be obtained. In the synthesis scheme (A-9), $R^{11}$ to $R^{14}$ may be the same or different from each other and each represent any of hydrogen, an alkyl group having 1 to 4 carbon atoms, or a substituted or unsubstituted aryl group having 6 to 13 carbon atoms; and $R^{21}$ to $R^{24}$ may be the same or different from each

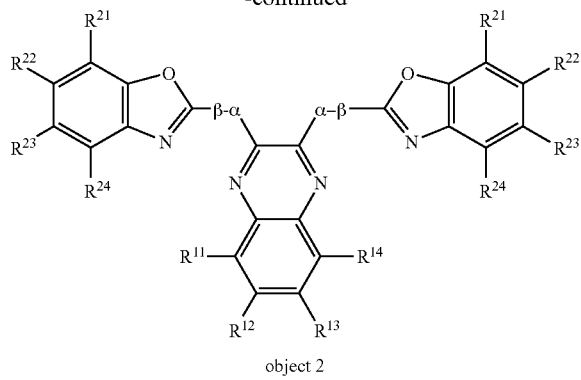

object 2

As shown in a synthesis scheme (A-10), the quinoxaline derivative (the compound 11) and the boronic acid of the benzoxazole derivative (the compound 9) are coupled by Suzuki-Miyaura Coupling using a palladium catalyst, whereby the quinoxaline derivative (the object 2) can also be obtained. In the synthesis scheme (A-10), $R^{11}$ to $R^{14}$ each represent any of hydrogen, an alkyl group having 1 to 4 carbon atoms, or an aryl group having 6 to 13 carbon atoms; and $R^{21}$ to $R^{24}$ each represent hydrogen or an alkyl group having 1 to 4 carbon atoms. $X^3$ represents halogen or a triflate group; α represents an arylene group having 6 to 13 carbon atoms; and β represents an arylene group having 6 to 13 carbon atoms. When $X^3$ is halogen, chlorine, bromine, or iodine is preferable, and in particular, bromine or iodine is more preferable. In the synthesis scheme (A-10), as the palladium catalyst that can be used, palladium(II) acetate, tetrakis(triphenylphosphine)palladium(0), bis(triphenylphosphine)palladium(II) dichloride, or the like can be given. In the synthesis scheme (A-10), as a ligand of the palladium catalyst that can be used, tri(ortho-tolyl)phosphine, triphenylphosphine, tricyclohexylphosphine, or the like can be given. In the synthesis scheme (A-10), as a base that can be used, an organic base such as sodium tert-butoxide, an inorganic base such as potassium carbonate, or the like can be given. In the synthesis scheme (A-10), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. In the synthesis scheme (A-10), instead of the compound 9, an organoboron compound may be used, which is obtained by protecting the boronic acid of the compound 9 by ethyl alcohol, propyl alcohol, or the like. Alternatively, an organoboron compound which forms a ring may be used, which is obtained by protecting the boronic acid of the compound 9 by diol like ethylene glycol or pinacol. Further, instead of Suzuki-Miyaura Coupling, Cross Coupling Reaction using an organoaluminum compound, an organozirconium compound, an organozinc compound, an organotin compound, or the like may be used.

The quinoxaline derivative of the present invention has a structure in which one of carbon at a 2-position and carbon at a 3-position of quinoxaline is bound to carbon at a 2-position of benzoxazole via an arylene group. Since a quinoxaline skeleton has an electron transporting property and a benzoxazole skeleton also has an electron transporting property, when at least one of carbon at a 2-position and carbon at a 3-position of quinoxaline is bound to carbon at a 2-position of benzoxazole via an arylene group, a quinoxaline derivative having an excellent electron transporting property can be obtained.

A quinoxaline derivative in which both carbon at a 2-position and carbon at a 3-position of quinoxaline are bound to carbon at a 2-position of benzoxazole via an arylene group has higher molecular weight and more improved thermo physical property than the quinoxaline derivative in which one of carbon at a 2-position and carbon at a 3-position of quinoxaline is bound to carbon at a 2-position of benzoxazole via an arylene group. In addition, since the thermo physical property is improved, improvement in stability of a film quality (suppression of crystallization) can be expected.

Further, the quinoxaline derivative of the present invention has an excellent electron transporting property. Therefore, by using the quinoxaline derivative of the present invention for an electronic device such as a light-emitting element or an organic transistor, favorable electrical characteristics can be obtained.

Embodiment Mode 2

In this embodiment mode, modes of light-emitting elements using any of the quinoxaline derivative shown in Embodiment Mode 1 will be described with reference to FIG. 1 and FIG. 2.

A light-emitting element of the present invention has a plurality of layers between a pair of electrodes. The plurality of layers are formed by combining and stacking a layer formed of a substance with a high carrier-injecting property and a layer formed of a substance with a high carrier-transporting property so that a light-emitting region can be formed in a region away from the electrodes, i.e., so that carriers can be recombined in an area away from the electrodes.

In this embodiment mode, the light-emitting element includes a first electrode 102, a second electrode 104, and an EL layer 103 formed between the first electrode 102 and the second electrode 104. Note that in this embodiment mode, description will be made below in such conditions that the first electrode 102 functions as an anode and the second electrode 104 functions as a cathode. In other words, when voltage is applied to the first electrode 102 and the second electrode 104 such that potential of the first electrode 102 is higher than that of the second electrode 104, light emission can be obtained. Such a case will be described below.

A substrate 101 is used as a support of the light-emitting element. The substrate 101 can be formed of, for example, glass, plastic, metal, or the like. Note that materials other than glass, plastic, or metal can be used as long as they can function as a support of a light-emitting element. Note that in the case where light from the light-emitting element is extracted outside through the substrate, it is preferable to use a light-transmitting substrate as the substrate 101.

As for the first electrode 102, a metal, an alloy, a conductive compound, a mixture thereof, or the like having a high work function (specifically, preferably 4.0 eV or higher) is preferably used. For example, indium tin oxide (ITO), indium tin oxide containing silicon or silicon oxide, indium zinc oxide (IZO), indium oxide containing tungsten oxide and zinc oxide (IWZO), and the like can be given. A film of such a conductive metal oxide is generally formed by sputtering, but may also be formed by an inkjet method, a spin coating method, or the like by application of a sol-gel method or the like. For example, a film of indium zinc oxide (IZO) can be formed by a sputtering method using a target in which zinc oxide is added into indium oxide at 1 to 20 wt %. In addition, a film of indium oxide containing tungsten oxide and zinc oxide (IWZO) can be formed by a sputtering method using a target in which tungsten oxide and zinc oxide are included in indium oxide at 0.5 to 5 wt % and at 0.1 to 1 wt %, respectively. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitride of a metal material (e.g., titanium nitride), and the like can be given.

In a case where a layer including a composite material described below is used as a layer in contact with the first electrode 102, a variety of metals, alloys, or electrically conductive compounds, a mixture thereof, or the like can be used for the first electrode 102 regardless of the work function. For example, aluminum (Al), silver (Ag), an alloy containing aluminum (AlSi), or the like can be used. Besides, any of the following materials with a low work function can be used for the first electrode 102: an element belonging to Group 1 or Group 2 of the periodic table, that is, an alkali metal such as lithium (Li) or cesium (Cs) or an alkaline earth metal such as magnesium (Mg), calcium (Ca), or strontium (Sr); an alloy thereof (MgAg, AlLi); a rare earth metal such as europium (Eu) or ytterbium (Yb); an alloy thereof; and the like. A film of an alkali metal, an alkaline earth metal, or an alloy thereof can be formed by a vacuum evaporation method. In addition, a film of an alloy containing an alkali metal or an alkaline earth metal can be formed by a sputtering method. Further, a film can be formed using a silver paste or the like by an inkjet method or the like.

The EL layer 103 shown in this embodiment mode includes a hole injecting layer 111, a hole transporting layer 112, a light-emitting layer 113, an electron transporting layer 114, and an electron injecting layer 115. Note that the stacked-layer structure of the EL layer 103 is not specifically limited as long as the EL layer 103 includes the quinoxaline derivative shown in Embodiment Mode 1. That is, there is no particular limitation on the stacked structure of the EL layer 103, and a quinoxaline derivative shown in Embodiment Mode 1 may be combined with a layer formed of a substance having a high electron transporting property, a substance having a high hole transporting property, a substance having a high electron injecting property, a substance having a high hole injecting property, a bipolar substance (a substance having high electron transporting and hole transporting properties), a substance having a high light-emitting property, or the like to form the EL layer 103. For example, the EL layer 103 can be formed by an appropriate combination of a hole injecting layer, a hole transporting layer, a light-emitting layer, an electron transporting layer, an electron injecting layer, and the like. Specific materials for each of the layers are given below.

The hole injecting layer 111 is a layer including a substance having a high hole injecting property. As a substance having a high hole injecting property, molybdenum oxide, vanadium oxide, ruthenium oxide, tungsten oxide, manganese oxide, or the like can be used. Besides, as a low molecular organic compound, a phthalocyanine-based compound such as phthalocyanine (abbreviation: $H_2Pc$), copper(II) phthalocyanine (abbreviation: CuPc), or vanadyl(IV) phthalocyanine (VOPc); an aromatic amine compound such as 4,4',4"-tris(N, N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1); or the like can be given.

Alternatively, for the hole injecting layer 111, a composite material in which an acceptor substance is mixed into a substance having a high hole transporting property can be used. Note that by using a material in which an acceptor substance is mixed into a substance having a high hole transporting property, a material for forming the electrode can be selected regardless of its work function. In other words, besides a material with a high work function, a material with a low work function may also be used as the first electrode 102. A composite material of those substances can be formed by co-evaporation of a substance having a high hole transporting property and an acceptor substance.

Note that in this specification, "composite" refers to not only a state where two materials are simply mixed but also a state where a plurality of materials are mixed so that charge can be given and received between the materials.

As an organic compound used for the composite material, a variety of compounds such as an aromatic amine compound, a carbazole derivative, an aromatic hydrocarbon, and a high molecular compound (oligomer, dendrimer, polymer, or the like) can be used. Note that the organic compound used for the composite material is preferably an organic compound having a high hole transporting property. Specifically, a substance having a hole mobility of $10^{-6}$ $cm^2/Vs$ or higher is preferably used. However, other substances may also be used as long as the hole transporting properties thereof are higher than the electron transporting properties thereof. Examples of an organic compound that can be used for the composite material are specifically listed below.

As the organic compound which can be used for the composite material, for example, an aromatic amine compound such as MTDATA, TDATA, DPAB, DNTPD, DPA3B, PCzPCA1 PCzPCA2, PCzPCN1, 4,4'-bis[N-(1-naphthyl)-N-phenylamino]biphenyl (abbreviation: NPB or α-NPD), or N,N'-bis(3-methylphenyl)-N,N'-diphenyl-[1,1'-biphenyl]-4, 4'-diamine (abbreviation: TPD); a carbazole derivative such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), or 1,4-bis[4-(N-carbazolyl)phenyl]-2,3,5,6-tetraphenylbenzene; or an aromatic hydrocarbon compound such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl) anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl) anthracene, 9,9'-bianthryl, 10, 10'-diphenyl-9,9'-bianthryl, 10,10'-bis(2-phenylphenyl)-9,9'-bianthryl, 10,10'-bis[(2,3,4, 5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), or 9,10-bis[4-(2,2-diphenylvinyl)phenyl]anthracene (abbreviation: DPVPA) can be given.

As the acceptor substance, an organic compound such as 7,7,8,8-tetracyano-2,3,5,6-tetrafluoroquinodimethane (abbreviation: $F_4$-TCNQ) or chloranil; or a transition metal oxide can be given. In addition, oxide of metals belonging to Group 4 to Group 8 of the periodic table can be given as the acceptor substance. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air and its hygroscopic property is low so that it can be easily handled.

Further, for the hole injecting layer 111, a high molecular compound (oligomer, dendrimer, polymer, or the like) can be used. For example, a high molecular compound such as poly (N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacryla mide] (abbreviation: PTPDMA), or poly[N,N'-bis(4-butylphenyl)-N,N'-bis(phenyl)benzidine (abbreviation: Poly-TPD) can be given. In addition, a high molecular compound to which acid is added can be used. As such a high molecular compound to which acid is added, poly(3,4-ethylenedioxythiophene)/poly(styrenesulfonic acid) (PEDOT/PSS), polyaniline/poly(styrenesulfonic acid) (PAni/PSS), or the like can be given.

Further, a composite material formed by using the above-mentioned high molecular compound such as PVK, PVTPA, PTPDMA, or Poly-TPD and the above-mentioned acceptor substance can be used for the hole injecting layer 111.

The hole transporting layer 112 is a layer including a substance having a high hole transporting property. As a substance having a high hole transporting property, an aromatic amine compound such as NPB (or α-NPD), TPD, 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), or the like can be given as the low molecular organic compound. The substances mentioned here mainly have a hole mobility of $10^{-6}$ cm$^2$/Vs or higher. However, other substances may also be used as long as the hole transporting properties thereof are higher than the electron transporting properties thereof. Note that the layer including a substance having a high hole transporting property is not limited to a single layer, but two or more layers including any of the above-mentioned substances may be stacked.

Further, for the hole transporting layer 112, a composite material in which an acceptor substance is contained in a substance having a high hole transporting property described above can be used.

Further, for the hole transporting layer 112, a high molecular compound such as PVK, PVTPA, PTPDMA, or Poly-TPD can be used.

The light-emitting layer 113 is a layer including a substance having a high light-emitting property, and a variety of materials can be used for the light-emitting layer. For example, as a substance having a high light-emitting property, a fluorescent compound which emits fluorescence or a phosphorescent compound which emits phosphorescence can be used.

As examples of a phosphorescent compound which is used for the light-emitting layer, an organometallic complex described below can be given. As a material for blue light emission, bis[2-(4',6'-difluorophenyl)pyridinato-N,C$^{2'}$]iridium(III)tetrakis(1-pyrazolyl)borate (abbreviation: FIr6), bis [2-(4',6'-difluorophenyl)pyridinato-N,C$^{2'}$]iridium(III)picolinate (abbreviation: FIrpic), bis[2-(3',5'bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III)acetylacetonate (abbreviation: FIr(acac)) or the like can be given. As a material for green light emission, tris(2-phenylpyridinato-N,C$^{2'}$) iridium(III) (abbreviation: Ir(ppy)$_3$), bis(2-phenylpyridinato-N,C$^{2'}$)iridium(III)(acetylacetonate) (abbreviation: Ir(ppy)$_2$ (acac)), bis(1,2-diphenyl-1H-benzimidazolato)iridium(III) acetylacetonate (abbreviation: Ir(pbi)$_2$(acac)), bis(benzo[h] quinolinato)iridium(III)acetylacetonate (abbreviation: Ir(bzq)$_2$(acac)) or the like can be given. As a material for yellow light emission, bis(2,4-diphenyl-1,3-oxazolato-N, C$^{2'}$)iridium(III)acetylacetonate (abbreviation: Ir(dpo)$_2$ (acac)), bis[2-(4'-perfluorophenylphenyl)pyridinato]iridium (III)acetylacetonate (abbreviation: Ir(p-PF-ph)$_2$(acac)), bis (2-phenylbenzothiazolato-N,C$^{2'}$)iridium(III)acetylacetonate (abbreviation: Ir(bt)$_2$(acac)) or the like can be given. As a material for orange light emission, tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)) or the like can be given. As a material for red light emission, an organometallic complex such as bis[2-(2'-benzo[4,5-α]thienyl)pyridinato-N,C$^{3'}$]iridium(acetylacetonate) (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl) quinoxalinato]iridium(III) (abbreviation: Ir(Fdpq)$_2$(acac)), or (2,3,7,8,12,13,17,18-octaethyl-21H,23H-porphyrinato) platinum(II) (abbreviation: PtOEP) can be given. In addition, a rare earth metal complex such as tris(acetylacetonato) (monophenanthroline)terbium(III) (abbreviation: Tb(acac)$_3$ (Phen)), tris(1,3-diphenyl-1,3-propanedionato) (monophenanthroline)europium(III) (abbreviation: Eu(DBM)$_3$(Phen)), or tris[1-(2-thenoyl)-3,3,3-trifluoroacetonato](monophenanthroline)europium(III) (abbreviation: Eu(TTA)$_3$(Phen)) performs light emission (electron transition between different multiplicities) from a rare earth metal ion; therefore, such a rare earth metal complex can be used as a phosphorescent compound.

Examples of a fluorescent compound which is used for the light-emitting layer are given below. As a material for blue light emission, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), or the like can be given. As a material for green light emission, N-(9,10-diphenyl-2-anthryl)-N,9-diphenyl-9H-carbazol-3-amine (abbreviation, 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N'N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N, 9-triphenylanthracen-9-amine (abbreviation: DPhAPhA), or the like can be given. As a material for yellow light emission, rubrene, 5,12-bis(1,1'-biphenyl-4-yl)-6,11-diphenyltetracene (abbreviation: BPT), or the like can be given. As a material for red light emission, N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-α]fluoranthene-3,10-d iamine (abbreviation: p-mPhAFD), or the like can be given.

Note that the light-emitting layer may have a structure in which any of the above substances having a high light-emitting property (guest material) is dispersed into another substance (host material). As a substance into which the substance having a light-emitting property is dispersed, various kinds of materials can be used, and it is preferable to use a substance whose lowest unoccupied molecular orbital (LUMO) level is higher than that of a substance having a light-emitting property and whose highest occupied molecular orbital (HOMO) level is lower than that of the substance having a light-emitting property.

As the substance into which the substance having a light-emitting property is dispersed, specifically, a metal complex such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ01), 2,2',2''-(1,3,5-benzenetriyl)tris(1-phenyl-1H-benzimidazole) (abbreviation: TPBI), bathophenanthroline (abbreviation: BPhen), or bathocuproine (BCP); a condensed aromatic compound such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), or 6,12-dimethoxy-5,11-diphenylchrysene; an aromatic amine compound such as N,N-dipheyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, or BSPB; or the like can be used.

As the substance into which the substance having a light-emitting property is dispersed, a plurality of kinds of substances can be used. For example, in order to suppress crystallization, a substance for suppressing crystallization such as rubrene or the like may be further added. Furthermore, in order to efficiently transfer energy to the substance having a light-emitting property, NPB, Alq, or the like may be further added.

When a structure in which the substance having a high light-emitting property is dispersed into another substance is employed, crystallization of the light-emitting layer 113 can be suppressed. Further, concentration quenching due to high concentration of the substance having a high light-emitting property can be suppressed.

Note that for the light-emitting layer 113, a high molecular compound can be used. Specifically, as a material for blue light emission, poly(9,9-dioctylfluorene-2,7-diyl) (abbreviation: POF), poly[(9,9-dioctylfluorene-2,7-diyl)-co-(2,5-dimethoxybenzene-1,4-diyl)](abbreviation: PF-DMOP), poly{(9,9-dioctylfluorene-2,7-diyl)-co-[N,N'-di-(p-butylphenyl)-1,4-diaminobenzene]}(abbreviation: TAB-PFH) or the like can be given. As a material for green light emission, poly(p-phenylenevinylene) (abbreviation: PPV), poly[(9,9-dihexylfluorene-2,7-diyl)-alt-co-(benzo[2,1,3]thiadiazole-4,7-diyl)](abbreviation: PFBT), poly[(9,9-dioctyl-2,7-divinylenefluorenylene)-alt-co-(2-methoxy-5-(2-ethylhexyloxy)-1, 4-phenylene)], or the like can be given. As a material for orange to red light emission, poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyla mino)-1,4-phenylene]}, poly{[2-methoxy-5-(2-ethylhexyloxy)-1,4-bis(1-cyanovinylenephenylene)]-alt-co-[2,5-bis(N,N'-diphenylamio)-1,4-phenylene]}(abbreviation: CN-PPV-DPD) or the like can be given.

The electron transporting layer 114 is a layer including a substance having a high electron transporting property. The quinoxaline derivative shown in Embodiment Mode 1 is superior in an electron transporting property; thus the quinoxaline derivative can be suitably used for the electron transporting layer 114. Note that the electron transporting layer is not limited to a single layer, and may be a stack of two or more layers.

In a case where the electron transporting layer has a stacked structure of two or more layers, as another substance having a high electron transporting property, for example, as a low molecular organic compound, a metal complex such as tris (8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ), can be used. Further, as an alternative to such a metal complex, a heterocyclic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ01), 2,2',2''-(1,3,5-benzenetriyl)tris(1-phenyl-1H-benzimidazole) (abbreviation: TPBI), bathophenanthroline (abbreviation: BPhen), or bathocuproine (abbreviation: BCP) can be used. The substances mentioned here mainly have an electron mobility of $10^{-6}$ cm$^2$/Vs or higher. Note that other substances than the substances mentioned above may also be used for the electron transporting layer as long as the electron transporting properties thereof are higher than the hole transporting properties thereof. Note that the electron transporting layer is not limited to a single layer, but two or more layers including the above-mentioned substances may be stacked.

In a case where the electron transporting layer has a stacked structure of two or more layers, as another substance having a high electron transporting property, a high molecular compound can be used. For example, poly[(9,9-dihexylfluorene-2,7-diyl)-co-(pyridine-3,5-diyl)](abbreviation: PF-Py), poly [(9,9-dioctyllfluorene-2,7-diyl)-co-(2,2'-bipyridine-6,6'-diyl)](abbreviation: PF-BPy), or the like can be used.

The electron injecting layer 115 is a layer including a substance having a high electron injecting property. As a substance having a high electron injecting property, an alkali metal such as lithium, an alkaline earth metal such as calcium, or a compound thereof such as lithium fluoride (LiF), cesium fluoride (CsF), or calcium fluoride ($CaF_2$) can be used. For example, a layer of a substance having an electron transporting property which further includes an alkali metal, an alkaline earth metal, or a compound thereof; for example, a layer of Alq including magnesium (Mg) can be used. Note that it is preferable to use the layer formed of a substance having an electron transporting property in which an alkali metal or an alkaline earth metal is mixed as the electron injecting layer because electrons can be efficiently injected from the second electrode 104.

As a substance for forming the second electrode 104, a metal, an alloy, an electrically conductive compound, a mixture thereof, or the like with a low work function (specifically, a work function of 3.8 eV or lower is preferable) can be used. Specific examples of such cathode materials are given as follows: an element belonging to Group 1 or Group 2 of the periodic table, that is, an alkali metal such as lithium (Li) or cesium (Cs) or an alkaline earth metal such as magnesium (Mg), calcium (Ca), or strontium (Sr); an alloy thereof (MgAg, AlLi); a rare earth metal such as europium (Eu) or ytterbium (Yb); an alloy thereof; or the like. A film of an alkali metal, an alkaline earth metal, or an alloy thereof can be formed by a vacuum evaporation method. In addition, a film of an alloy including an alkali metal or an alkaline earth metal can be formed by a sputtering method. Further, a film can be formed using a silver paste or the like by an inkjet method or the like.

By providing the electron injecting layer 115 which is a layer having a function of promoting electron injection between the second electrode 104 and the electron transporting layer 114, the second electrode 104 can be formed using a variety of conductive materials such as Al, Ag, ITO, or indium tin oxide containing silicon or silicon oxide, regardless of their work functions. A film of such a conductive material can be formed by a sputtering method, an inkjet method, a spin coating method, or the like.

Various methods can be used for forming an EL layer, regardless of a dry method or a wet method. For example, a vacuum evaporation method, an inkjet method, a spin coating method, or the like may be used. As described above, an EL layer is generally formed of a hole injecting layer, a hole transporting layer, a light-emitting layer, an electron transporting layer, an electron injecting layer, and the like. In forming the layers, film formation methods which are suitable for materials for forming the layers are preferably used, but one common film formation method can be used. Note that in forming each electrode, a similar method can also be employed as described above.

For example, the light-emitting layer and the like in the EL layer may be formed by a wet method using a high molecular compound selected from the above-mentioned materials. Further, the light-emitting layer and the like in the EL layer can also be formed by a wet method using a low molecular organic compound. Furthermore, the light-emitting layer and the like in the EL layer may be formed by a dry method such as a vacuum evaporation method using a low molecular organic compound.

The electrode may be formed by a wet method using a sol-gel method, or by a wet method using a paste of a metal material. Further, the electrode may be formed by a dry method such as a sputtering method or a vacuum evaporation method.

For example, in a case where a light-emitting element of the present invention is applied to a display device and the display device is manufactured using a large-sized substrate, it is preferable to form the light-emitting layer by a wet method. When the light-emitting layer is formed by an inkjet method, it becomes easy to apply different colors separately for the light-emitting layer even when a large-sized substrate is used.

In a light-emitting element of the present invention having the above-described structure, current flows due to a potential difference generated between the first electrode 102 and the second electrode 104, whereby holes and electrons are recombined in the EL layer 103 and light emission is obtained.

Light emission is extracted to the outside through either the first electrode 102 or the second electrode 104 or the both. Accordingly, either the first electrode 102 or the second electrode 104 or the both is/are an electrode having a light-transmitting property. For example, when only the first electrode 102 has a light-transmitting property, light emission is extracted from the substrate side through the first electrode 102. Alternatively, when only the second electrode 104 has a light-transmitting property, light emission is extracted from the opposite side to the substrate through the second electrode 104. When both the first electrode 102 and the second electrode 104 have a light-transmitting property, light emission is extracted from both the substrate side and the opposite side to the substrate through the first electrode 102 and the second electrode 104.

Note that the structure of the layers provided between the first electrode 102 and the second electrode 104 is not limited to the above structure. Any structure other than the above structure can be employed as long as a light-emitting region for recombination of holes and electrons is positioned away from the first electrode 102 and the second electrode 104 so as to prevent quenching caused by proximity of the light-emitting region to metal, and the quinoxaline derivative shown in Embodiment Mode 1 is provided.

That is, there is no particular limitation on the stacked structure of the layers, and the quinoxaline derivative shown in Embodiment Mode 1 may be combined with a layer formed of a substance having a high electron transporting property, a substance having a high hole transporting property, a substance having a high electron injecting property, a substance having a high hole injecting property, a bipolar substance (a substance having high electron transporting and hole transporting properties), or the like.

Figure 2:
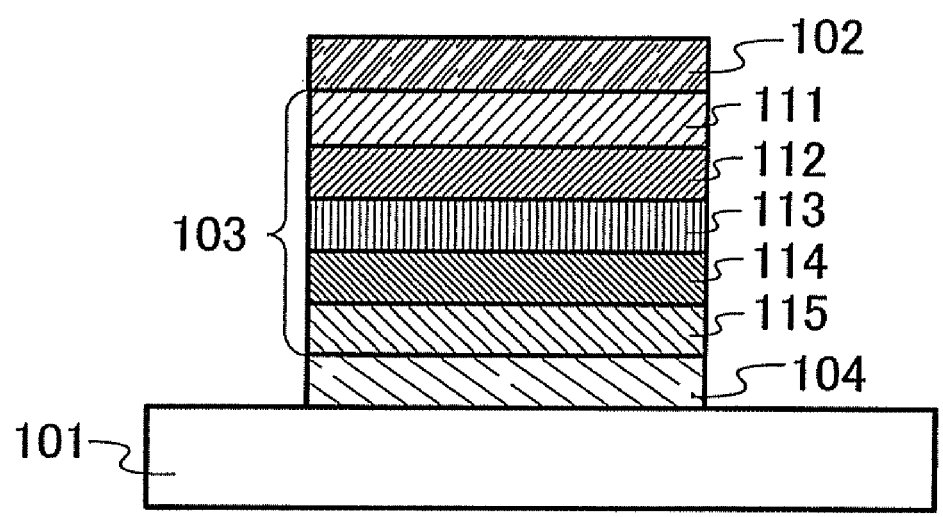
FIG. 2 illustrates a light-emitting element according to an aspect of the present invention.

In addition, as illustrated in FIG. 2, a structure in which the second electrode 104 serving as a cathode, the EL layer 103, and the first electrode 102 serving as an anode are stacked sequentially over the substrate 101 may be employed. In FIG. 2, a structure in which the electron injecting layer 115, the electron transporting layer 114, the light-emitting layer 113, the hole transporting layer 112, and the hole injecting layer 111 are stacked sequentially over the second electrode 104 is employed.

Note that in this embodiment mode, the light-emitting element is formed over a substrate made of glass, plastic, or the like. By forming a plurality of such light-emitting elements over a substrate, a passive matrix light-emitting device can be manufactured. Moreover, for example, thin film transistors (TFTs) may be formed over a substrate made of glass, plastic, or the like and light-emitting elements may be manufactured over electrodes which are electrically connected to the TFTs. Thus, an active matrix light-emitting device which controls the driving of a light-emitting element by a TFT can be manufactured. Note that a structure of the TFT is not particularly limited, and either a staggered TFT or an inverted staggered TFT may be used. In addition, a driving circuit formed over a TFT substrate may be formed using an N-channel TFT and a P-channel TFT, or may be formed using either an N-channel TFT or a P-channel TFT. In addition, the crystallinity of a semiconductor film used for the TFT is not particularly limited. Either an amorphous semiconductor film or a crystalline semiconductor film may be used for the TFT. Further, a single crystal semiconductor film may be used. A single crystal semiconductor film can be formed by a Smart Cut method or the like.

Since the quinoxaline derivative shown in Embodiment Mode 1 has an excellent electron transporting property, the quinoxaline derivative can be used preferably for an electron transporting layer of the light-emitting element. By using the quinoxaline derivative shown in Embodiment Mode 1, a light-emitting element with low driving voltage and with less power consumption can be obtained.

Note that this embodiment mode can be appropriately combined with another embodiment mode.

Embodiment Mode 3

In this embodiment mode, a structure in which the quinoxaline derivative shown in Embodiment Mode 1 is used for a light-emitting layer is shown as one mode of a light-emitting element of the present invention.

Since the quinoxaline derivative shown in Embodiment Mode 1 has an excellent electron transporting property, the quinoxaline derivative can be used as a host material in a light-emitting layer having a structure in which a substance with a high light-emitting property (guest material) is dispersed in another substance (host material).

In the case where the quinoxaline derivative shown in Embodiment Mode 1 is used as a host material and where a guest material emits fluorescence, it is preferable to use, as a guest material, a substance whose lowest unoccupied molecular orbital (LUMO) level is lower than that of the quinoxaline derivative show in Embodiment Mode 1 and whose highest occupied molecular orbital (HOMO) level is higher than that of the quinoxaline derivative shown in Embodiment Mode 1. For example, the following can be given as a material emitting blue light: N,N'-bis[4-(9H-carbazol-9-yl)phenyl]-N,N'-diphenylstilbene-4,4'-diamine (abbreviation: YGA2S); 4-(9H-carbazol-9-yl)-4'-(10-phenyl-9-anthryl)triphenylamine (abbreviation: YGAPA); or the like. Further, the following can be given as a material emitting green light: N-(9,10-diphenyl-2-anthryl)-N,9-diphenyl-9H-carbazol-3-amine (abbreviation: 2PCAPA); N-[9,10-bis(1, 1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine (abbreviation: 2DPAPA); N-[9,10-bis(1,1'-biphenyl-2-yl)-2-anthryl]-N,N',N'-triphenyl-1,4-phenylenediamine (abbreviation: 2DPABPhA); N-[9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); or the like. Further, the following can be given as a material emitting yellow or yellowish light: rubrene; 5,12-bis(1,1'-biphenyl-4-yl)-6,11-diphenyltetracene (abbreviation: BPT); or the like. Further, the following can be given as a material emitting red light: N,N,N',N'-tetrakis(4-methylphenyl)tetracene-5,11-diamine (abbreviation: p-mPhTD); 7,13-diphenyl-N,N,N',N'-tetrakis (4-methylphenyl)acenaphtho[1,2-a]fluoranthene-3,10-d iamine (abbreviation: p-mPhAFD); or the like.

Alternatively, in the case where the quinoxaline derivative shown in Embodiment Mode 1 is used as a host material and where a guest material emits phosphorescence, it is preferable to use a substance, as a guest material, having lower triplet excitation energy than that of the quinoxaline derivative shown in Embodiment Mode 1. For example, an organometallic complex can be given, such as bis[2-(2'-benzo[4,5-α] thienyl)pyridinato-N,$C^{3'}$]iridium(III)(acetylacetonate) (abbreviation: Ir(btp)$_2$(acac)), bis(1-phenylisoquinolinato-N, $C^{2'}$)iridium(III)acetylacetonate (abbreviation: Ir(piq)$_2$ (acac)), (acetylacetonato)bis[2,3-bis(4-fluorophenyl) quinoxalinato]iridium(III) (abbreviation: Ir(Fdpq)$_2$(acac)), or (2,3,7,8,12,13,17,18-octaethyl-21H,23H-porphyrinato) platinum(II) (abbreviation: PtOEP).

Since the quinoxaline derivative shown in Embodiment Mode 1 has an excellent electron transporting property, by using the quinoxaline derivative for a light-emitting layer, the light-emitting layer having a high electron transporting property can be obtained. Such a light-emitting layer can emit light with high efficiency when a guest material with high electron trapping property is used.

Plural kinds of substances can be used as a substance (a host material) for dispersing a light-emitting substance (a guest material). Thus, the light-emitting layer may include a second host material in addition to the quinoxaline derivative shown in Embodiment Mode 1. Since the quinoxaline derivative shown in Embodiment Mode 1 has an excellent electron transporting property, it is preferable to use a material having an excellent hole transporting property as the second host material. With such a structure, the light-emitting layer has a hole transporting property and an electron transporting property, and the recombination probability of holes and electrons in the light-emitting layer is increased, so that light emission with high efficiency can be obtained. Further, a light-emitting element with low driving voltage can be obtained.

Note that this embodiment can be appropriately combined with another embodiment mode.

Embodiment Mode 4

In this embodiment mode, a structure in which the quinoxaline derivative shown in Embodiment Mode 1 is used for an electron injecting layer is shown as one mode of a light-emitting element of the present invention.

Since the quinoxaline derivative shown in Embodiment Mode 1 can also have an excellent electron injecting property, the quinoxaline derivative can be used for an electron injecting layer. In the case where the quinoxaline derivative shown in Embodiment Mode 1 is used for an electron injecting layer, it is preferable to include an alkali metal, an alkaline earth metal, or a compound thereof in addition to the quinoxaline derivative shown in Embodiment Mode 1. With such a structure, an electron injecting property from an electrode functioning as a cathode is increased, and a light-emitting element with low driving voltage can be obtained.

Note that this embodiment mode can be appropriately combined with another embodiment mode.

Embodiment Mode 5

In this embodiment mode, a mode of a light-emitting element in which a plurality of light-emitting units according to the present invention are stacked (hereinafter this light-emitting element is referred to as a stacked-type element) will be described with reference to FIG. 3. This light-emitting element is a stacked-type light-emitting element including a plurality of light-emitting units between a first electrode and a second electrode. Each structure of the light-emitting units can be similar to the structure described in Embodiment Modes 2 to 4. In other words, the light-emitting element described in Embodiment Mode 2 is a light-emitting element having one light-emitting unit. In this embodiment mode, a light-emitting element having a plurality of light-emitting units will be described.

Figure 3:
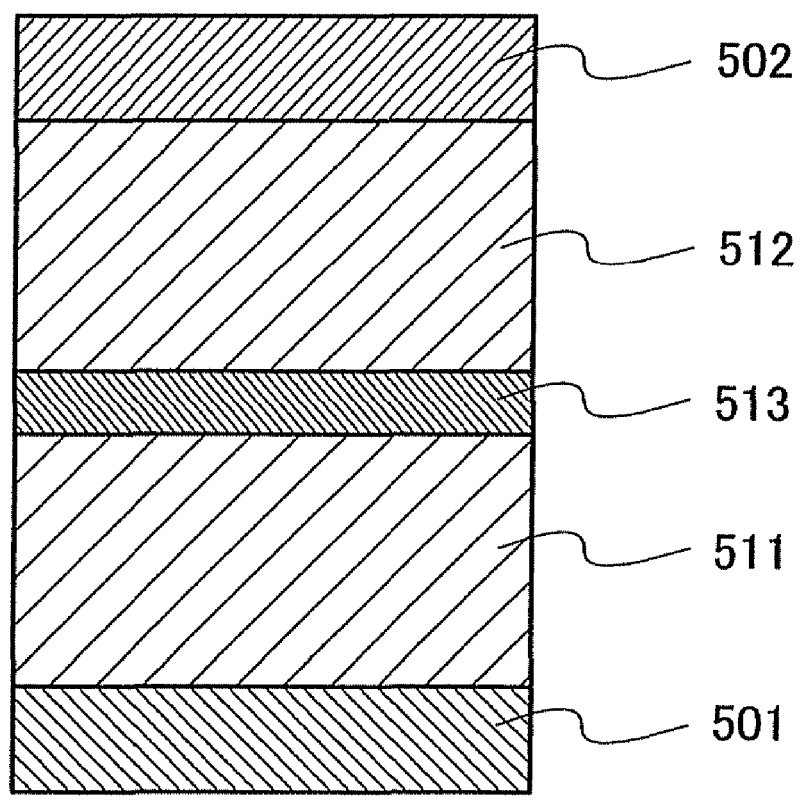
FIG. 3 illustrates a light-emitting element according to an aspect of the present invention.

In FIG. 3, a first light-emitting unit 511 and a second light-emitting unit 512 are stacked between a first electrode 501 and a second electrode 502. As the first electrode 501 and the second electrode 502, a similar electrode to the electrode shown in Embodiment Mode 2 can be employed. Note that the first light-emitting unit 511 and the second light-emitting unit 512 may have the same structure or different structures, and as the structures, a similar structure to the structure shown in Embodiment Mode 2 can be employed.

A charge generation layer 513 is a layer which injects electrons into a light-emitting unit on one side and injects holes into a light-emitting unit on the other side when voltage is applied to the first electrode 501 and the second electrode 502, and may be either a single layer or a stacked structure of two or more layers. As a stacked structure of two or more layers, a structure in which a hole injecting layer and an electron injecting layer are stacked is preferable.

As the hole injecting layer, a semiconductor or an insulator, such as molybdenum oxide, vanadium oxide, rhenium oxide, or ruthenium oxide, can be used. Alternatively, the hole injecting layer may have a structure in which an acceptor substance is added to a substance having a high hole transporting property. The layer including a substance having a high hole transporting property and an acceptor substance is formed of a composite material shown in Embodiment Mode 2, and includes as an acceptor substance, 7,7,8,8-tetracyano-2,3,5,6-tetrafluoroquinodimethane (abbreviation: $F_4$-TCNQ), metal oxide such as vanadium oxide, molybdenum oxide, tungsten oxide, or the like. As the substance having a high hole transporting property, various compounds such as an aromatic amine compound, a carbazole derivative, an aromatic hydrocarbon, or a high-molecular compound (oligomer, dendrimer, polymer, or the like) can be used. Note that a substance having a hole mobility of $10^{-6}$ cm$^2$/Vs or higher is preferably employed as the substance having a high hole transporting property. However, other substances may also be used as long as the hole transporting properties thereof are higher than the electron transporting properties thereof. Since the composite material of the substance having a high hole transporting property and the acceptor substance is superior in a carrier-injecting property and a carrier-transporting property, low-voltage driving and low-current driving can be realized.

As the electron injecting layer, an insulator or a semiconductor, such as lithium oxide, lithium fluoride, or cesium carbonate, can be used. Alternatively, the electron injecting layer may have a structure in which a donor substance is added to a substance having a high electron transporting property. As the donor substance, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron transporting property, the materials shown in Embodiment Mode 2 can be used. Note that a substance having an electron mobility of $10^{-6}$ cm$^2$/Vs or higher is preferably employed as the substance having a high electron transporting property. However, other substances may also be used as long as the electron transporting properties thereof are higher than the hole transporting properties thereof. Since the composite material of the substance having a high electron transporting property and the donor substance is superior in a carrier-injecting property and a carrier-transporting property, low-voltage driving and low-current driving can be realized.

Further, electrode materials shown in Embodiment Mode 2 can be used for the charge generation layer 513. For example, the charge generation layer 513 may be formed with a combination of a layer including a substance having a hole transporting property and metal oxide, and a transparent conductive film. Note that a layer having a high light-transmitting property is preferably used as the charge generation layer in terms of light extraction efficiency.

In any case, it is acceptable as long as the charge generation layer 513 interposed between the first light-emitting unit 511 and the second light-emitting unit 512 injects electrons into a light-emitting unit on one side and injects holes into a light-emitting unit on the other side when voltage is applied to the first electrode 501 and the second electrode 502. For example, any structure is acceptable for the charge generation layer 513 as long as the charge generation layer 513 injects electrons and holes into the first light-emitting unit 511 and the second light-emitting unit 512, respectively in a case of applying voltage so that potential of the first electrode can be higher than potential of the second electrode.

Although the light-emitting element having two light-emitting units is described in this embodiment mode, a light-emitting element in which three or more light-emitting units are stacked can be employed in a similar way. Like the light-emitting element of this embodiment mode, a plurality of light-emitting units are disposed between a pair of electrodes so as to be partitioned with the charge generation layer, and accordingly, the element with a long lifetime in a high luminance region can be realized while keeping low current density. In a case where the light-emitting element is applied to lighting as an application example, voltage drop due to resistance of an electrode material can be reduced. Accordingly, light can be uniformly emitted in a large area. Moreover, a light-emitting device of less power consumption, which can be driven at low voltage, can be achieved.

The light-emitting units emit light of different colors from each other, thereby obtaining light emission of a desired color from the whole light-emitting element. For example, in a light-emitting element having two light-emitting units, by making the emission colors of the first light-emitting unit and the second light-emitting unit complementary colors, the light-emitting element which emits white light as the whole element can be obtained. Note that "complementary colors" refer to colors which can produce an achromatic color when mixed. That is, white light emission can be obtained by mixing light obtained from substances emitting light of complementary colors. The same can be applied to a light-emitting element having three light-emitting units. For example, when the first light-emitting unit emits red light, the second light-emitting unit emits green light, and the third light-emitting unit emits blue light, white light can be emitted from the whole light-emitting element.

Note that this embodiment mode can be appropriately combined with another embodiment mode.

Embodiment Mode 6

In this embodiment mode, a light-emitting device having a light-emitting element of the present invention will be described.

A light-emitting device having a light-emitting element of the present invention in a pixel portion is described in this embodiment mode with reference to FIGS. 4A and 4B. Note that FIG. 4A is a top view illustrating the light-emitting device and FIG. 4B is a cross-sectional view of FIG. 4A taken along lines A-A' and B-B'. This light-emitting device includes a driver circuit portion (source side driver circuit) 601, a pixel portion 602, and a driver circuit portion (gate side driver circuit) 603, which are indicated by dotted lines, in order to control the light emission of the light-emitting element. Further, reference numeral 604 indicates a sealing substrate and reference numeral 605 indicates a sealing material. A space 607 is provided on an inner side of a portion surrounded by the sealing material 605.

Note that a leading wiring 608 is a wiring for transmitting signals input in the source side driver circuit 601 and the gate side driver circuit 603. The leading wiring 608 receives video signals, clock signals, start signals, reset signals, and the like from an FPC (flexible printed circuit) 609 that serves as an external input terminal. Although only an FPC is illustrated here, this FPC may be provided with a printed wiring board (PWB). The light-emitting device in this specification includes not only a light-emitting device itself but also a light-emitting device with an FPC or a PWB attached thereto.

Then, a cross-sectional structure is described with reference to FIG. 4B. The driver circuit portions and the pixel portion are provided over an element substrate 610. In FIG. 4B, only the source side driver circuit 601, which is the driver circuit portion, and one pixel of the pixel portion 602 are illustrated.

Note that a CMOS circuit which is a combination of an N-channel TFT 623 and a P-channel TFT 624 is formed in the source side driver circuit 601. The driver circuit may be formed with various circuits such as CMOS circuits, PMOS circuits, or NMOS circuits. In this embodiment mode, a driver-integrated type in which a driver circuit is formed over the substrate provided with the pixel portion is described; however, the present invention is not limited to this, and the driver circuit can be formed outside the substrate.

The pixel portion 602 includes a plurality of pixels each having a switching TFT 611, a current controlling TFT 612, and a first electrode 613 that is electrically connected to a drain of the current controlling TFT 612. Note that an insulator 614 is formed to cover the edge portion of the first electrode 613. Here, a positive photosensitive acrylic resin film is used to form the insulator 614.

Further, in order to improve the coverage, the insulator 614 is provided such that either an upper edge portion or a lower edge portion of the insulator 614 has a curved surface with a curvature. For example, when positive photosensitive acrylic is used as a material for the insulator 614, it is preferable that only an upper edge portion of the insulator 614 have a curved surface with a radius of curvature (0.2 μm to 3 μm). The insulator 614 can be formed using either a negative type that becomes insoluble in an etchant by light irradiation or a positive type that becomes soluble in an etchant by light irradiation.

An EL layer 616 and a second electrode 617 are formed over the first electrode 613. Here, various metals, alloys, electrically conductive compounds, or mixtures thereof can be used for a material of the first electrode 613. If the first electrode is used as an anode, it is preferable that the first electrode be formed using a metal, an alloy, an electrically conductive compound, a mixture thereof with a high work function (preferably, a work function of 4.0 eV or higher) among such materials. For example, the first electrode 613 can be formed using a single-layer film such as an indium tin oxide film containing silicon, an indium zinc oxide film, a titanium nitride film, a chromium film, a tungsten film, a Zn film, a Pt film, or the like; a stacked film of a titanium nitride film and a film containing aluminum as its main component; or a three-layer structure of a titanium nitride film, a film containing aluminum as its main component, and a titanium nitride film. Note that when a stacked structure is employed, the first electrode 613 has low resistance as a wiring, forms a favorable ohmic contact, and can serve as an anode.

The EL layer 616 is formed by various methods such as an evaporation method using an evaporation mask, an inkjet method, a spin coating method, or the like. The EL layer 616 includes the layer for controlling the carrier transport shown in Embodiment Modes 2 to 5. Any of a low molecular compound or a high molecular compound (such as an oligomer or a dendrimer) may be employed as a material for the EL layer 616. As the material for the EL layer, not only an organic compound but also an inorganic compound may be used.

As the material for the second electrode 617, various types of metals, alloys, electrically conductive compounds, mixtures thereof, or the like can be used. If the second electrode is used as a cathode, it is preferable that the second electrode be formed using a metal, an alloy, an electrically conductive compound, a mixture thereof, or the like with a low work function (preferably, a work function of 3.8 eV or lower) among such materials. For example, an element belonging to Group 1 or Group 2 of the periodic table, that is, an alkali metal such as lithium (Li) or cesium (Cs) or an alkaline earth metal such as magnesium (Mg), calcium (Ca), or strontium (Sr); an alloy thereof (MgAg, AlLi); or the like can be given. In a case where light generated in the EL layer 616 is transmitted through the second electrode 617, the second electrode 617 may also be formed by using a stacked layer of a thin metal film with a reduced film thickness and a transparent conductive film (indium tin oxide (ITO), indium tin oxide containing silicon or silicon oxide, indium zinc oxide (IZO), indium oxide containing tungsten oxide and zinc oxide (IWZO), or the like).

By attaching the sealing substrate 604 to the element substrate 610 with the sealing material 605, a light-emitting element 618 is provided in the space 607 which is surrounded by the element substrate 610, the sealing substrate 604, and the sealing material 605. Note that the space 607 is filled with a filler. There are cases where the space 607 may be filled with an inert gas (such as nitrogen or argon) as such a filler, or where the space 607 may be filled with the sealing material 605.

As the sealing material 605, an epoxy-based resin is preferably used. In addition, it is desirable to use a material that allows permeation of moisture or oxygen as little as possible. As the sealing substrate 604, a plastic substrate formed of FRP (fiberglass-reinforced plastics), PVF (polyvinyl fluoride), polyester, acrylic, or the like can be used besides a glass substrate or a quartz substrate.

As described above, the light-emitting device including a light-emitting element of the present invention can be obtained.

A light-emitting device of the present invention includes any of the light-emitting elements shown in Embodiment Modes 2 to 5. Driving voltage of the light-emitting element shown in Embodiment Modes 2 to 5 is low; therefore, a light-emitting device with less power consumption can be obtained.

Figure 5A:
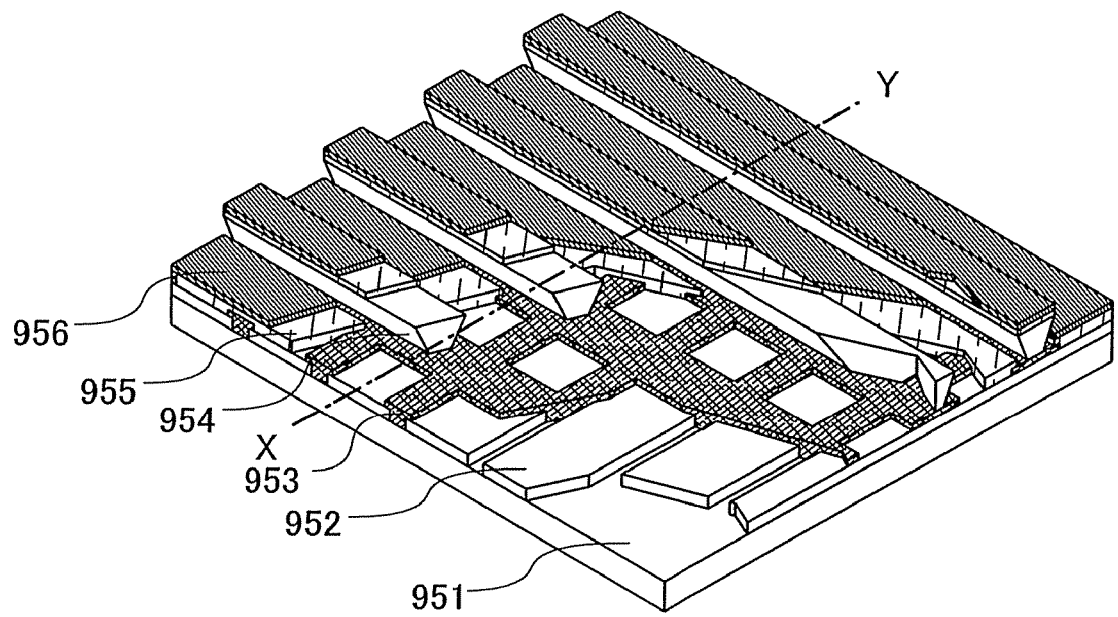
FIG. 5A is a perspective view illustrating a light-emitting device according to an aspect of the present invention and FIG. 5B is a cross-sectional view thereof.
Figure 5B:
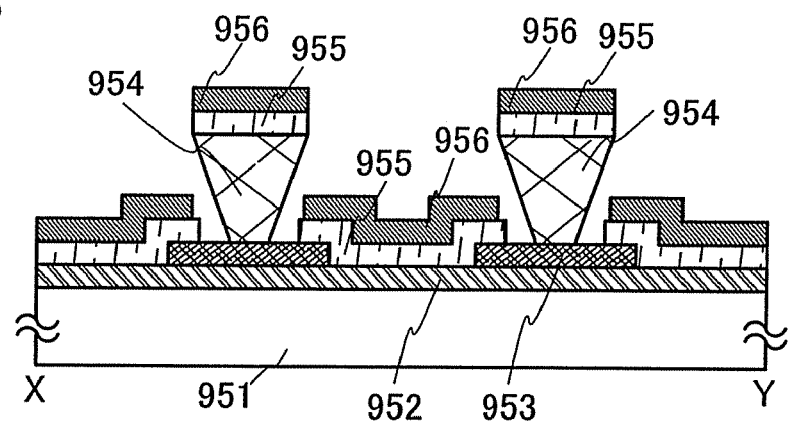

As described above, an active matrix light-emitting device that controls driving of a light-emitting element with a transistor is described in this embodiment mode; however, a passive matrix light-emitting device may be used. FIGS. 5A and 5B illustrate a passive matrix light-emitting device manufactured according to the present invention. Note that FIG. 5A is a perspective view of the light-emitting device and FIG. 5B is a cross-sectional view of FIG. 5A taken along a line X-Y In FIGS. 5A and 5B, an EL layer 955 is provided between an electrode 952 and an electrode 956 over a substrate 951. The edge portion of the electrode 952 is covered with an insulating layer 953. A partition layer 954 is provided over the insulating layer 953. The sidewalls of the partition layer 954 slope so that the distance between one sidewall and the other sidewall is gradually reduced toward the surface of the substrate. In other words, a cross section taken in the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other one of the pair of parallel sides). A cathode can be patterned by providing the partition layer 954 in this manner. In addition, in a passive matrix light-emitting device, a light-emitting device with less power consumption can be obtained by including a light-emitting element with low driving voltage according to the present invention.

Note that this embodiment mode can be appropriately combined with another embodiment mode.

Embodiment Mode 7

In this embodiment mode, an electronic device of the present invention which includes the light-emitting device shown in Embodiment Mode 6 will be described. An electronic device of the present invention includes any of the light-emitting elements described in Embodiment Modes 2 to 5, and a display portion with less power consumption.

As an electronic device manufactured using a light-emitting device of the present invention, cameras such as a video camera and a digital camera, a goggle type display, a navigation system, an audio reproducing device (a car audio set, an audio component set, or the like), a computer, a game machine, a portable information terminal (a mobile computer, a cellular phone, a portable game machine, an electronic book reader, or the like), an image reproducing device provided with a storage medium (specifically, a device provided with a display device that can reproduce a storage medium such as a digital versatile disc (DVD) and display the image), and the like can be given. Specific examples of these electronic devices are illustrated in FIGS. 6A to 6D.

Figure 6A:
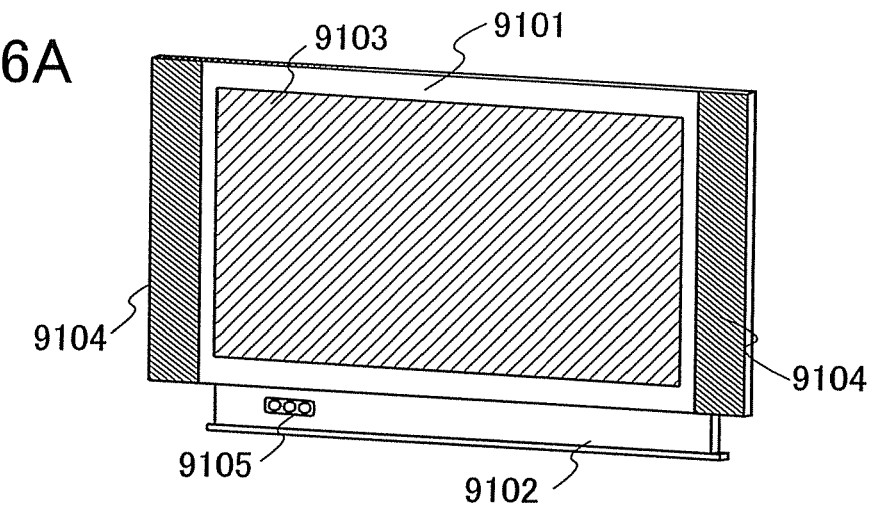
FIGS. 6A to 6D each illustrate an electronic device according to an aspect of the present invention

FIG. 6A illustrates a television device of this embodiment mode, which includes a housing 9101, a support 9102, a display portion 9103, speaker portions 9104, a video input terminal 9105, and the like. In the display portion 9103 of this television device, light-emitting elements similar to those described in Embodiment Modes 2 to 5 are arranged in matrix. Features of the light-emitting element are that driving voltage is low and power consumption is low. The display portion 9103 which includes the light-emitting element has similar features. Therefore, in this television device, less power consumption is achieved. With such features, a power supply circuit can be significantly reduced or downsized in the television device; therefore, reduction in size and weight of the housing 9101 and the support 9102 can be achieved. In the television device of this embodiment mode, less power consumption, and reduction in size and weight are achieved; therefore, a product which is suitable for living environment can be provided.

Figure 6B:
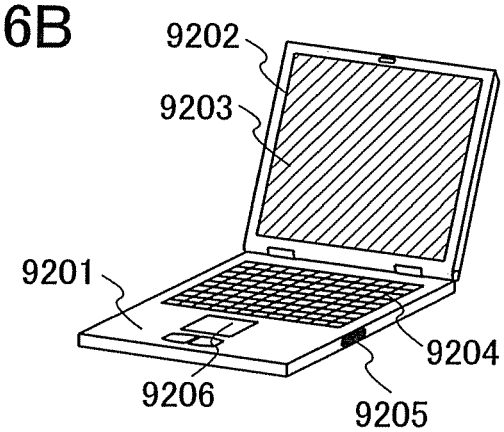

FIG. 6B illustrates a computer of this embodiment mode, which includes a main body 9201, a housing 9202, a display portion 9203, a keyboard 9204, an external connection port 9205, a pointing device 9206, and the like. In the display portion 9203 of this computer, light-emitting elements similar to those described in Embodiment Modes 2 to 5 are arranged in matrix. Features of the light-emitting element are that driving voltage is low and power consumption is low. The display portion 9203 which includes the light-emitting elements has similar features. Therefore, in the computer, less power consumption is achieved. With such features, a power supply circuit can be significantly reduced or downsized in the computer; therefore, reduction in size and weight of the main body 9201 and the housing 9202 can be achieved. In the computer of this embodiment mode, less power consumption, and reduction in size and weight are achieved; therefore, a product which is suitable for environment can be provided.

Figure 6C:
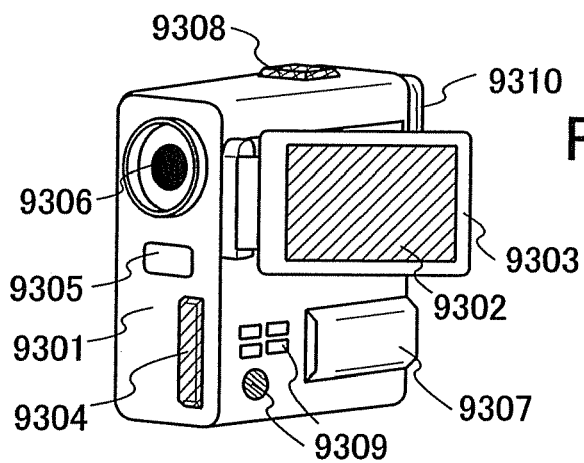

FIG. 6C illustrates a camera, which includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiment Modes 2 to 5 are arranged in matrix. Features of the light-emitting element are that driving voltage is low and power consumption is low. The display portion 9302 which includes the light-emitting elements has similar features. Therefore, in the camera, less power consumption is achieved. With such features, a power supply circuit can be significantly reduced or downsized in the camera; therefore, reduction in size and weight of the main body 9301 can be achieved. In the camera of this embodiment mode, less power consumption, and reduction in size and weight are achieved; therefore, a product which is suitable for being carried can be provided.

Figure 6D:
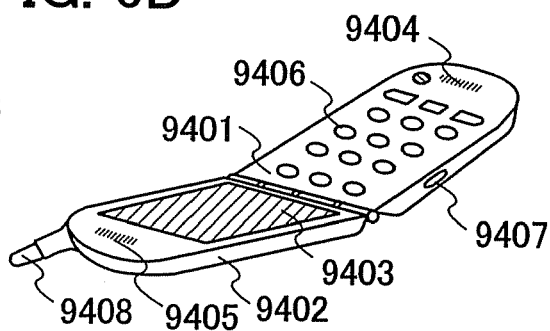

FIG. 6D illustrates a cellular phone of this embodiment mode, which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to those described in Embodiment Modes 2 to 5 are arranged in matrix. Features of the light-emitting element are that driving voltage is low and power consumption is low. The display portion 9403 which includes the light-emitting elements has similar features. Therefore, in the cellular phone, less power consumption is achieved. With such features, a power supply circuit can be significantly reduced or downsized in the cellular phone; therefore, reduction in size and weight of the main body 9401 and the housing 9402 can be achieved. In the cellular phone of this embodiment mode, less power consumption, and reduction in size and weight are achieved; therefore, a product which is suitable for being carried can be provided.

Figure 12A:
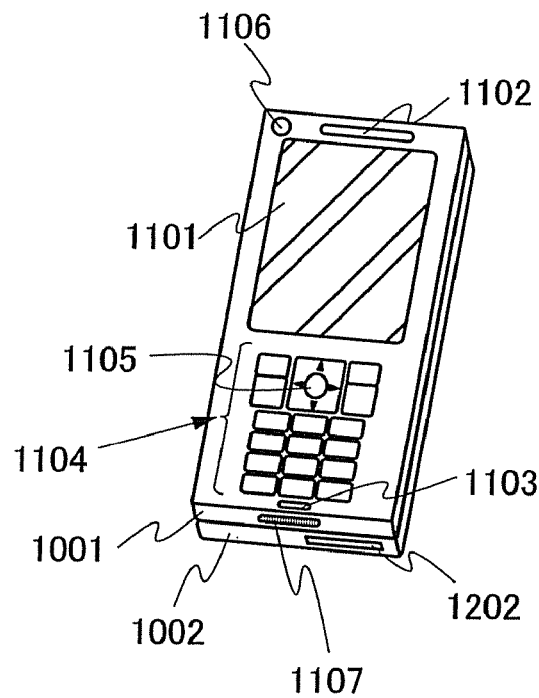
FIGS. 12A to 12C illustrate an electronic device according to an aspect of the present invention.
Figure 12B:
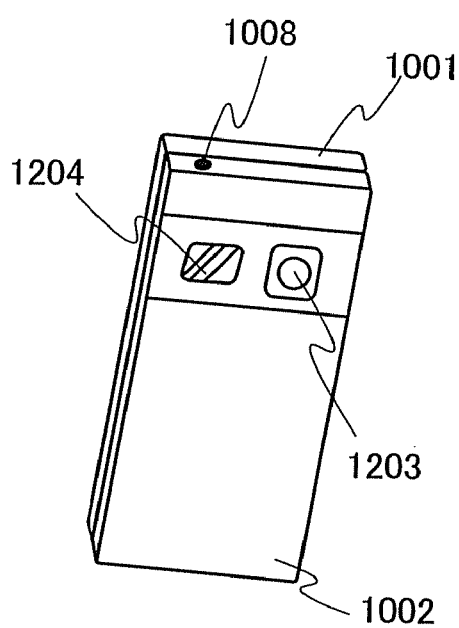
Figure 12C:
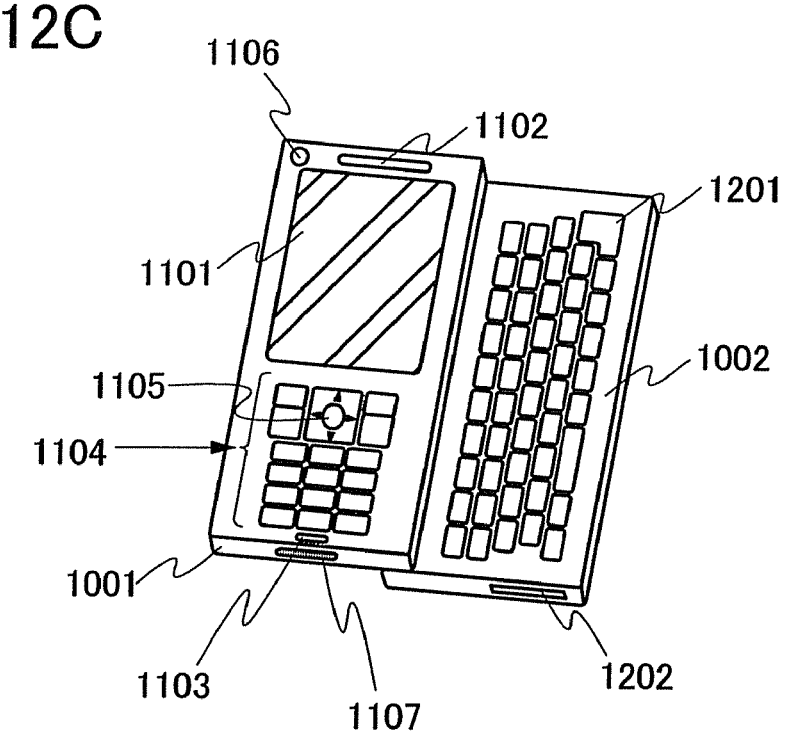

FIGS. 12A to 12C illustrate an example of a structure of a cellular phone, which is different from a structure of the cellular phone of FIG. 6D. FIG. 12A is a front view, FIG. 12B is a rear view, and FIG. 12C is a development view. The cellular phone in FIGS. 12A to 12C is a so-called smartphone which has both functions of a phone and a portable information terminal, and incorporates a computer to conduct a variety of data processing in addition to voice calls.

The cellular phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, an earphone terminal 1008, and the like, while the housing 1002 includes a keyboard 1201, an external memory slot 1202, a camera lens 1203, a light 1204, and the like. In addition, an antenna is incorporated in the housing 1001.

Further, in addition to the above structure, the cellular phone may incorporate a non-contact IC chip, a small-sized memory device, or the like.

In the display portion 1101, the light-emitting device shown in Embodiment Mode 6 can be incorporated, and a display direction can be appropriately changed depending on the usage mode. The cellular phone is provided with the camera lens 1106 on the same surface as the display portion 1101; therefore, the cellular phone can be used as a videophone. Further, a still image and a moving image can be taken with the camera lens 1203 and the light 1204 using the display portion 1101 as a viewfinder. The speaker 1102 and the microphone 1103 can be used for video calls, recording, reproducing, and the like without being limited to voice calls. With the use of the operation keys 1104, making and receiving calls, inputting simple information such as e-mail or the like, scrolling the screen, moving the cursor, and the like are possible. Furthermore, the housing 1001 and the housing 1002 (FIG. 12A), which are overlapped with each other, are developed by sliding as show in FIG. 12C, and can be used as a portable information terminal. In this case, smooth operation can be conducted using the keyboard 1201 and the pointing device 1105. The external connection terminal 1107 can be connected to an AC adaptor and various types of cables such as a USB cable, and charging, data communication with a computer, and the like are possible. Furthermore, a large amount of data can be stored and moved by inserting a storage medium into the external memory slot 1202.

Further, in addition to the above functions, the cellular phone may include an infrared communication function, a television receiving function, or the like.

Figure 7:
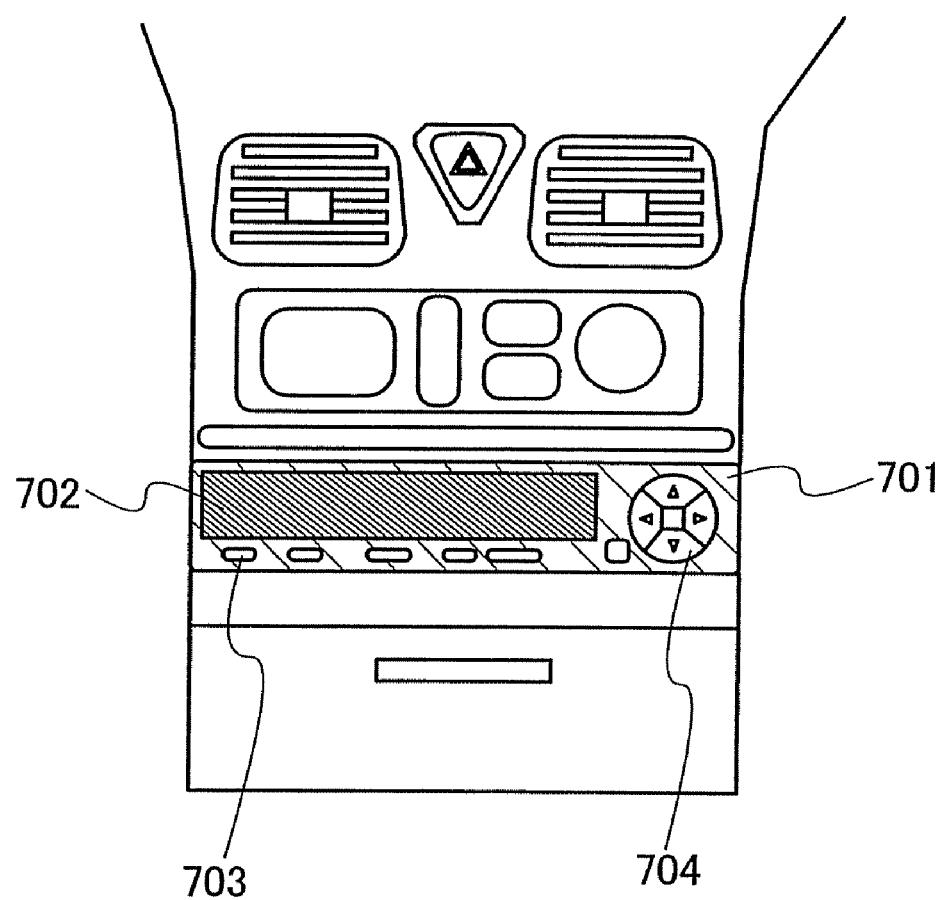
FIG. 7 illustrates an electronic device according to an aspect of the present invention

FIG. 7 illustrates an audio reproducing device, specifically, a car audio system, which includes a main body 701, a display portion 702, and operation switches 703 and 704. The display portion 702 can be realized with the light-emitting device (passive matrix type or active matrix type) described in Embodiment Mode 6. Further, the display portion 702 may be formed using a segment type light-emitting device. In any case, the use of a light-emitting element of the present invention makes it possible to form a bright display portion while achieving less power consumption, with the use of a vehicle power source (12 to 42 V). Further, although this embodiment mode describes an in-car audio system, a light-emitting device of the present invention may also be used in portable audio systems or audio systems for home use.

Figure 8:
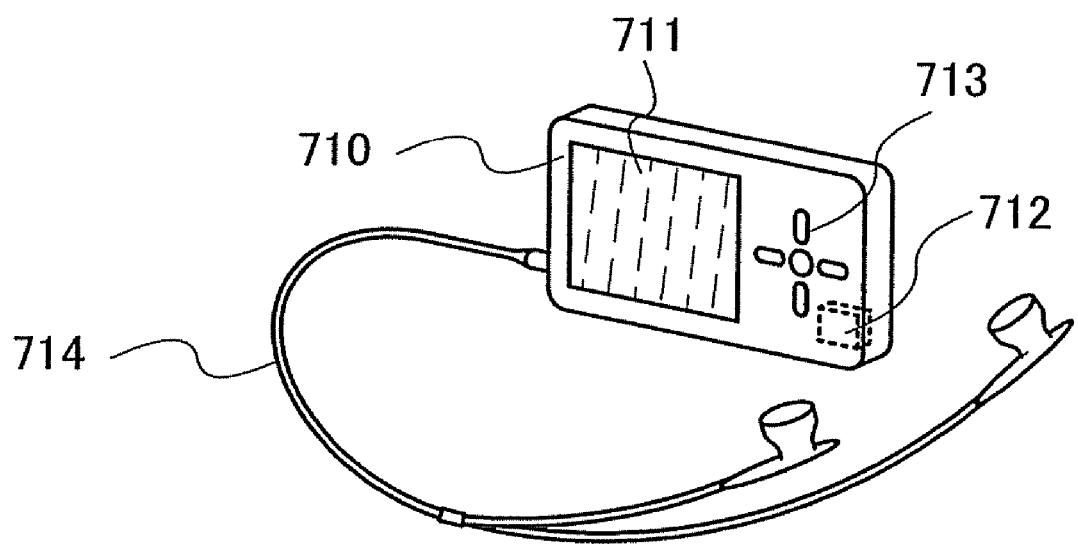
FIG. 8 illustrates an electronic device according to an aspect of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that headphones or wireless earphones can be used instead of the earphones 714. The display portion 711 can be realized with the light-emitting device (passive matrix type or active matrix type) described in Embodiment Mode 6. Further, the display portion 711 may be formed using a segment type light-emitting device. In any case, the use of a light-emitting element of the present invention makes it possible to form a bright display portion which can display images even when using a secondary battery (a nickel-hydrogen battery or the like) while achieving less power consumption. As the memory portion 712, a hard disk or a nonvolatile memory is used. For example, by using a NAND-type nonvolatile memory with a recording capacity of 20 to 200 gigabytes (GB), and operating the operation portion 713, an image or a sound (music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying the present invention is so wide that the light-emitting device is applicable to electronic devices in various fields. By applying the present invention, an electronic device which has a display portion consuming less power can be manufactured.

A light-emitting device to which the present invention is applied has a light-emitting element with high light emission efficiency, and can also be used as a lighting device. One mode of using a light-emitting element to which the present invention is applied as a lighting device is described with reference to FIG. 9.

Figure 9:
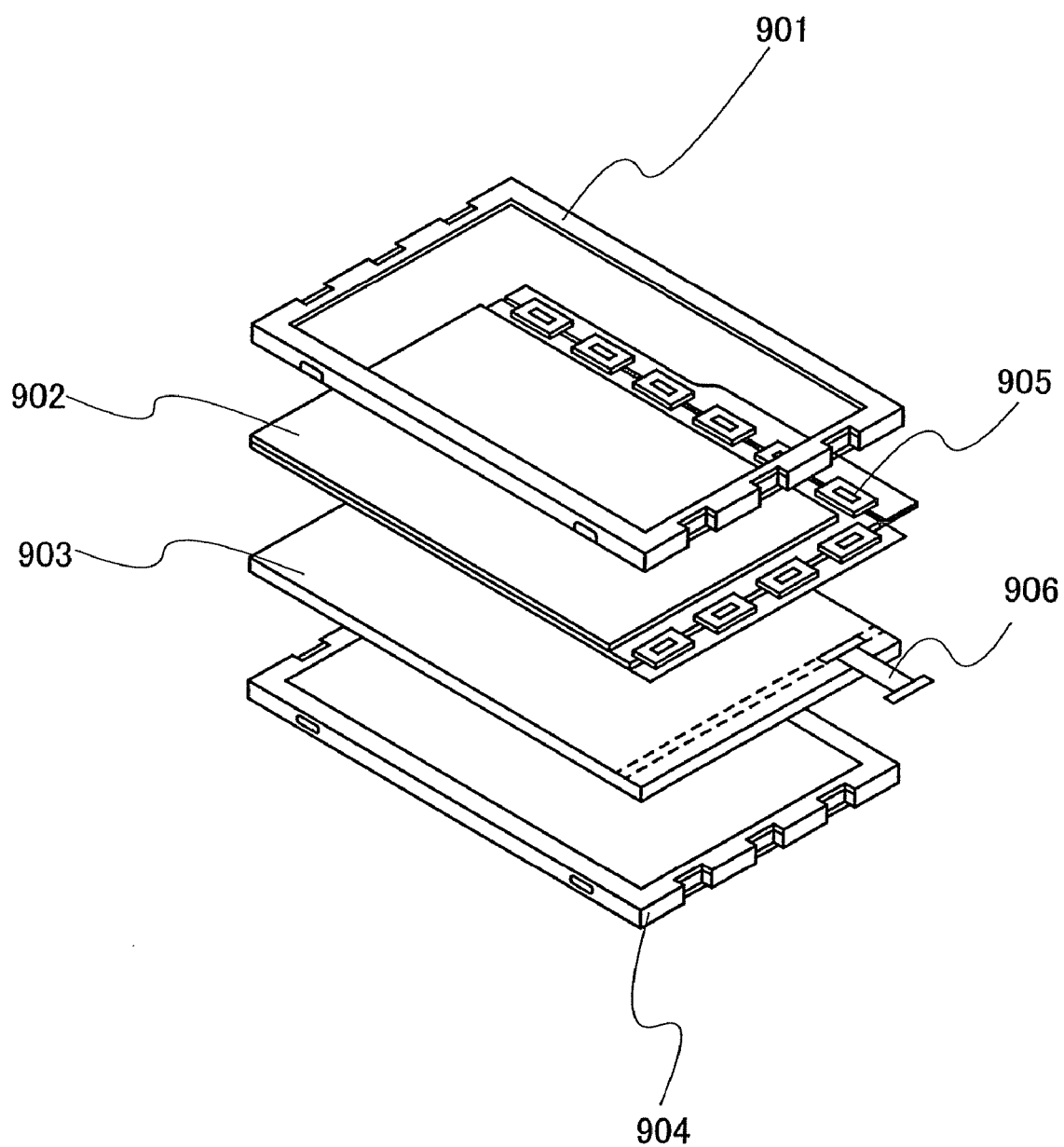
FIG. 9 illustrates an electronic device according to an aspect of the present invention.

FIG. 9 illustrates a liquid crystal display device using the light-emitting device to which the present invention is applied as a backlight, as an example of the electronic device using a light-emitting device according to the present invention as a lighting device. The liquid crystal display device illustrated in FIG. 9 includes a housing 901, a liquid crystal layer 902, a backlight 903, and a housing 904, and the liquid crystal layer 902 is connected to a driver IC 905. The light-emitting device to which the present invention is applied is used as the backlight 903, and current is supplied through a terminal 906.

Since the light-emitting device according to the present invention is thin and consumes less power, reduction in thickness and power consumption of a liquid crystal display device is possible by using a light-emitting device according to the present invention as a backlight of the liquid crystal display device. Moreover, a light-emitting device according to the present invention is a plane emission type lighting device, and can have a large area. Therefore, the backlight can have a large area, and a liquid crystal display device having a large area can be obtained.

Figure 10:
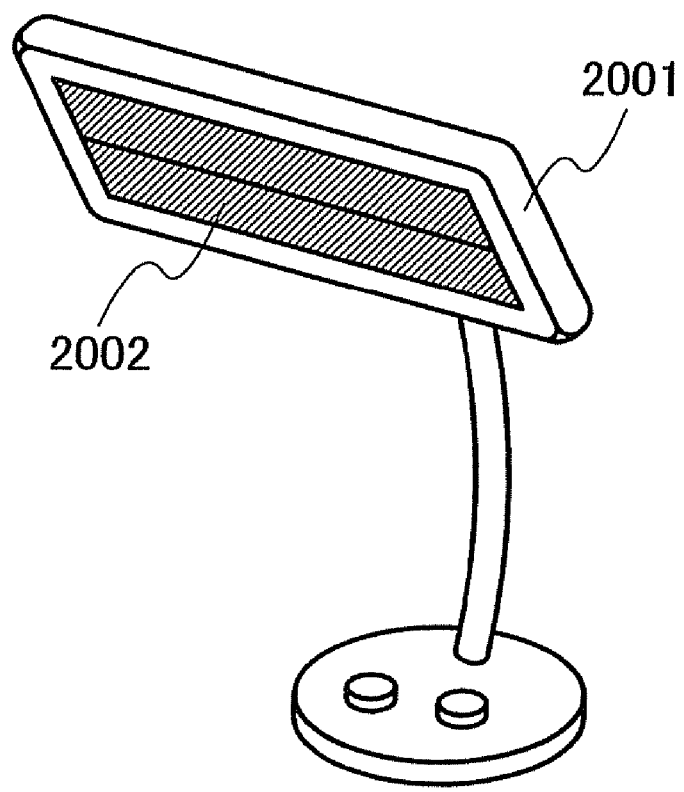
FIG. 10 illustrates a lighting device according to an aspect of the present invention.

FIG. 10 illustrates an example in which a light-emitting device according to the present invention is used as a desk lamp, which is one of lighting devices. The desk lamp illustrated in FIG. 10 includes a housing 2001 and a light source 2002, and a light-emitting device according to the present invention is used as the light source 2002. Since a light-emitting device of the present invention consumes less power, the desk lamp also consumes less power.

Figure 11:
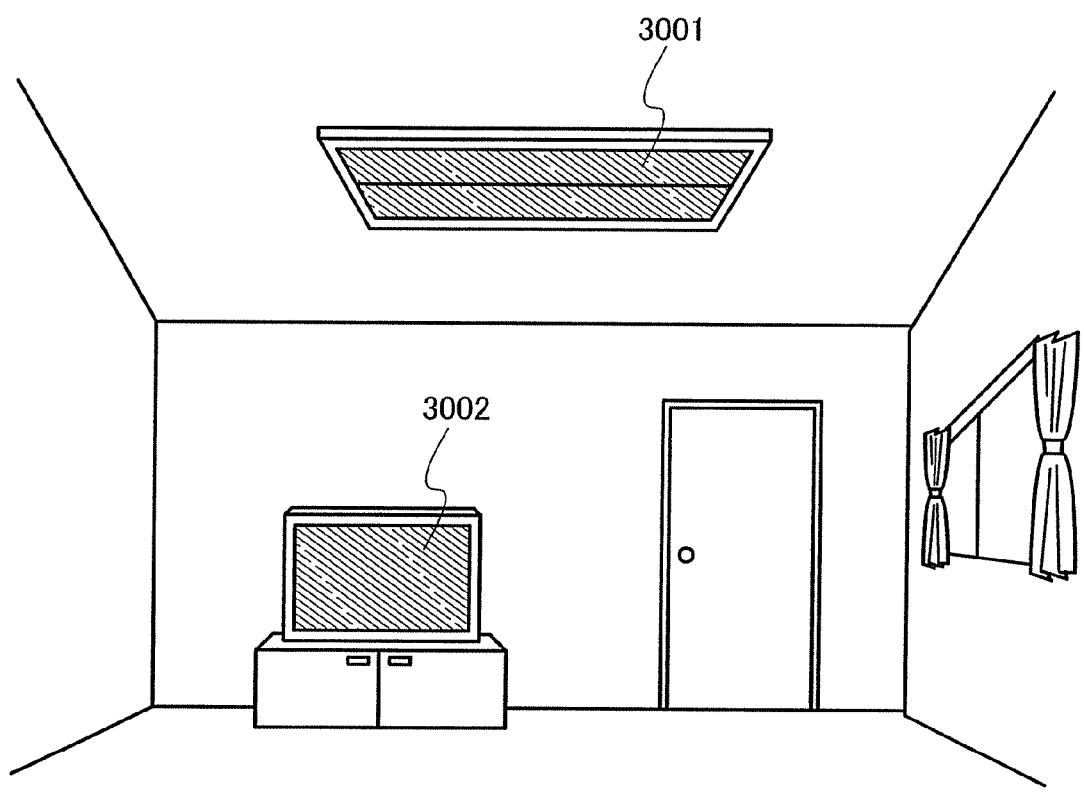
FIG. 11 illustrates a lighting device according to an aspect of the present invention.

FIG. 11 illustrates an example in which a light-emitting device to which the present invention is applied is used as an interior lighting device 3001. Since a light-emitting device according to the present invention can have a large area, a light-emitting device according to the present invention can be used as a lighting device having a large area. Moreover, since a light-emitting device according to the present invention consumes less power, a light-emitting device according to the present invention can be used as a lighting device which consumes less power. Thus, a television device 3002 according to the present invention such as that illustrated in FIG. 6A may be placed in a room where a light-emitting device to which the present invention is applied is used as the interior lighting device 3001, and public broadcasting or movies can be watched there. In such a case, since both devices consume less power, environmental load can be reduced.

Note that this embodiment mode can be appropriately combined with another embodiment mode.

Embodiment 1

In this embodiment, a synthesis method of 3-phenyl-2-[4'-(benzoxazol-2-yl)biphenyl-4-yl]quinoxaline (abbreviation: BOx1PQ) represented by a structural formula (101) will be shown.

(101)

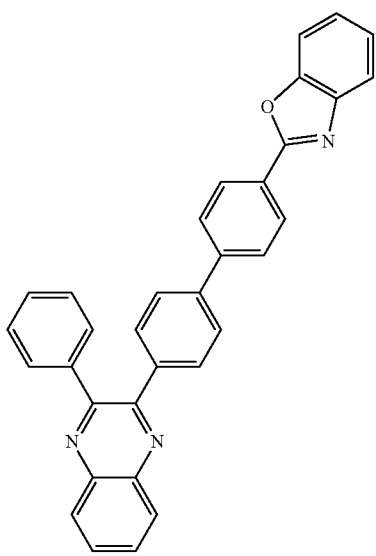

[Step 1: Synthesis of 4-bromo-N-(2-hydroxyphenyl)benzamide]

A synthesis scheme of 4-bromo-N-(2-hydroxyphenyl)benzamide is shown in (B-1).

(B-1)

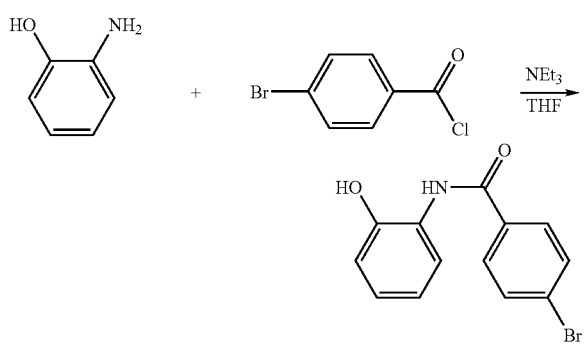

In a 200 mL three-necked flask were placed 2.2 g (20 mmol) of 2-aminophenol, 3.0 mL (22 mmol) of triethylamine, and 50 mL of tetrahydrofuran (THF). Then, the mixture was cooled to 0° C. After cooling, 50 mL of a THF solution containing 4.5 g (20 mmol) of 4-bromobenzoyl chloride was dripped under nitrogen stream. This solution was stirred at 0° C. for 4 hours under nitrogen stream. After a predetermined time, water was added to the solution, and an aqueous layer and an organic layer were separated in the solution. Further, an organic substance was extracted with ethyl acetate from the aqueous layer. The obtained extract and the organic layer were washed together with 0.2 M of hydrochloric acid and a saturated aqueous sodium hydrogen carbonate solution. After that, magnesium sulfate was mixed into the organic layer, and the organic layer was dried. This mixture was subjected to suction filtration through Celite (produced by Wako Pure Chemical Industries, Ltd., Catalog No. 531-16855), and the filtrate was concentrated to obtain a solid. The obtained solid was recrystallized with ethyl acetate/hexane, so that 5.3 g of target white powder was obtained with a yield of 88%.

[Step 2: Synthesis of 2-(4-bromophenyl)benzoxazole]

A synthesis scheme of 2-(4-bromophenyl)benzoxazole is shown in (B-2).

(B-2)

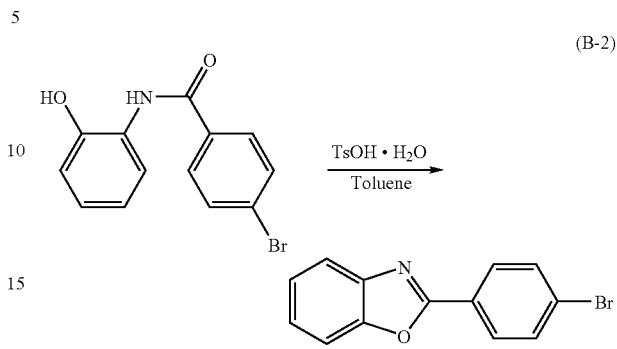

In a 300 mL three-necked flask were placed 5.3 g (18 mmol) of 4-bromo-N-(2-hydroxyphenyl)benzamide, 8.0 g (46 mmol) of p-toluenesulphonic acid monohydrate, and 200 mL of toluene. This mixture was refluxed for 4 hours under nitrogen stream. After a predetermined time, water was added to the mixture that had been refluxed, and an aqueous layer and an organic layer were separated in the mixture. Then, an organic substance was extracted from the aqueous layer with ethyl acetate. The extract and the organic layer were neutralized together with a saturated aqueous sodium hydrogen carbonate solution, and washed with a saturated aqueous sodium chloride solution. Then, the organic layer was dried over magnesium sulfate. This mixture was subjected to suction filtration through Celite (produced by Wako Pure Chemical Industries, Ltd., Catalog No. 531-16855), and the filtrate was concentrated to obtain a solid. The obtained solid was recrystallized with ethyl acetate/hexane, so that 3.1 g of target white powder was obtained with a yield of 61%.

[Step 3: Synthesis of (4-bromophenyl)phenylacetylene]

A synthesis scheme of (4-bromophenyl)phenylacetylene is shown in (B-3).

(B-3)

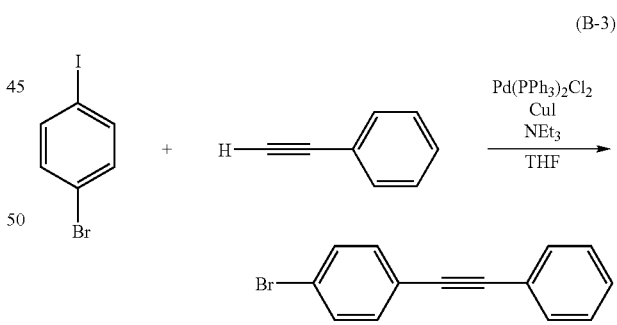

In a 500 mL three-necked flask were placed 14 g (51 mmol) of p-bromoiodobenzene, 5.2 g (52 mmol) of phenylacetylene, and 98 mg (0.50 mmol) of copper(I) iodide. After the atmosphere in the flask was placed with nitrogen, 200 mL of tetrahydrofuran (THF) and 9.0 mL of triethylamine ($Et_3N$) were added to the flask, and the mixture was degassed by being stirred under reduced pressure. To this mixture was added 0.34 mg (0.50 mmol) of bis(triphenylphosphine)palladium(II) dichloride, and the mixture was stirred under nitrogen stream at room temperature for 20 hours. After a predetermined time, a 3% hydrochloric acid was added to the mixture, and an aqueous layer and an organic layer were separated in the mixture. Then, an organic substance was extracted with ethyl acetate from the aqueous layer. The obtained extract was washed with a saturated aqueous sodium chloride solution together with the organic layer and then dried over magnesium sulfate. The mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was condensed to obtain a solid. The obtained solid was recrystallized with hexane, so that, 7.41 g of target light-brown powder was obtained with a yield of 55%.

[Step 4: Synthesis of 1-(4-bromophenyl)-2-phenylethanedione]

A synthesis scheme of 1-(4-bromophenyl)-2-phenylethanedione is shown in (B-4).

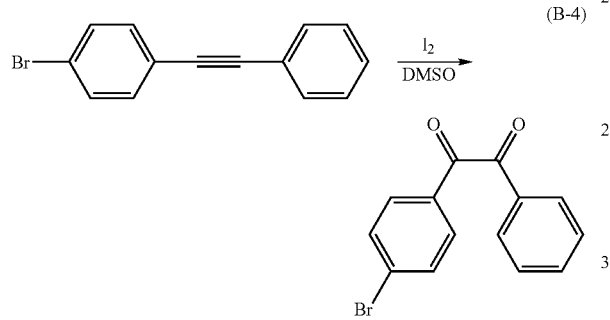

(B-4)

In a 300 mL three-necked flask were placed 7.4 g (28 mmol) of (4-bromophenyl)phenylacetylene, 3.7 g (14 mmol) of iodine, and 70 mL of dimethyl sulfoxide. The solution was stirred under nitrogen stream at 155° C. for 4 hours. After a predetermined time, the solution was cooled to room temperature and added to a 1 wt % aqueous sodium thiosulfate solution; then, a solid was precipitated. The solid was collected by suction filtration. The obtained solid was dissolved in ethyl acetate, and the solution was subjected to suction filtration through Celite (produced by Wako Pure Chemical Industries, Ltd., Catalog No. 531-16855). The filtrate was condensed to obtain a solid. The obtained solid was recrystallized with ethyl acetate/hexane, so that 4.5 g of target pale-yellow powder was obtained with a yield of 71%.

[Step 5: Synthesis of 2-(4-bromophenyl)-3-phenylquinoxaline]

A synthesis scheme of of 2-(4-bromophenyl)-3-phenylquinoxaline is shown in (B-5).

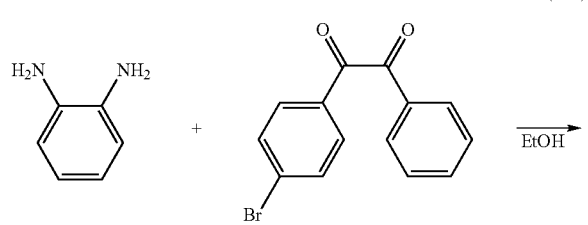

(B-5)

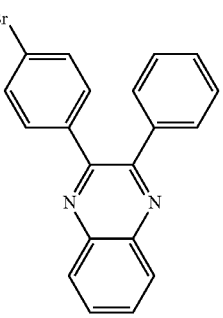

In a 200 mL recovery flask were placed 4.5 g (15 mmol) of 1-(4-bromophenyl)-2-phenylethanedione, 1.8 g (17 mmol) of 1,2-phenylenediamine, and 50 mL of ethanol. This solution was refluxed under nitrogen stream for 2.5 hours. After a predetermined time, the solution was cooled to room temperature, and the precipitated solid was collected by suction filtration. The collected solid was washed with ethanol, so that 5.2 g of target white powder was obtained with a yield of 92%.

[Step 6: Synthesis of 4-(3-phenylquinoxalin-2-yl)phenylboronic acid]

A synthesis scheme of 4-(3-phenylquinoxalin-2-yl)phenylboronic acid is shown in (B-6).

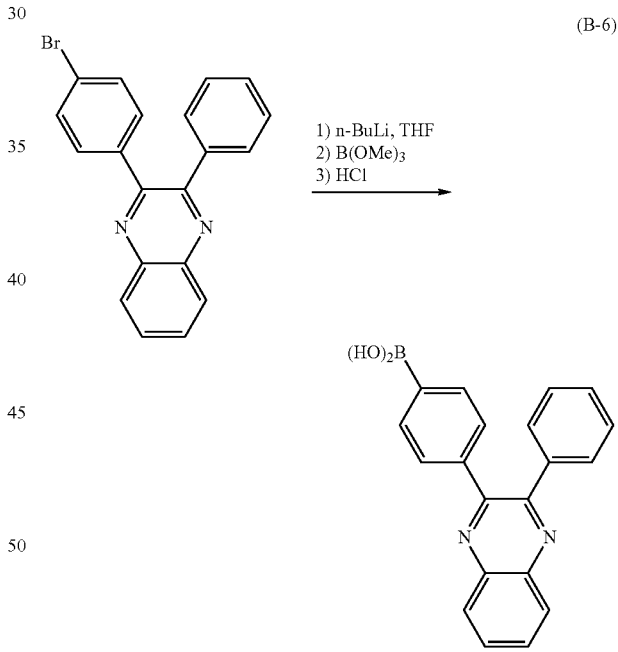

(B-6)

In a 300 mL three-necked flask was placed 5.0 g (13 mmol) of 2-(4-bromophenyl)-3-phenylquinoxaline, and the atmosphere in the flask was placed with nitrogen. There was added 40 mL of tetrahydrofuran, and the mixture was cooled to −78° C. under nitrogen stream. After cooling, 10 mL (16 mmol) of 1.6 M n-butyllithium was dripped thereinto, and the mixture was stirred at the same temperature for 1 hour. After a predetermined time, there was added 3.1 mL (27 mmol) of trimethyl borate, and the temperature of the reaction solution was raised to room temperature, and then, the solution was stirred for 10 hours. After a predetermined time, the reaction solution was cooled to 0° C., to which 100 mL of 0.1 M hydrochloric acid was added, and the solution was stirred for 1 hour. After a predetermined time, an aqueous layer and an organic layer were separated in the mixture, and an organic substance was extracted with ethyl acetate from the aqueous layer. The extract was washed with a saturated aqueous sodium chloride solution together with the organic layer and then dried over magnesium sulfate. The mixture was subjected to suction filtration through Celite (produced by Wako Pure Chemical Industries, Ltd., Catalog No. 531-16855). The obtained filtrate was condensed to obtain a solid. The solid was recrystallized with ethyl acetate/hexane, so that 3.0 g of target pale-yellow powder was obtained with a yield of 66%.

[Step 7: Synthesis of 3-phenyl-2-[4'-(benzoxazol-2-yl)biphenyl-4-yl]quinoxaline (abbreviation: BOx1PQ)]

A synthesis scheme of BOx1PQ is shown in (B-7).

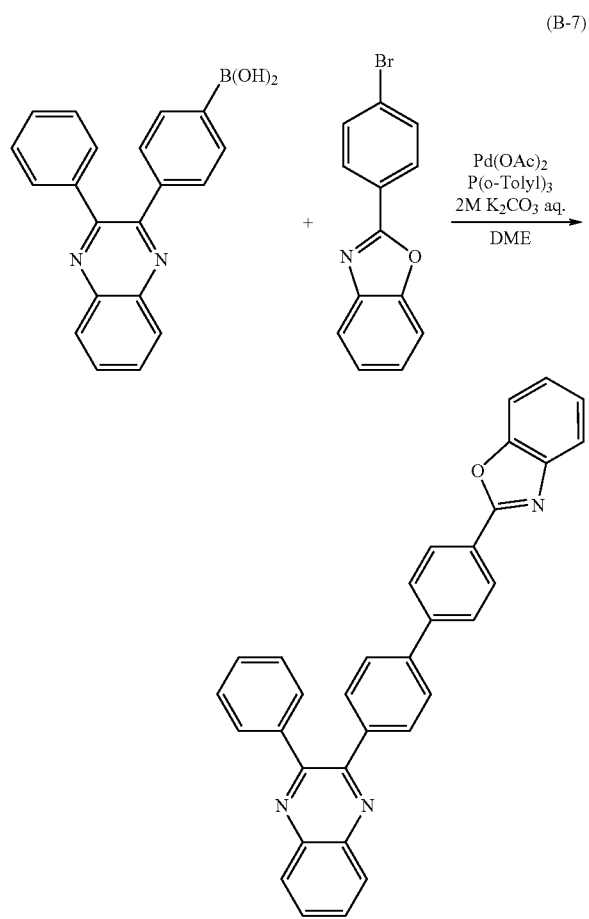

(B-7)

In a 100 mL three-necked flask were placed 0.69 g (2.5 mmol) of 2-(4-bromophenyl)benzoxazole, 0.82 g (2.5 mmol) of 4-(3-phenylquinoxalin-2-yl)phenylboronic acid, and 0.18 g (0.59 mmol) of tri(ortho-tolyl)phosphine, and the atmosphere in the flask was placed with nitrogen. There were added 30 mL of ethylene glycol dimethyl ether (DEM) and 2.5 mL of a 2.0 M aqueous potassium carbonate solution, and the mixture was degassed by being stirred under reduced pressure. 10 mg (0.044 mmol) of palladium(II) acetate was added to this mixture, and this mixture was stirred under nitrogen stream for 5 hours. After a predetermined time, water was added to the mixture, and an aqueous layer and an organic layer were separated in this mixture. Then, an organic substance was extracted with ethyl acetate from the aqueous layer. The extract was washed with a saturated aqueous sodium chloride solution together with the organic layer, and the organic layer was then dried over magnesium sulfate. The mixture was subjected to suction filtration through Celite (produced by Wako Pure Chemical Industries, Ltd., Catalog No. 531-16855), and the filtrate was condensed to obtain a solid. The solid was purified by silica gel column chromatography (solvent: chloroform) and further recrystallized with chloroform/hexane, so that 1.0 g of target white powder was obtained with a yield of 85%.

Then, 1.0 g of the obtained target substance was subjected to sublimation purification at 235° C. under argon stream (flow rate: 3.0 mL/min) and a pressure of 10 Pa for 23 hours, so that 0.68 g of the target substance was obtained at a collection rate of 86%. The compound was measured by nuclear magnetic resonance (NMR) spectrometry and identified as 3-phenyl-2-[4'-(benzoxazol-2-yl)biphenyl-4-yl]quinoxaline (abbreviation: BOx1PQ).

Figure 13A:
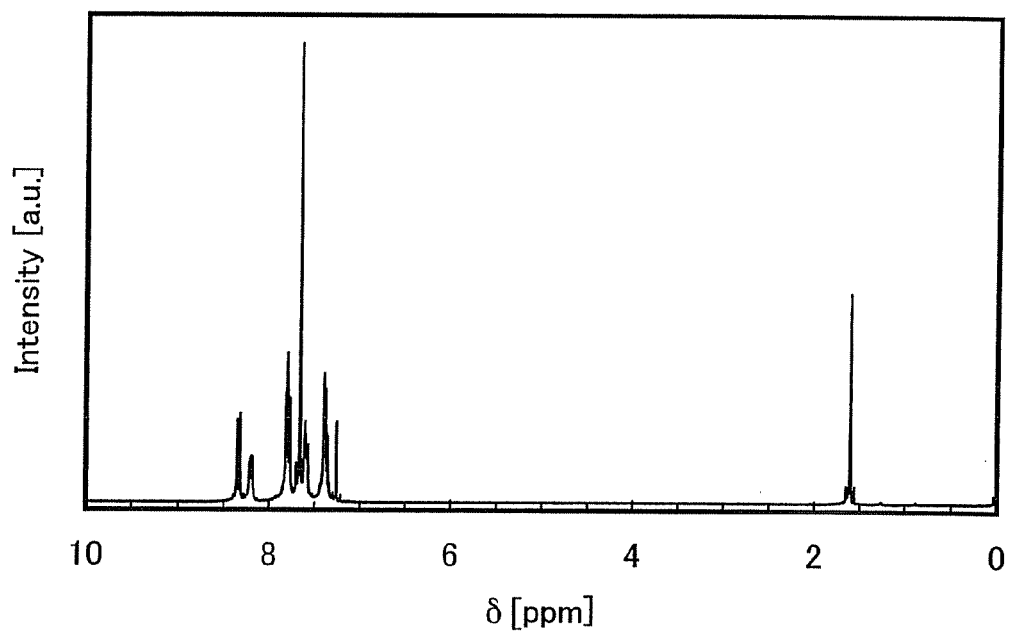
FIGS. 13A and 13B are graphs each showing a $^1$H NMR chart of 3-phenyl-2-[4'-(benzoxazol-2-yl)biphenyl-4-yl]quinoxaline (abbreviation: BOx1PQ).
Figure 13B:
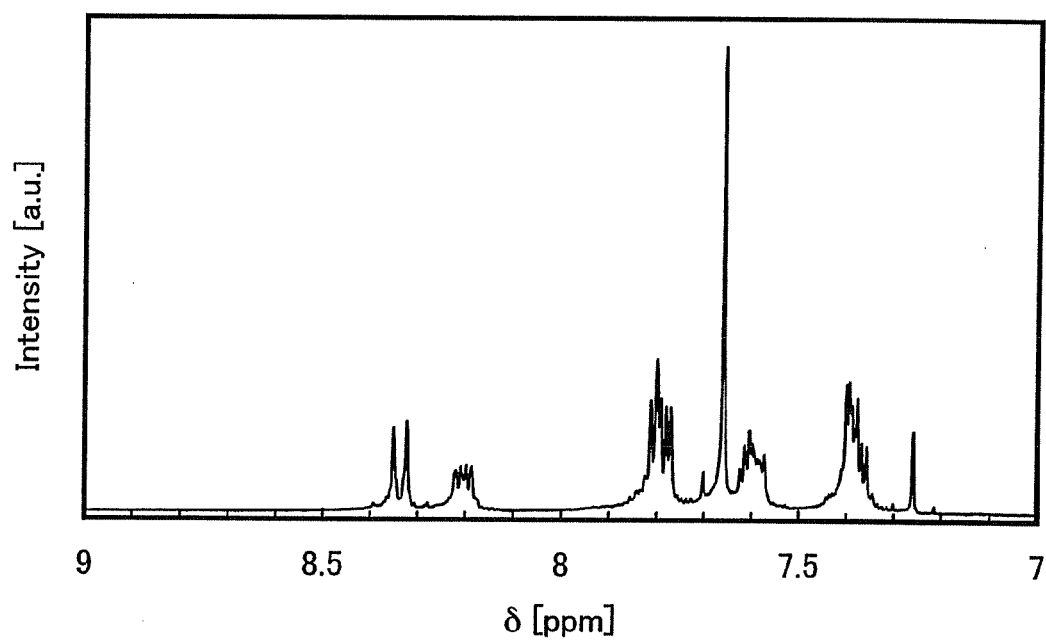

Hereinafter, the $^1$H NMR data is shown. $^1$H NMR (300 MHz, CDCl$_3$): δ (ppm)=7.34-7.43 (m, 5H), 7.57-7.65 (m, 7H), 7.70-7.84 (m, 5H), 8.18-8.22 (m, 2H), 8.33 (d,J=8.1 Hz, 2H). FIGS. 13A and 13B show $^1$H NMR charts. Note that FIG. 13B shows an enlarged chart showing the range from 7.0 ppm to 9.0 ppm in FIG. 13A.

Thermogravimetry-differential thermal analysis (TG-DTA) of the thus obtained BOx1PQ was performed. In measuring, a high vacuum differential type differential thermal balance (type DTA2410SA, manufactured by Bruker AXS K.K.) was used. The measurement was performed under normal pressure at a rate of temperature rise of 10° C./min under nitrogen stream (flow rate: 200 mL/min). It was found from the relationship between weight and temperature (thermogravimetry) that the 5% weight loss temperature was 393° C. and the melting point was 240° C., which is indicative of high thermal stability.

Figure 14:
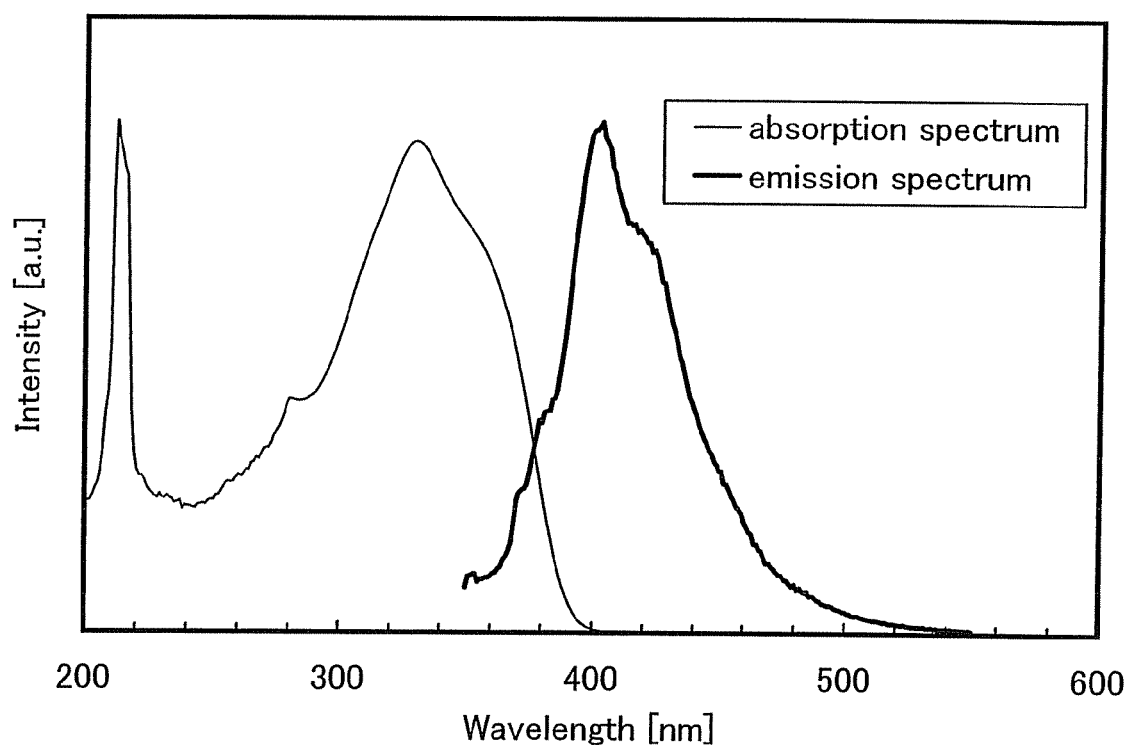
FIG. 14 is a graph showing an absorption spectrum and an emission spectrum of a toluene solution of 3-phenyl-2-[4'-(benzoxazol-2-yl)biphenyl-4-yl]quinoxaline (abbreviation: BOx1PQ).

FIG. 14 shows an absorption spectrum and an emission spectrum of a toluene solution of BOx1PQ. The measurement was performed using an ultraviolet-visible spectrophotometer (V-550, manufactured by JASCO Corporation). The solution was placed in a quartz cell. The absorption spectrum from which the absorption spectrum of quartz is subtracted is shown in FIG. 14. In FIG. 14, the horizontal axis represents wavelength (nm) and the vertical axis represents intensity (a given unit). In the case of the toluene solution, an absorption was observed at around 330 nm. In addition, in the case of the toluene solution, the maximum emission wavelength was 403 nm (excitation wavelength: 334 nm).

Figure 15:
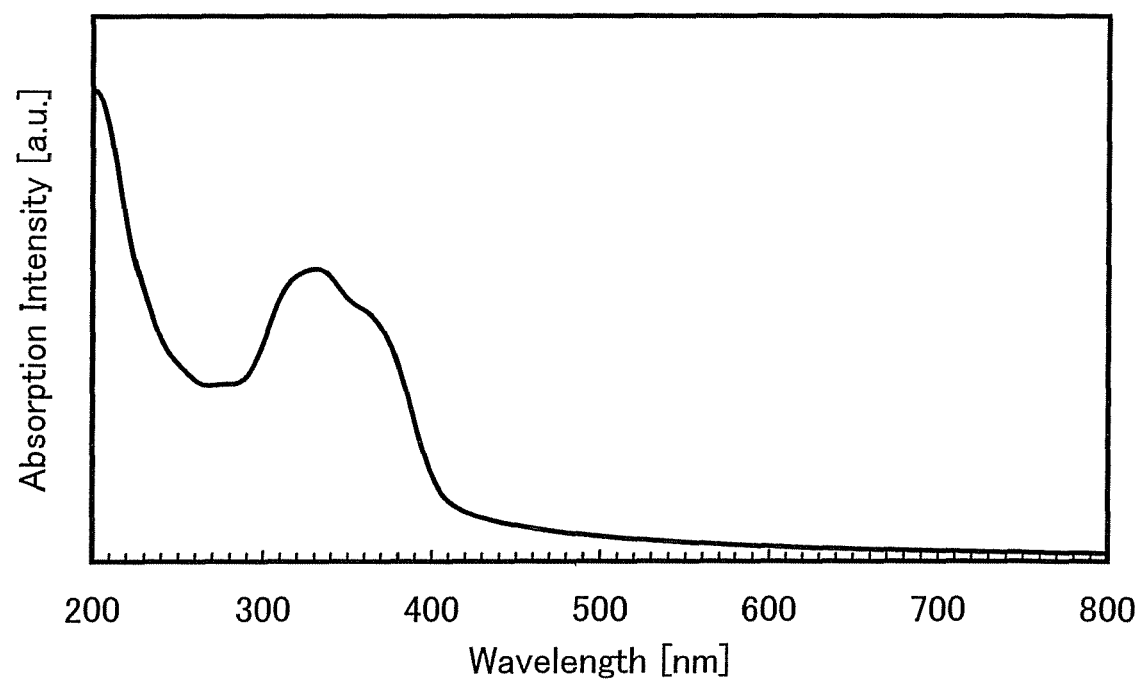
FIG. 15 is a graph showing an absorption spectrum of a thin film of 3-phenyl-2-[4'-(benzoxazol-2-yl)biphenyl-4-yl]quinoxaline (abbreviation: BOx1PQ).
Figure 16:
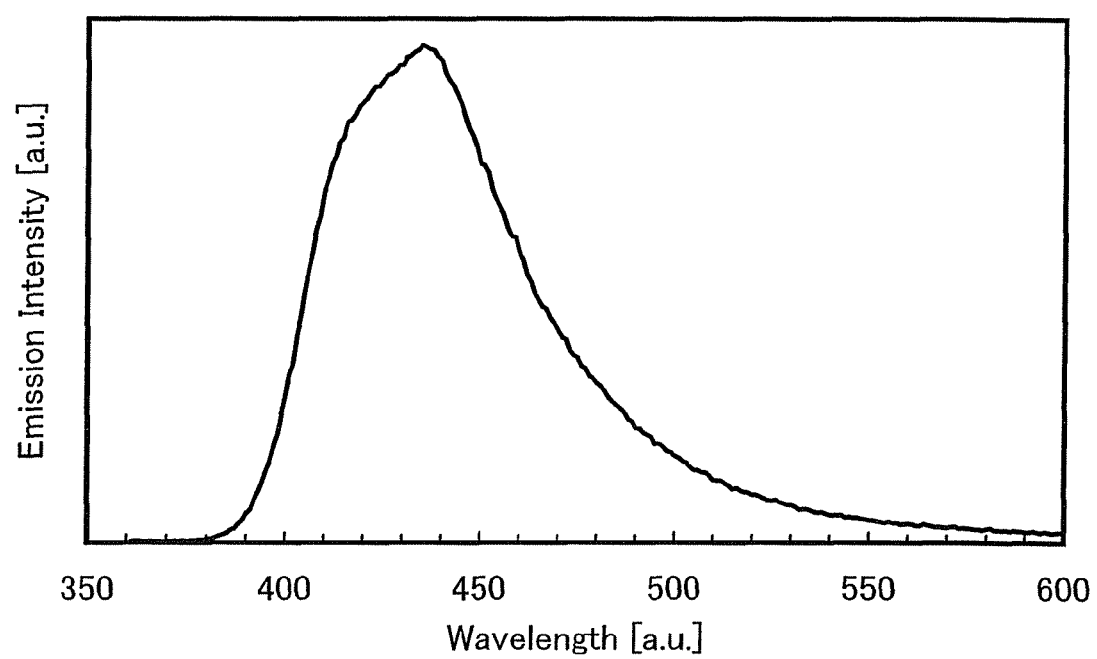
FIG. 16 is a graph showing an emission spectrum of a thin film of 3-phenyl-2-[4'-(benzoxazol-2-yl)biphenyl-4-yl]quinoxaline (abbreviation: BOx1PQ).

FIG. 15 shows an absorption spectrum of a thin film of BOx1PQ and FIG. 16 shows an emission spectrum of the thin film of BOx1PQ. The measurement was performed using an ultraviolet-visible spectrophotometer (V-550, manufactured by JASCO Corporation). A sample was manufactured by evaporation of the thin film over a quartz substrate, and the absorption spectrum thereof, from which the absorption spectrum of quartz is subtracted, is shown in FIG. 15. In FIG. 15, the horizontal axis represents wavelength (nm) and the vertical axis represents absorption intensity (a given unit). In FIG. 16, the horizontal axis represents wavelength (nm) and the vertical axis represents emission intensity (a given unit). In the case of the thin film, an absorption was observed at around 330 nm. In addition, in the case of the thin film, the maximum emission wavelength was 435 nm (excitation wavelength: 350 nm).

In addition, the ionization potential of BOx1PQ in a thin film form was 5.71 eV when measured in the air with a photoelectron spectrometer (AC-2, manufactured by RIKEN KEIKI CO., LTD.). As a result, it was found that the HOMO level was −5.71 eV. Furthermore, an absorption edge was obtained from a Tauc plot assuming direct transition based on the absorption spectrum data of the thin film of BOx1PQ, and the absorption edge was estimated as an optical energy gap. As a result, the energy gap was 3.10 eV. The LUMO level was found to be −2.61 eV by calculation from the value of the energy gap and the HOMO level.

Embodiment 2

In this embodiment, a synthesis method of 2,3-bis[4'-(benzoxazol-2-yl)biphenyl-4-yl]quinoxaline (abbreviation: BOx2PQ) represented by a structural formula (201) will be shown.

(201)

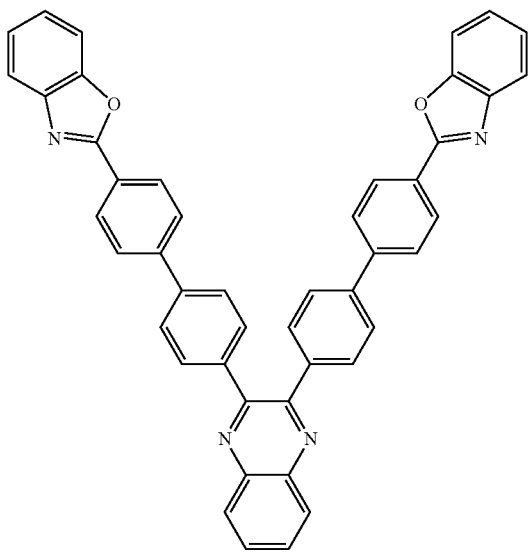

[Step 1: Synthesis of 2,3-bis(4-bromophenyl)quinoxaline]
A synthesis scheme of 2,3-bis(4-bromophenyl)quinoxaline is shown in (C-1).

(C-1)

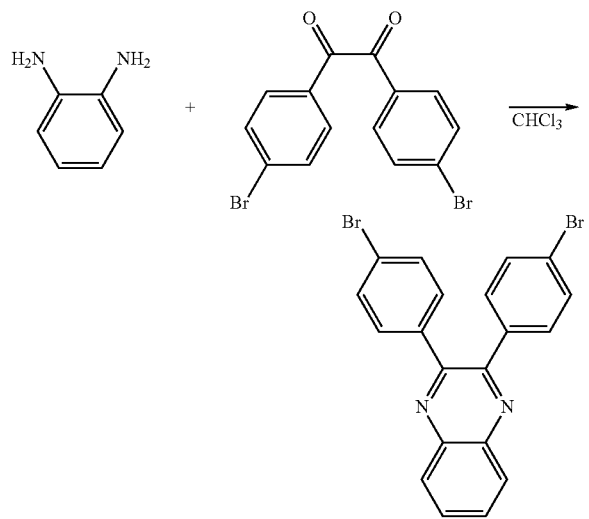

In a 500 mL three-necked flask were placed 30 g (82 mmol) of 4,4'-dibromobenzil, 9.3 g (86 mmol) of 1,2-phenylenediamine, and 300 mL of chloroform. The mixture was refluxed at 80° C. for 5 hours under nitrogen stream. After passing a predetermined time, the solution was cooled to room temperature and water was added thereto, and an aqueous layer and an organic layer were separated in the mixture. The aqueous layer was extracted with chloroform, and the extract was dried over magnesium sulfate together the organic layer. The mixture was subjected to suction filtration, and filtrate was concentrated. The obtained solid was dissolved in toluene, and this solution was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina. The filtrate was concentrated, so that 30 g of target white powder of 2,3-bis(4-bromophenyl)quinoxaline was obtained with a yield of 83%.

[Step 2: Synthesis of 4,4'-(quinoxaline-2,3-diyl)diphenylboronic acid]
A synthesis scheme of 4,4'-(quinoxaline-2,3-diyl)diphenylboronic acid is shown in (C-2).

(C-2)

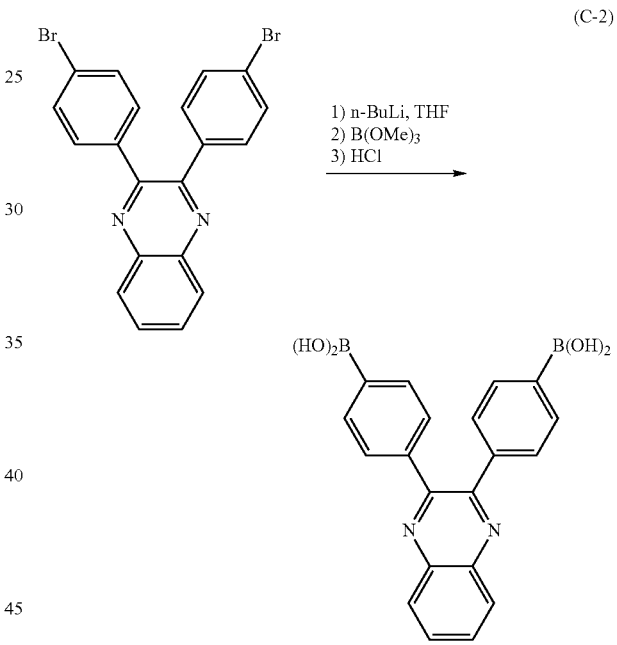

In a 500 mL three-necked flask was placed 10 g (22 mmol) of 2,3-bis(4-bromophenyl)quinoxaline, and the atmosphere in the flask was placed with nitrogen. There was added 100 mL of tetrahydrohfuran (THF) and, the mixture was cooled to −78° C. in nitrogen stream. After cooling, 31 mL (49 mmol) of 1.6 M n-butyllithium was dripped and stirred at the same temperature for an hour. After a predetermined time, 10 mL (90 mmol) of trimethyl borate was added, the temperature of the solution was raised to room temperature, and the solution was stirred for 10 hours. After a predetermined time, the solution was cooled to 0° C., 100 mL of 0.1 M hydrochloride acid was added thereto, and the solution was stirred for an hour. In the obtained mixture, an aqueous layer and an organic layer were separated, and from the aqueous layer, an organic substance was extracted with ethyl acetate. The extracted solution and the organic layer were washed together with saturated aqueous sodium chloride solution. After that, the mixture was dried over magnesium sulfate and subjected to suction filtration through Celite (produced by Wako Pure Chemical Industries, Ltd., Catalog No. 531-16855), and the obtained filtrate was concentrated. The obtained solid was recrystallized with ethyl acetate, so that 7.2 g of target yellow powder was obtained with a yield of 85%.

[Step 3: Synthesis of 2,3-bis[4'-(benzoxazol-2-yl)biphenyl-4-yl]quinoxaline (abbreviation: BOx2PQ)]

A synthesis scheme of BOx2PQ is shown in (C-3).

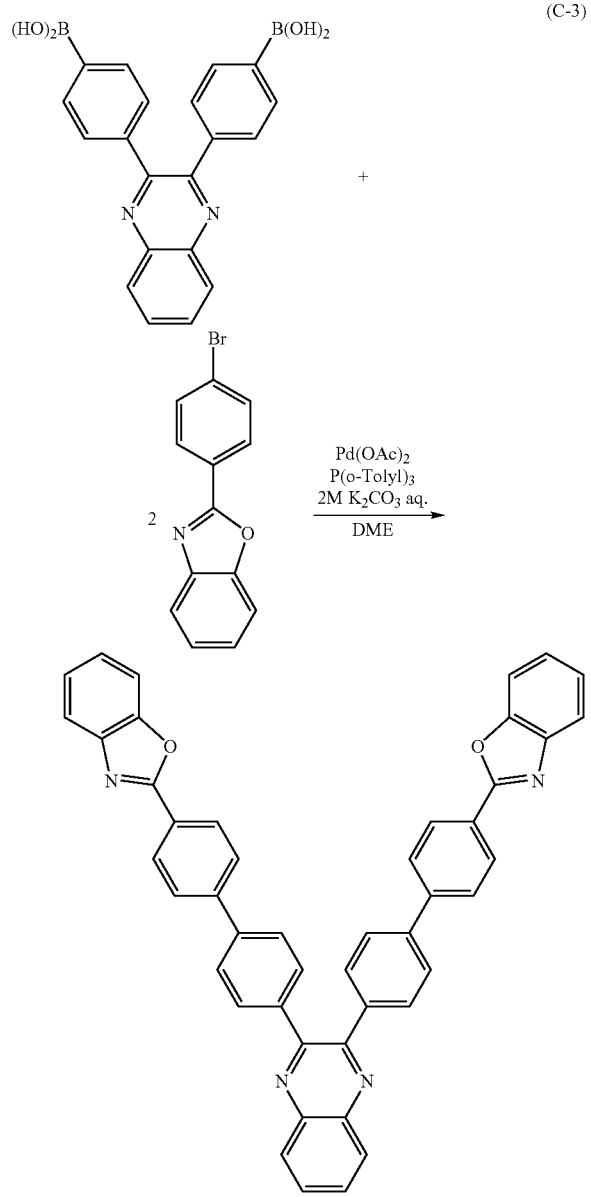

(C-3)

In a 100 mL three-necked flask were placed 1.5 g (5.6 mmol) of 2-(4-bromophenyl)benzoxazole, 1.0 g (2.8 mmol) of 4,4'-(quinoxaline-2,3-diyl)diphenylboronic acid, and 0.17 g (0.57 mmol) of tri(ortho-tolyl)phosphine. The atmosphere in the flask was placed with nitrogen, and there were added 20 mL of ethylene glycol dimethyl ether (DME) and 3.0 mL of a 2.0 M aqueous potassium carbonate solution. The mixture was degassed by being stirred under reduced pressure, to which 13 mg (0.058 mmol) of palladium(II) acetate was added. The mixture was stirred under nitrogen stream for 10 hours. After a predetermined time, water was added to the mixture, and an aqueous layer and an organic layer were separated in the mixture. Then, an organic substance was extracted with chloroform from the aqueous layer. The extract was washed with a saturated aqueous sodium chloride solution together with the organic layer, and the organic layer was then dried over magnesium sulfate. The mixture was subjected to suction filtration through Celite (produced by Wako Pure Chemical Industries, Ltd., Catalog No. 531-16855), and the filtrate was condensed to obtain a solid. The solid was purified by silica gel column chromatography (solvent: chloroform) and further recrystallized with chloroform/hexane, so that 0.73 g of target white powder was obtained with a yield of 40%.

Then, 0.71 g of the obtained target substance was subjected to sublimation purification at 320° C. under argon stream (flow rate: 3.0 mL/min) and a pressure of 10 Pa for 12 hours, so that 0.43 g of the target substance was obtained at a collection rate of 60%. The compound was measured by nuclear magnetic resonance (NMR) spectrometry and identified as 2,3-bis[4'-(benzoxazol-2-yl)biphenyl-4-yl]quinoxaline (abbreviation: BOx2PQ).

Figure 17A:
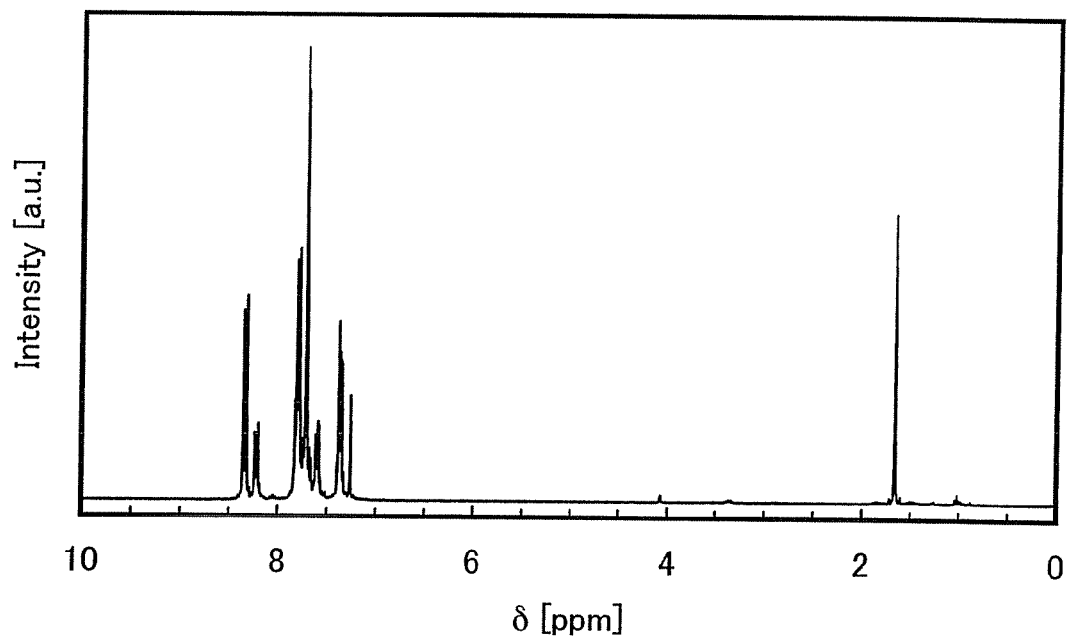
FIGS. 17A and 17B are graphs each showing a $^1$H NMR chart of 2,3-bis[4'-(benzoxazol-2-yl)biphenyl-4-yl]quinoxaline (abbreviation: BOx2PQ).
Figure 17B:
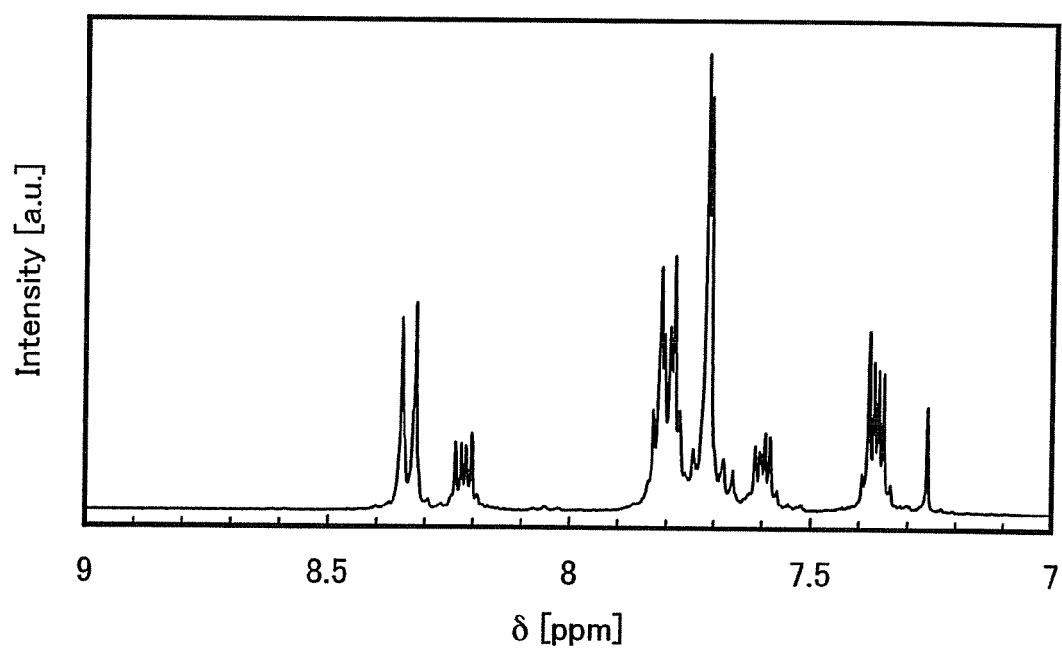

Hereinafter, the $^1$H NMR data is shown. $^1$H NMR (300 MHz, CDCl$_3$): δ (ppm)=7.34-7.39 (m, 4H), 7.58-7.61 (m, 2H), 7.66-7.82 (m, 16H), 8.20-8.23 (m, 2H), 8.33 (d, J=8.7Hz, 4H). The $^1$H NMR chart is shown in FIGS. 17A and 17B. Note that FIG. 17B shows an enlarged chart showing the range form 7.0 ppm to 9.0 ppm in FIG. 17A.

Figure 18A:
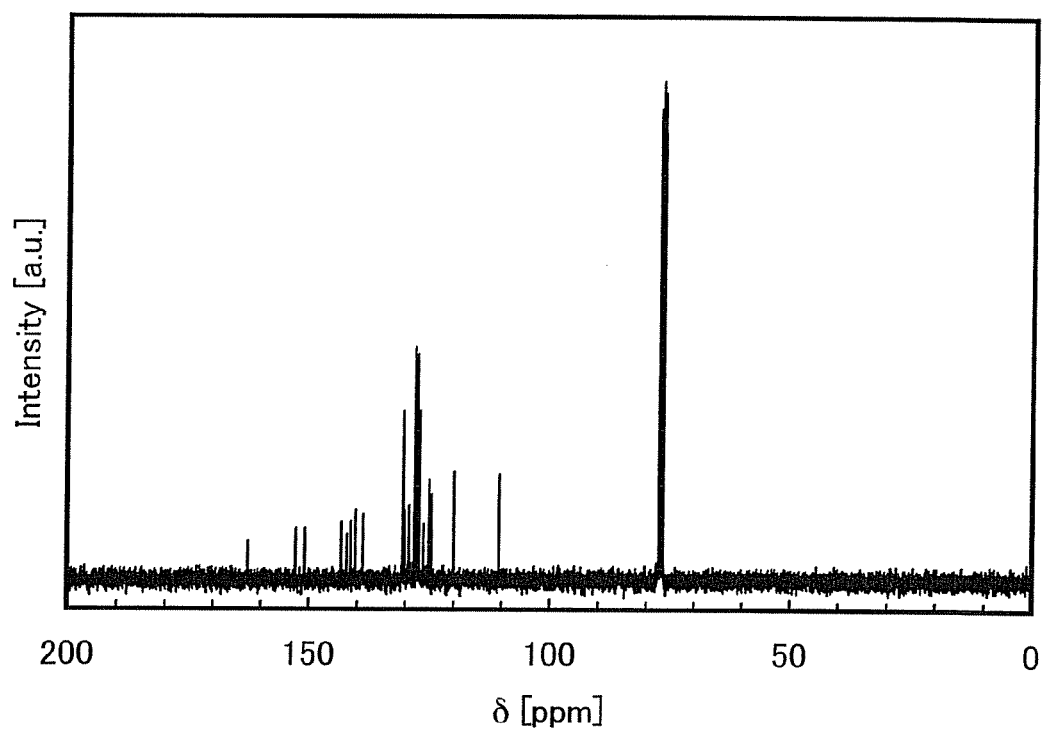
FIGS. 18A and 18B are graphs each showing a $^{13}$C NMR chart of 2,3-bis[4'-(benzoxazol-2-yl)biphenyl-4-yl]quinoxaline (abbreviation: BOx2PQ).
Figure 18B:
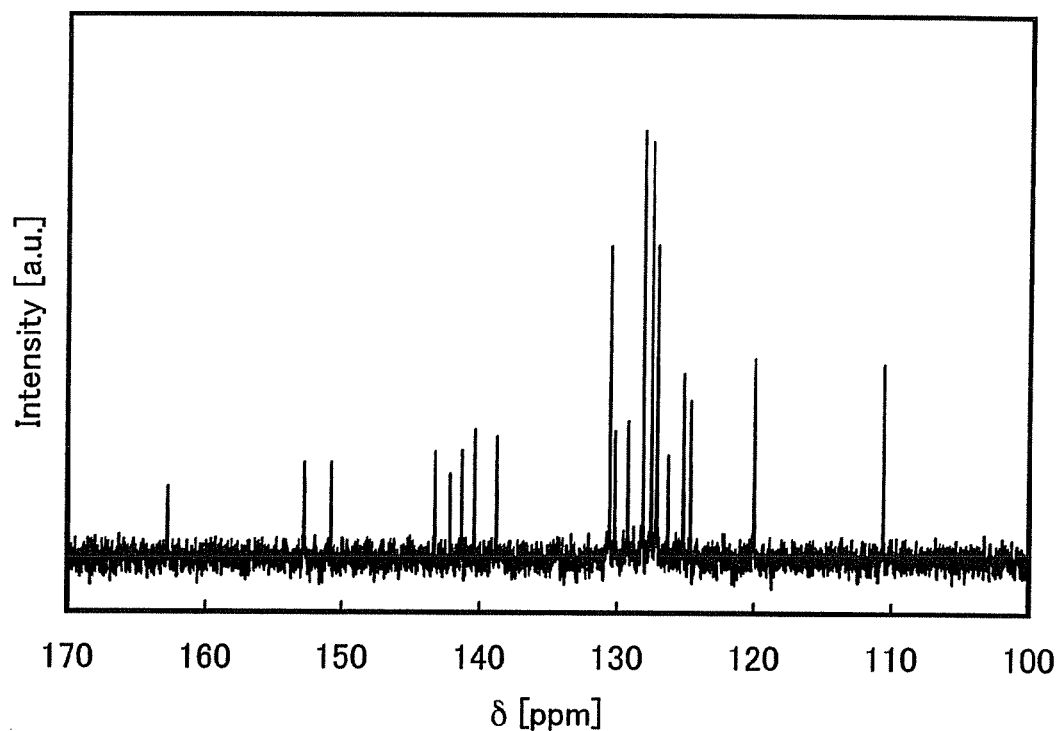

In addition, the $^{13}$C NMR data is shown below. $^{13}$C NMR (75 MHz, CDCl$_3$): δ (ppm)=110.59, 119.99, 124.63, 125.17, 126.31, 127.11, 127.52, 128.12, 129.23, 130.18, 130.52, 138.74, 140.37, 141.30, 142.15, 143.25, 150.78, 152.73, 162.76. The $^{13}$C NMR chart is shown in FIGS. 18A and 18B. Note that FIG. 18B shows an enlarged chart showing the range from 100 ppm to 170 ppm in FIG. 18A.

Thermogravimetry-differential thermal analysis (TG-DTA) of the thus obtained BOx2PQ was performed. In measuring, a high vacuum differential type differential thermal balance (type DTA2410SA, manufactured by Bruker AXS K.K.) was used. The measurement was performed under normal pressure at a rate of temperature rise of 10° C./min under nitrogen stream (flow rate: 200 mL/min). It was found from the relationship between weight and temperature (thermogravimetry) that the 5% weight loss temperature was 488° C. and the melting point was 271° C., which is indicative of high thermal stability.

Figure 19:
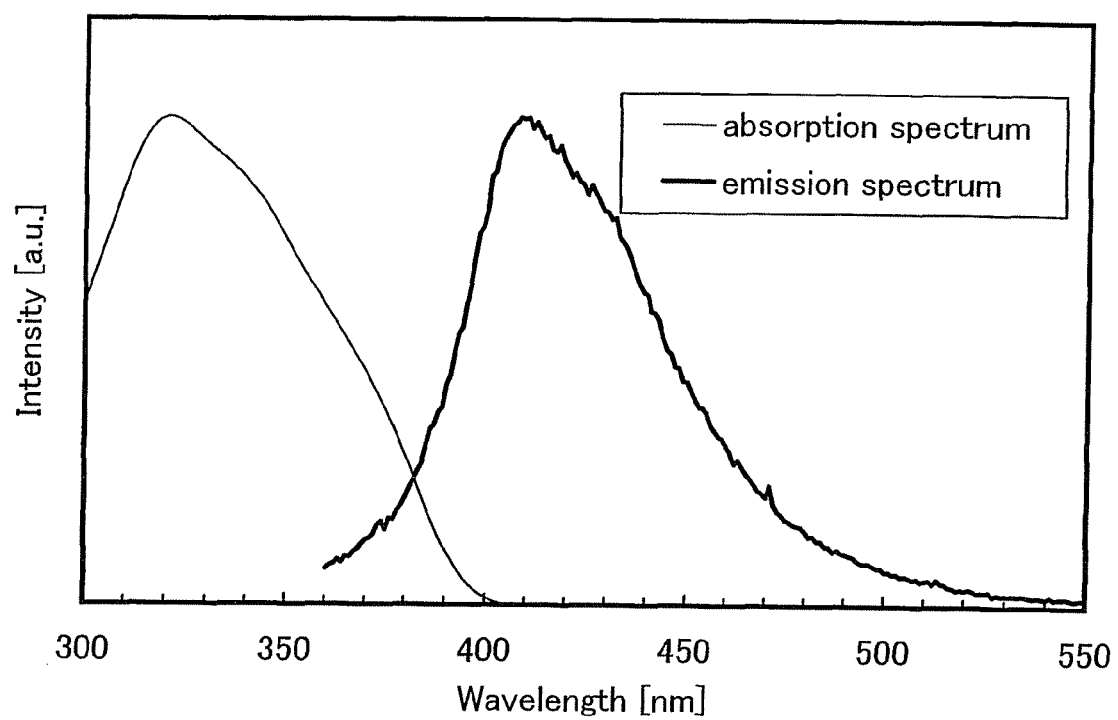
FIG. 19 is a graph showing an absorption spectrum and an emission spectrum of a toluene solution of 2,3-bis[4'-(benzoxazol-2-yl)biphenyl-4-yl]quinoxaline (abbreviation: BOx2PQ).

FIG. 19 shows an absorption spectrum and an emission spectrum of a toluene solution of BOx2PQ. The measurement was performed using an ultraviolet-visible spectrophotometer (V-550, manufactured by JASCO Corporation). The solution was placed in a quartz cell. The absorption spectrum from which the absorption spectrum of quartz is subtracted is shown in FIG. 19. In FIG. 19, the horizontal axis represents wavelength (nm) and the vertical axis represents intensity (a given unit). In the case of the toluene solution, an absorption was observed at around 320 nm. In addition, in the case of the toluene solution, the maximum emission wavelength was 409 nm (excitation wavelength: 320 nm).

Figure 20:
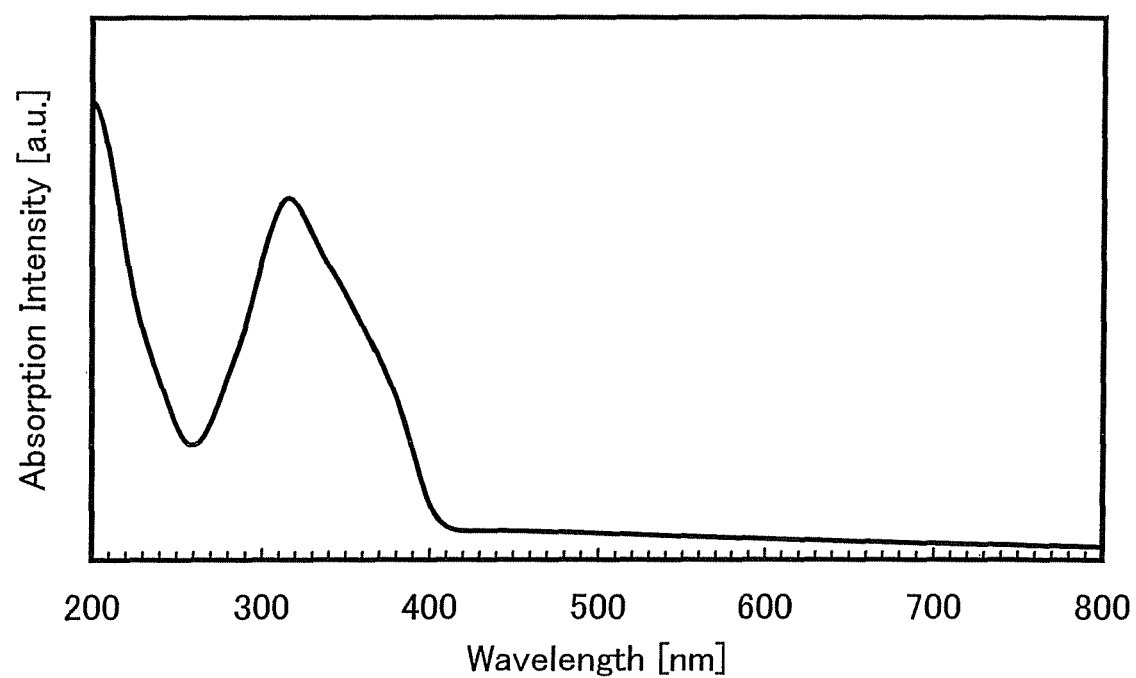
FIG. 20 is a graph showing an absorption spectrum of a thin film of 2,3-bis[4'-(benzoxazol-2-yl)biphenyl-4-yl]quinoxaline (abbreviation: BOx2PQ).
Figure 21:
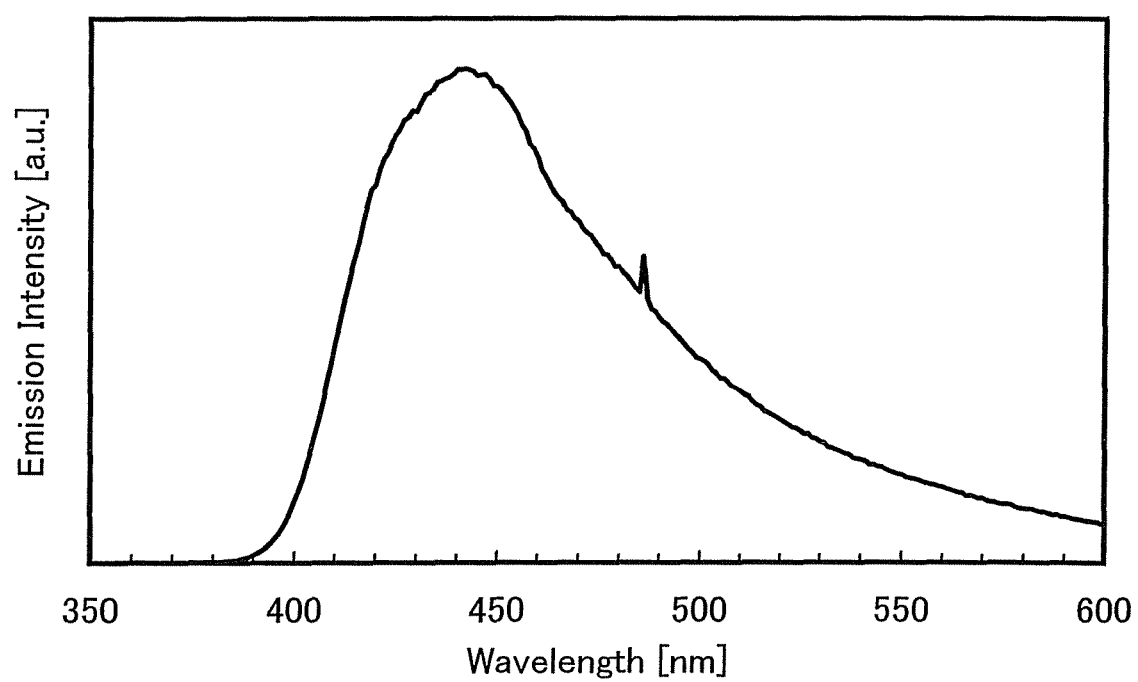
FIG. 21 is a graph showing an emission spectrum of a thin film of 2,3-bis[4'-(benzoxazol-2-yl)biphenyl-4-yl]quinoxaline (abbreviation: BOx2PQ).

FIG. 20 shows an absorption spectrum of a thin film of BOx2PQ and FIG. 21 shows an emission spectrum of the thin film of BOx2PQ. The measurement was performed using an ultraviolet-visible spectrophotometer (V-550, manufactured by JASCO Corporation). A sample was manufactured by evaporation of the thin film over a quartz substrate, and the absorption spectrum thereof, from which the absorption spectrum of quartz is subtracted, is shown in FIG. 20. In FIG. 20, the horizontal axis represents wavelength (nm) and the vertical axis represents absorption intensity (a given unit). In FIG. 21, the horizontal axis represents wavelength (nm) and the vertical axis represents emission intensity (a given unit). In the case of the thin film, an absorption was observed at around 316 nm. In addition, in the case of the thin film, the maximum emission wavelength was 442 nm (excitation wavelength: 344 nm).

In addition, the ionization potential of BOx2PQ in a thin film form was 5.74 eV when measured in the air with a photoelectron spectrometer (AC-2, manufactured by RIKEN KEIKI CO., LTD.). As a result, it was found that the HOMO level was −5.74 eV. Furthermore, an absorption edge was obtained from a Tauc plot assuming direct transition based on the absorption spectrum data of the thin film of BOx2PQ, and the absorption edge was estimated as an optical energy gap. As a result, the energy gap was 3.12 eV. The LUMO level was found to be −2.62 eV by calculation from the value of the energy gap and the HOMO level.

Embodiment 3

Figure 22:
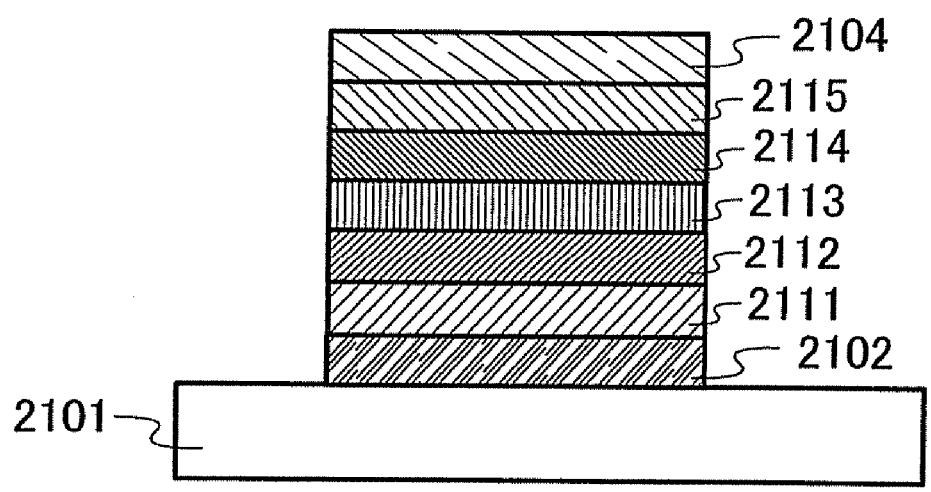
FIG. 22 illustrates a light-emitting element of an embodiment.

In this embodiment, a light-emitting element of the present invention will be described with reference to FIG. 22. Structural formulae of materials used in this embodiment are given below. Note that the materials, the structural formulae of which have already been shown, are omitted.

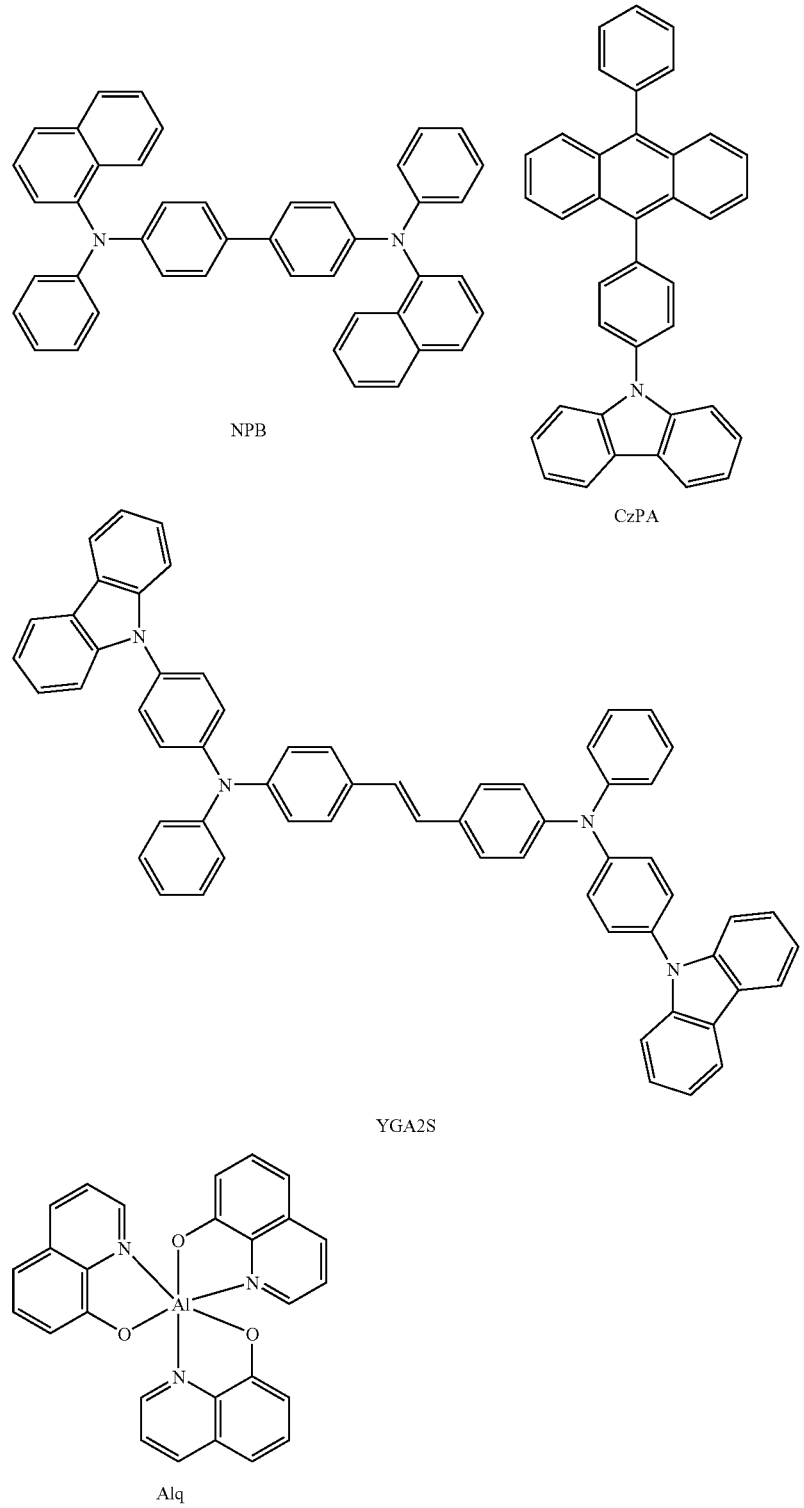

Methods for manufacturing light-emitting elements of this embodiment are hereinafter described.

<Light-Emitting Element 1a>

First, a film of indium tin oxide containing silicon oxide (ITSO) was formed over a glass substrate 2101 by a sputtering method to form a first electrode 2102. Note that the thickness was 110 nm and the electrode area was 2 mm×2 mm.

Next, the substrate was fixed to a substrate holder provided in a vacuum evaporation apparatus such that the side on which the first electrode was formed faced downward. After the pressure in a film formation chamber was lowered to approximately $10^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbreviation: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino] biphenyl (abbreviation: NPB) was formed to a thickness of 10 nm on the layer 2111 containing a composite material by an evaporation method employing resistance heating to form a hole transporting layer 2112.

Then, a light-emitting layer 2113 was formed to a thickness of 30 nm on the hole transporting layer 2112 by co-evaporation of 9-[4-(10-phenyl-9-anthryl)phenyl]-9H-carbazole (abbreviation: CzPA) and N,N'-bis[4-(9H-carbazol-9-yl)phenyl]-N,N'-diphenylstilbene-4,4'-diamine (abbreviation: YGA2S). Here, the weight ratio of CzPA to YGA2S was adjusted to be 1: 0.04 (=CzPA: YGA2S).

After that, a film of 2,3-bis[4'-(benzoxazol-2-yl)biphenyl-4-yl]quinoxaline (abbreviation: BOx2PQ) represented by the structural formula (201), which is a compound synthesized by Embodiment 2, was formed to a thickness of 30 nm on the light-emitting layer 2113 by an evaporation method employing resistance heating to form an electron transporting layer 2114.

Furthermore, a film of lithium fluoride was formed to a thickness of 1 nm on the electron transporting layer 2114 to form an electron injecting layer 2115.

Lastly, a film of aluminum was formed to a thickness of 200 nm on the electron injecting layer 2115 by an evaporation method employing resistance heating to form a second electrode 2104. Accordingly, a light-emitting element 1a was manufactured.

(Comparative Light-Emitting Element 1b)

A comparative light-emitting element 1b was formed like the light-emitting element 1a by using the same substrate and using tris(8-quinolinolato)aluminum(III) (abbreviation: Alq) instead of BOx2PQ. That is, a film of tris(8-quinolinolato) aluminum(III) (abbreviation: Alq) was formed to a thickness of 30 nm to form the electron transporting layer 2114. Except for the electron transporting layer 2114, the comparative light-emitting element 1a was formed like the light-emitting element 1a.

The light-emitting element 1a, and the comparative light-emitting element 1b obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 23:
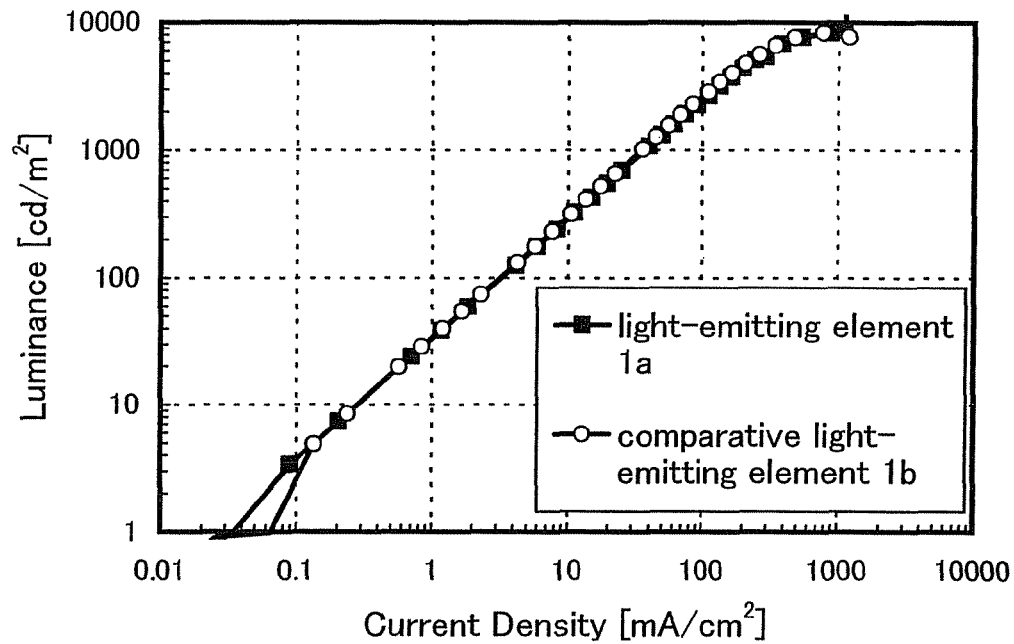
FIG. 23 is a graph showing current density-luminance characteristics of light-emitting elements manufactured in Embodiment 3.
Figure 24:
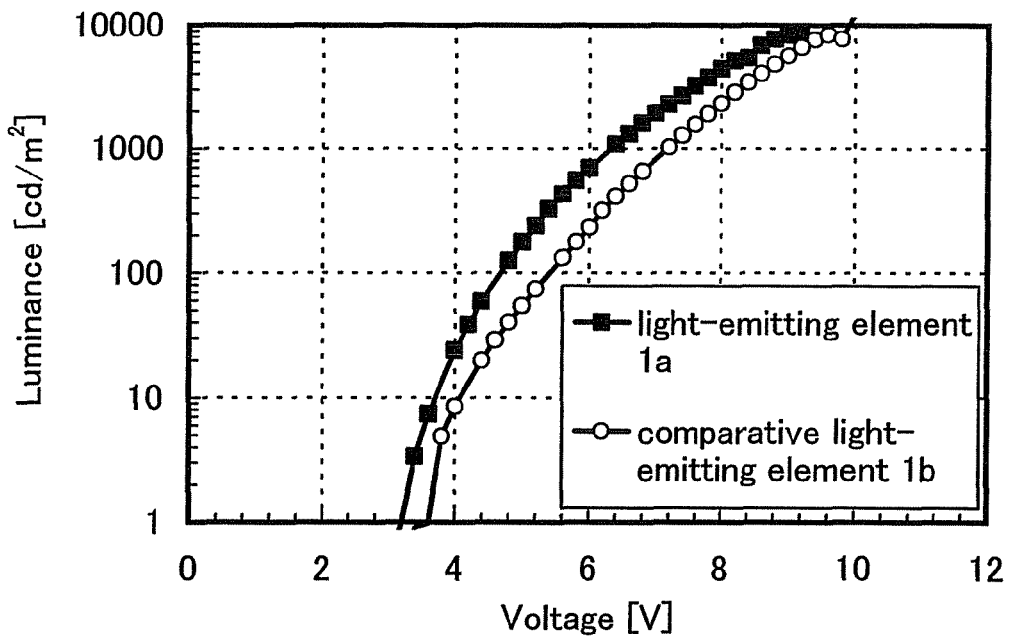
FIG. 24 is a graph showing voltage-luminance characteristics of light-emitting elements manufactured in Embodiment 3.
Figure 25:
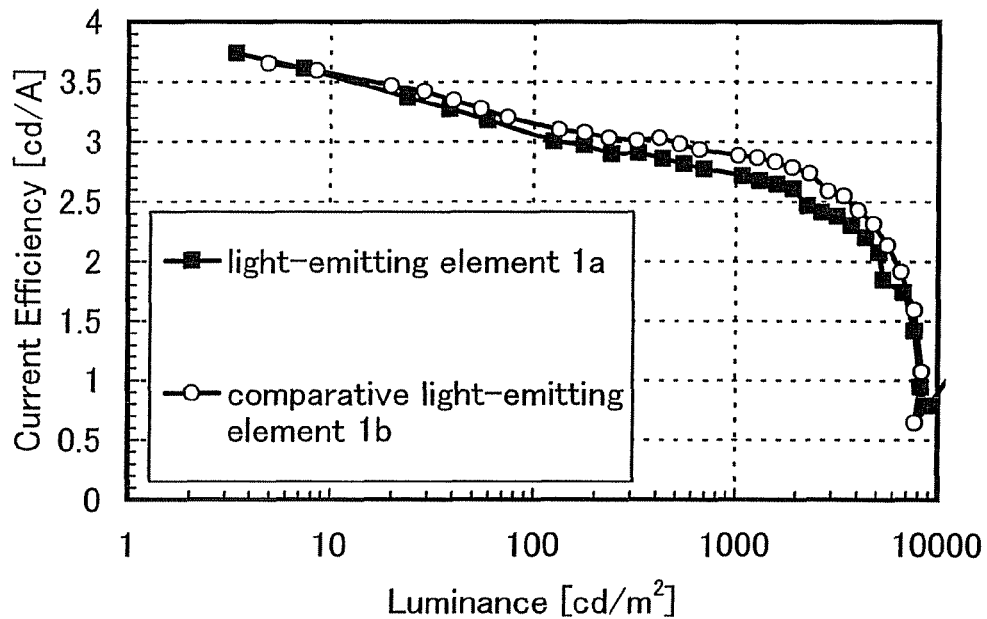
FIG. 25 is a graph showing luminance-current efficiency characteristics of light-emitting elements manufactured in Embodiment 3.
Figure 26:
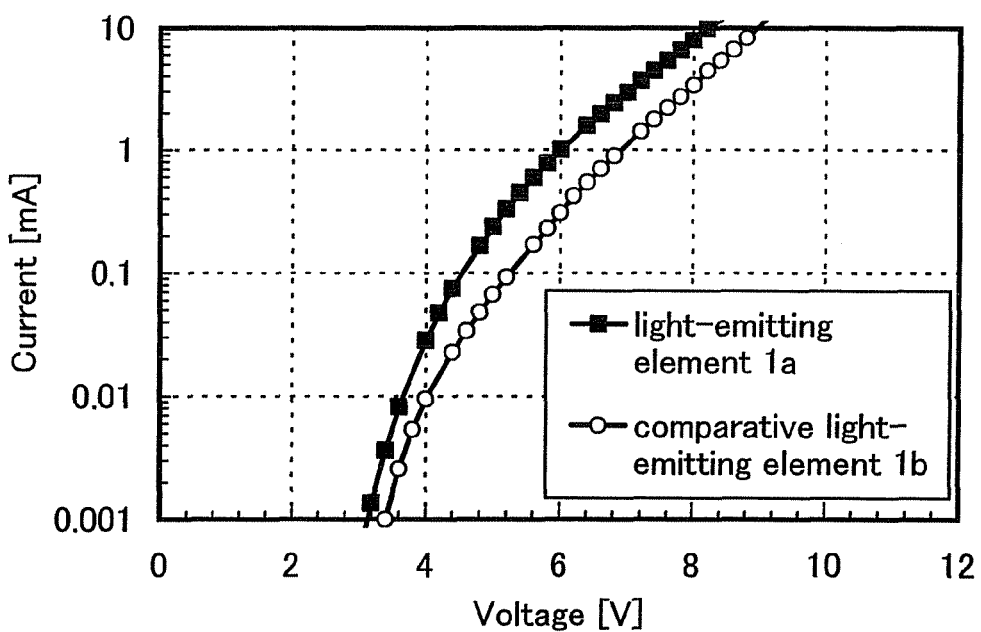
FIG. 26 is a graph showing voltage-current characteristics of light-emitting elements manufactured in Embodiment 3.

FIG. 23 shows current density-luminance characteristics of the light-emitting element 1a and the comparative light-emitting element 1b. FIG. 24 shows voltage-luminance characteristics. FIG. 25 shows luminance-current efficiency characteristics. FIG. 26 shows voltage-current characteristics. Note that FIGS. 23 and 24 show raw measurement data and FIGS. 25 and 26 show the results of calculations based on the measurement data.

Figure 27:
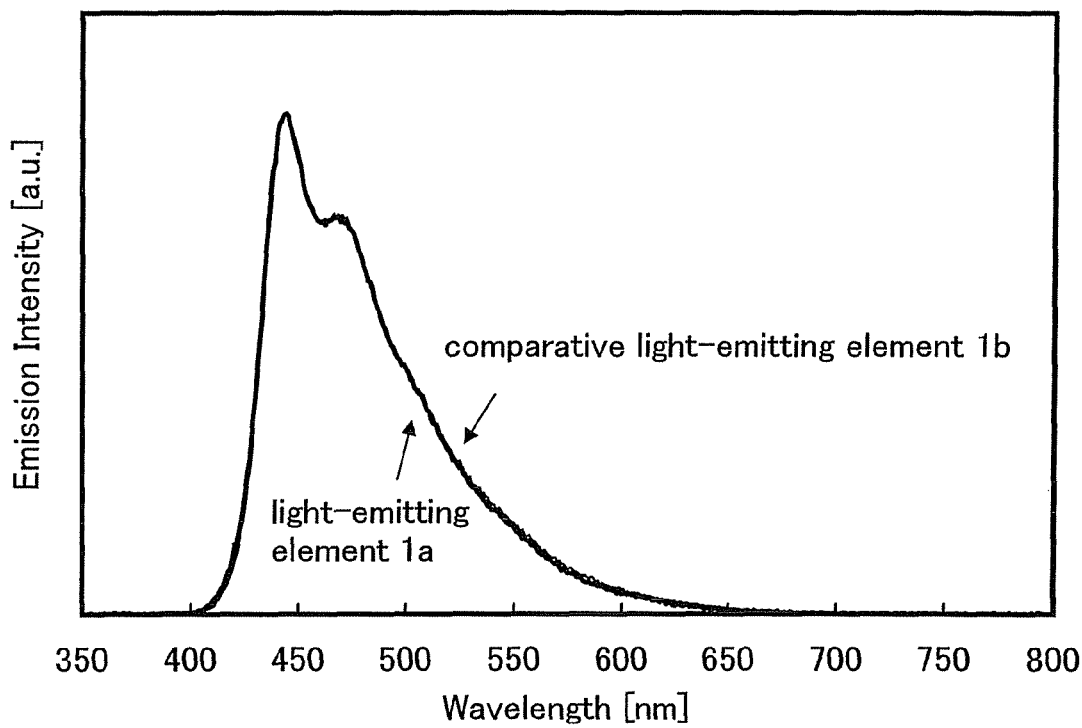
FIG. 27 is a graph showing an emission spectrum of light-emitting elements manufactured in Embodiment 3.

FIG. 27 shows emission spectra when a current of 1 mA flows. It can be seen from FIG. 27 that light emission of each of the light-emitting element 1a and the comparative light-emitting element 1a results from YGA2S.

The comparative light-emitting element 1b provides blue light emission where the CIE chromaticity coordinates are (x=0.16, y=0.17) when the luminance is 1030 cd/m². The current efficiency is 2.9 cd/A when the luminance is 1030 cd/m². When the luminance is 1030 cd/m², the voltage is 7.2 V; the current density, 35.5 mA/cm²; and the power efficiency, 1.3 lm/W.

On the other hand, the light-emitting element 1a provides blue light emission where the CIE chromaticity coordinates are (x=0.16, y=0.16) when the luminance is 1080 cd/m². The current efficiency is 2.7 cd/A when the luminance is 1080 cd/m². When the luminance is 1080 cd/m², the voltage is 6.4 V; the current density, 39.6 mA/cm²; and the power efficiency, 1.3 lm/W.

It can be seen from FIG. 26 that the light-emitting element 1a requires lower voltage than the comparative light-emitting element 1b to allow the same amount of electric current to flow. That is, by application of the present invention, electric current flows more easily when voltage is applied. Accordingly, it can be considered that a quinoxaline derivative of the present invention has an excellent electron transporting property.

It can also be seen from FIG. 25 that the light-emitting element 1a has the same or the substantially the same current efficiency as the comparative light-emitting element 1b. Thus, as shown in FIG. 24, the light-emitting element 1a requires lower voltage than the comparative light-emitting element 1b to provide the same luminance.

Figure 28:
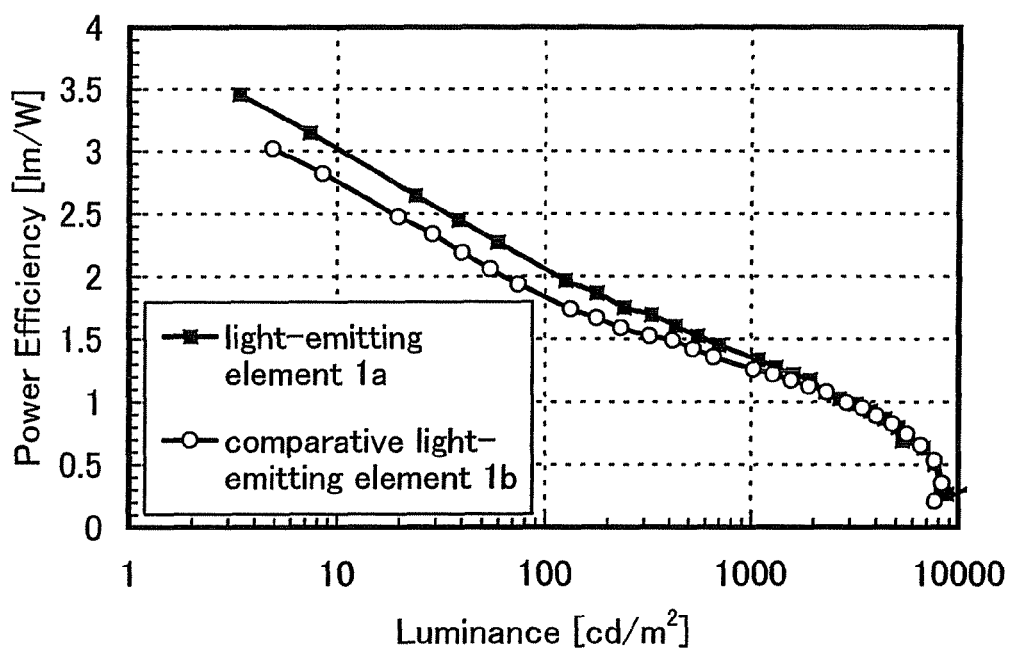
FIG. 28 is a graph showing luminance-power efficiency characteristics of light-emitting elements manufactured in Embodiment 3.

FIG. 28 shows luminance-power efficiency characteristics of the light-emitting element 1a and the comparative light-emitting element 1b. It can be seen from FIG. 28 that the light-emitting element 1a consumes less power than the comparative light-emitting element 1b in the range of practical luminance (100 to 1000 cd/m²).

That is, it can be seen that the light-emitting element 1a requires lower voltage and consumes less power than the comparative light-emitting element 1b to provide the same luminance.

By application of the present invention, a light-emitting element with low driving voltage can be obtained. In addition, a light-emitting element which consumes less power can be obtained. Furthermore, the light-emitting element of the present invention has high luminance that can be outputted at low voltage because of low driving voltage, which can be estimated from the luminance-voltage characteristics of this embodiment.

Embodiment 4

Figure 29:
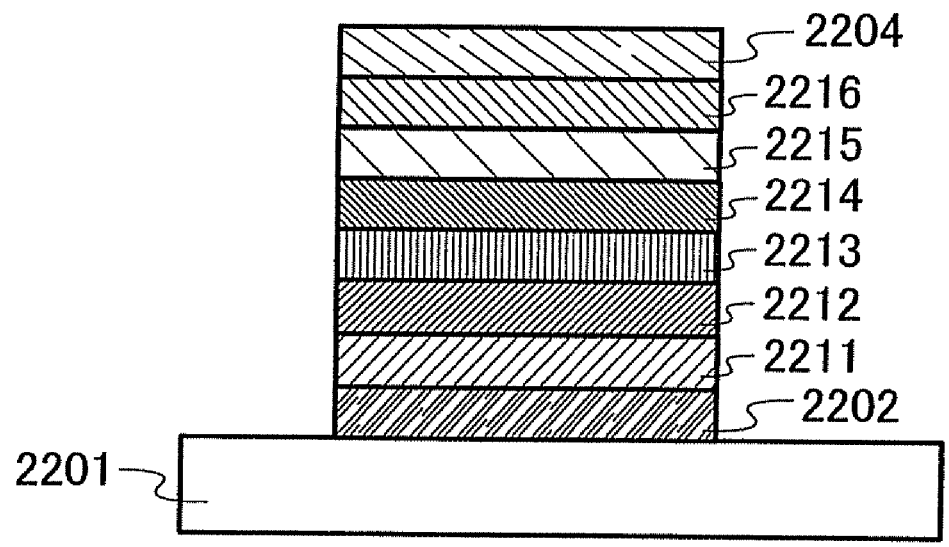
FIG. 29 illustrates a light-emitting element of an embodiment.

In this embodiment, a light-emitting element of the present invention will be described with reference to FIG. 29. Structural formulae of materials used in this embodiment are shown below. The materials, the structural formulae of which have already been shown, are omitted.

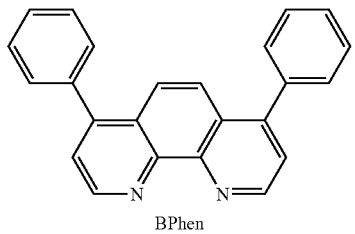

BPhen

Methods for manufacturing light-emitting elements of this embodiment are hereinafter described.
(Light-Emitting Element 2a)

First, a film of indium tin oxide containing silicon oxide (ITSO) was formed over a glass substrate 2201 by a sputtering method to form a first electrode 2202. Note that the thickness was 110 nm and the electrode area was 2 mm×2 mm.

Next, the substrate was fixed to a substrate holder provided in a vacuum evaporation apparatus such that the side on which the first electrode 2202 was formed faced downward. After the pressure in a film formation chamber was lowered to approximately $10^{-4}$ Pa, a layer 2211 containing a composite material of an organic compound and an inorganic compound was formed on the first electrode 2202 by co-evaporation of 4,4'-bis[N-(1-naphthyl)-N-phenylamino]biphenyl (abbreviation: NPB) and molybdenum(VI) oxide. The thickness was 50 nm and the weight ratio of NPB to molybdenum(VI) oxide was adjusted to be 4:1 (=NPB:molybdenum oxide). Note that a co-evaporation method refers to an evaporation method by which evaporation is concurrently conducted from a plurality of evaporation sources in one treatment chamber.

Next, a film of 4,4'-bis[N-(1-naphthyl)-N-phenylamino] biphenyl (abbreviation: NPB) was formed to a thickness of 10 nm on the layer 2211 containing a composite material by an evaporation method employing resistance heating to form a hole transporting layer 2212.

Then, a light-emitting layer 2213 was formed to a thickness of 30 nm on the hole transporting layer 2212 by co-evaporation of 9-[4-(10-phenyl-9-anthryl)phenyl]-9H-carbazole (abbreviation: CzPA) and N,N'-bis[4-(9H-carbazol-9-yl)phenyl]-N,N'-diphenylstilbene-4,4'-diamine (abbreviation: YGA2S). Here, the weight ratio of CzPA to YGA2S was adjusted to be 1:0.04 (=CzPA: YGA2S).

After that, a film of 3-phenyl-2-[4'-(benzoxazol-2-yl)biphenyl-4-yl]quinoxaline (abbreviation: BOx1PQ) represented by the structural formula (101), which is synthesized by Embodiment 1, was formed to a thickness of 20 nm on the light-emitting layer 2213 by an evaporation method employing resistance heating to form an electron transporting layer (A) 2214. In addition, a film of bathophenanthroline (abbreviation: BPhen) was formed to a thickness of 10 nm on the electron transporting layer (A) 2214 to form an electron transporting layer (B) 2215. Thus, the light-emitting element of this embodiment has a structure in which two electron transporting layers are stacked.

Furthermore, a film of lithium fluoride was formed to a thickness of 1 nm on the electron transporting layer (B) 2115 to form an electron injecting layer 2116.

Lastly, a film of aluminum was formed to a thickness of 200 nm on the electron injecting layer 2216 by an evaporation method employing resistance heating to form a second electrode 2204. Accordingly, a light-emitting element 2a was manufactured.

<Comparative Light-Emitting Element 2b>

A comparative light-emitting element 2b was formed like the light-emitting element 2a by using the same substrate and using tris(8-quinolinolato)aluminum(III) (abbreviation: Alq) instead of BOx1PQ. That is, a film of tris(8-quinolinolato) aluminum(III) (abbreviation: Alq) was formed to a thickness of 20 nm to form the electron transporting layer (A) 2214. Except for the electron transporting layer (A) 2214, the comparative light-emitting element 2b was formed like the light-emitting element 2a.

The light-emitting element 2a and the comparative light-emitting element 2b obtained as described above were placed in a nitrogen-atmosphere glove box and were sealed so that the light-emitting elements were not exposed to the air. Then, the operating characteristics of the light-emitting elements were measured. Note that the measurement was performed at room temperature (in an atmosphere kept at 25° C.).

Figure 30:
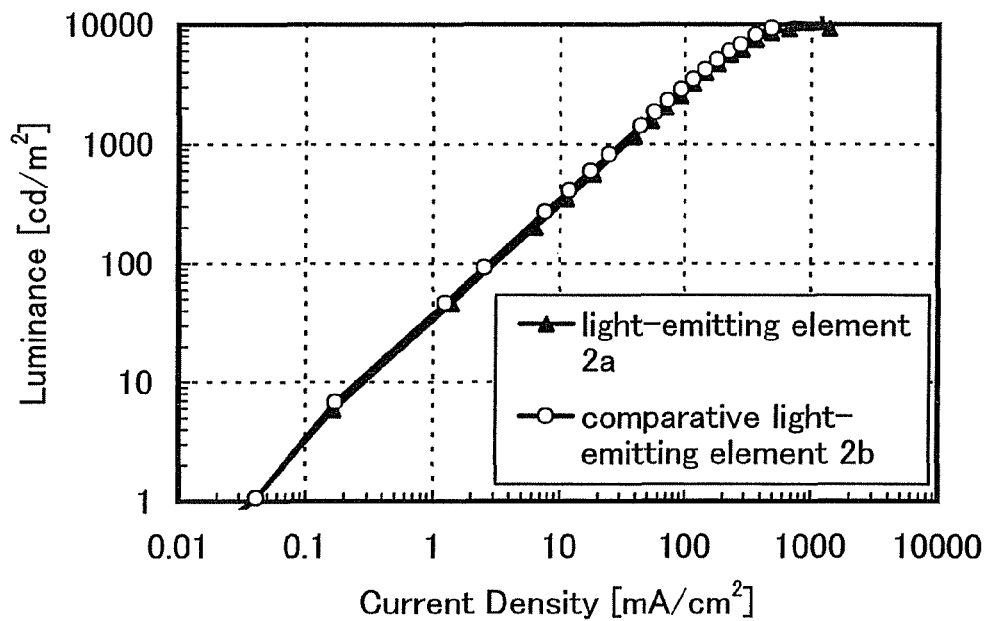
FIG. 30 is a graph showing current density-luminance characteristics of light-emitting elements manufactured in Embodiment 4.
Figure 31:
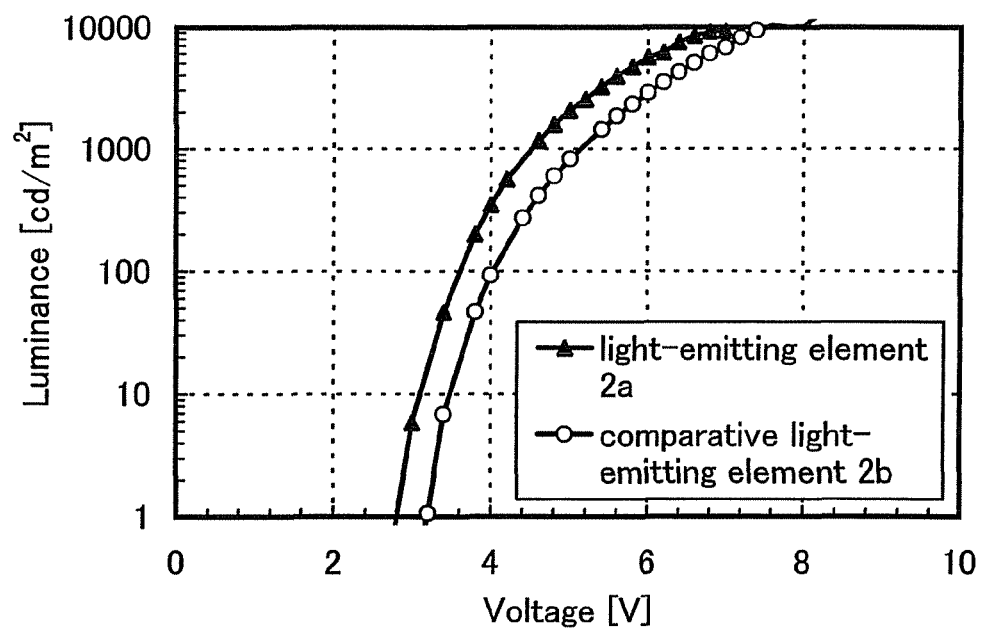
FIG. 31 is a graph showing voltage-luminance characteristics of light-emitting elements manufactured in Embodiment 4.
Figure 32:
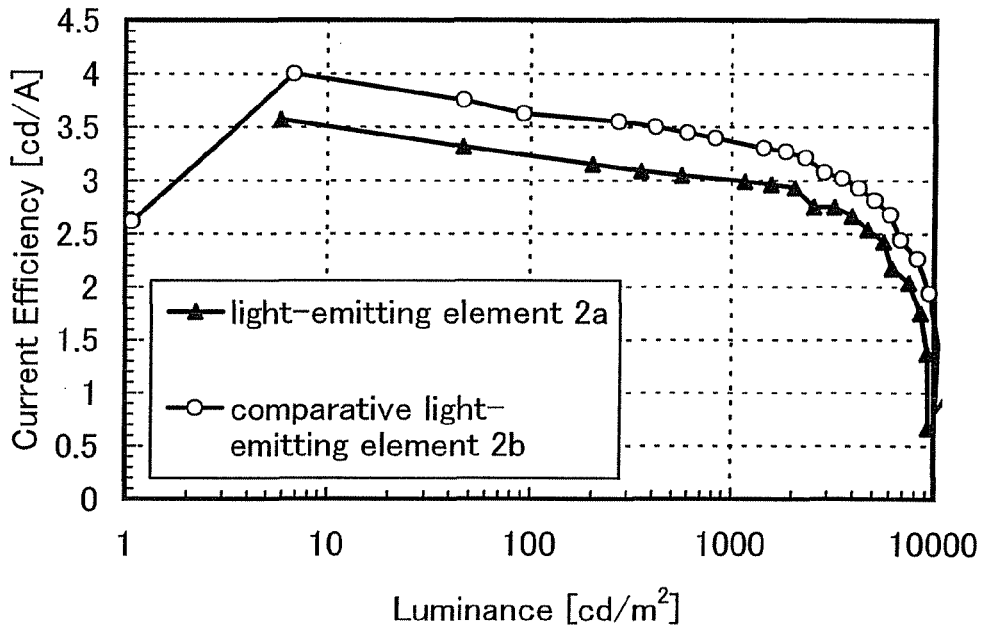
FIG. 32 is a graph showing luminance-current efficiency characteristics of light-emitting elements manufactured in Embodiment 4.
Figure 33:
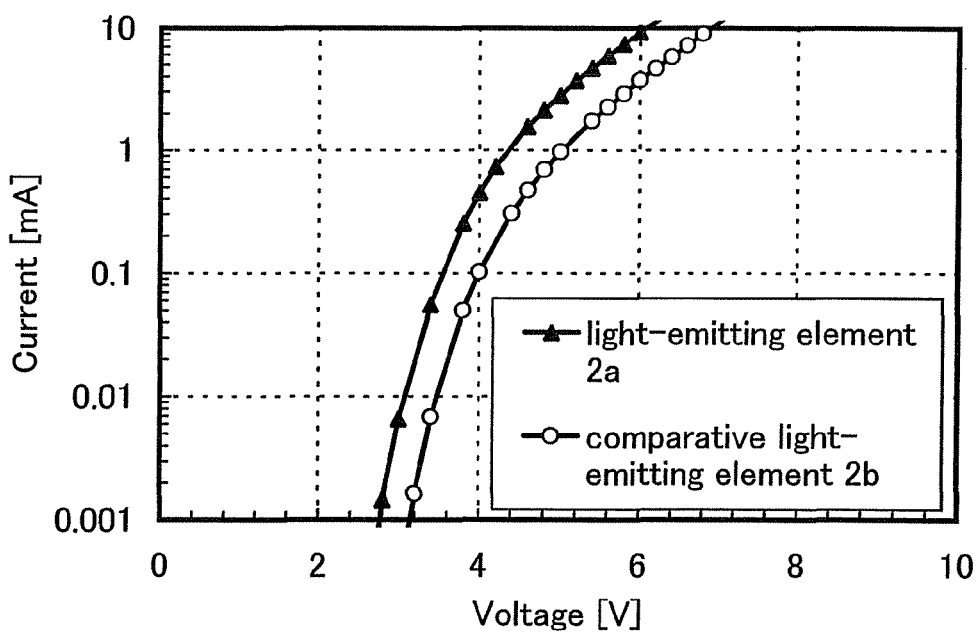
FIG. 33 is a graph showing voltage-current characteristics of light-emitting elements manufactured in Embodiment 4.

FIG. 30 shows current density-luminance characteristics of the light-emitting element 2a and the comparative light-emitting element 2b. FIG. 31 shows voltage-luminance characteristics. FIG. 32 shows luminance-current efficiency characteristics. FIG. 33 shows voltage-current characteristics. Note that FIGS. 30 and 31 show raw measurement data and FIGS. 32 and 33 show the results of calculations based on the measurement data.

Figure 34:
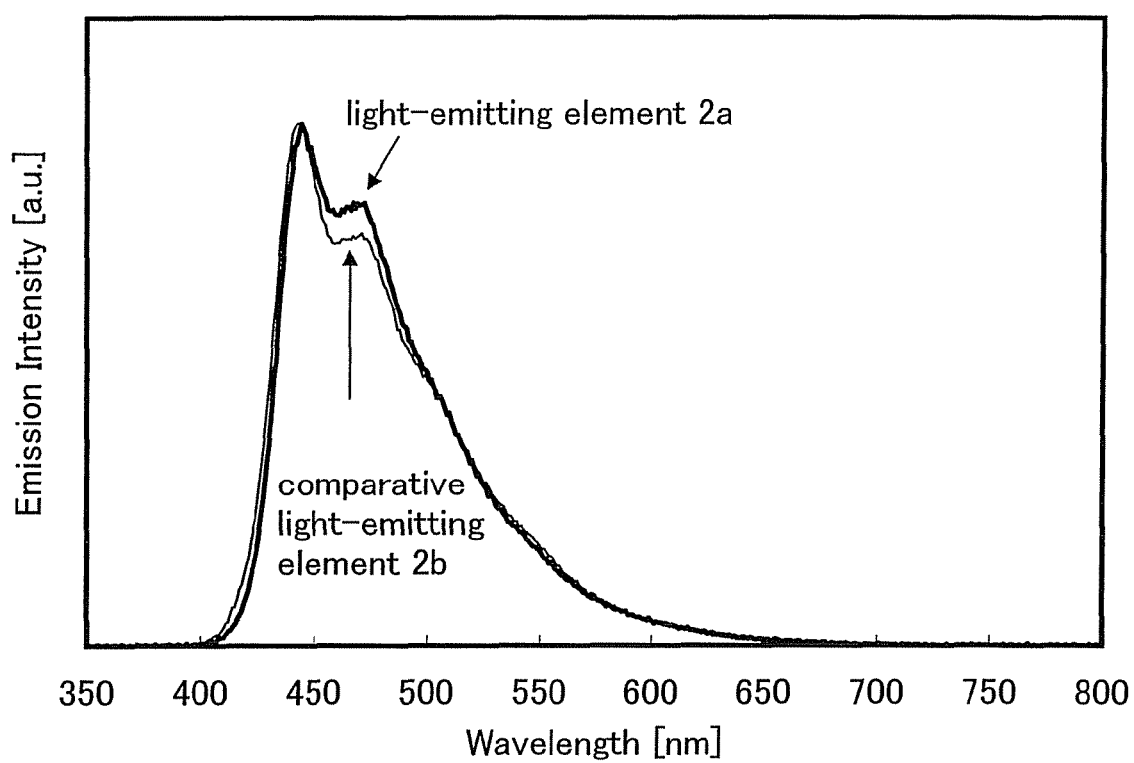
FIG. 34 is a graph showing emission spectra of light-emitting elements manufactured in Embodiment 4.

FIG. 34 shows emission spectra when a current of 1 mA flows. It can be seen from FIG. 34 that light emission of each of the light-emitting element 2a and the comparative light-emitting element 2b results from YGA2S.

The comparative light-emitting element 2b provides blue light emission where the CIE chromaticity coordinates are (x=0.16, y=0.18) when the luminance is 830 cd/m$^2$. The current efficiency is 3.4 cd/A when the luminance is 830 cd/m$^2$. When the luminance is 830 cd/m$^2$, the voltage is 5.0 V; the current density, 24.3 mA/cm$^2$; and the power efficiency, 2.1 lm/W.

The light-emitting element 2a provides blue light emission where the CIE chromaticity coordinates are (x=0.16, y=0.17) when the luminance is 1160 cd/m$^2$. The current efficiency is 3.0 cd/A when the luminance is 1160 cd/m$^2$. When the luminance is 1160 cd/m$^2$, the voltage is 4.6 V; the current density, 38.9 mA/cm$^2$; and the power efficiency, 2.0 lm/W.

It can be seen from FIG. 33 that the light-emitting element 2a requires lower voltage than the comparative light-emitting element 2b to allow the same amount of electric current to flow. That is, by application of the present invention, electric current flows more easily when voltage is applied. Accordingly, it can be considered that a quinoxaline derivative of the present invention has an excellent electron transporting property.

It can also be seen from FIG. 32 that the light-emitting element 2a has the same or substantially the same current efficiency as the comparative light-emitting element 2b. Thus, as shown in FIG. 31, the light-emitting element 2a requires lower voltage than the comparative light-emitting element 2b to provide the same luminance.

That is, it can be seen that the light-emitting element 2a requires lower voltage than the comparative light-emitting element 2b to provide the same luminance.

By application of the present invention, a light-emitting element with low driving voltage can be obtained. In addition, a light-emitting element of the present invention has high luminance that can be outputted at the certain voltage because of low driving voltage, which can be estimated from the luminance-voltage characteristics of this embodiment.

This application is based on Japanese Patent Application serial no. 2007-310065 filed with Japan Patent Office on Nov. 30, 2007, the entire contents of which are hereby incorporated by reference.

What is claimed is:

1. A quinoxaline derivative represented by a general formula (G11),

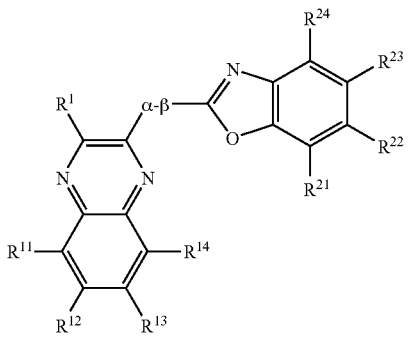

(G11)

wherein in the formula, α represents a substituted or unsubstituted arylene group having 6 to 13 carbon atoms; β represents a substituted or unsubstituted arylene group having 6 to 13 carbon atoms; $R^{21}$ to $R^{24}$ are the same or different from each other and each represent hydrogen or an alkyl group having 1 to 4 carbon atoms; $R^1$ represents an alkyl group having 1 to 4 carbon atoms or a substituted or unsubstituted aryl group having 6 to 13 carbon atoms; and $R^{11}$ to $R^{14}$ are the same or different from each other and each represent any of hydrogen, an alkyl group having 1 to 4 carbon atoms, or a substituted or unsubstituted aryl group having 6 to 13 carbon atoms.

2. The quinoxaline derivative according to claim 1, wherein β is a phenylene group.

3. The quinoxaline derivative according to claim 1,
wherein α is a phenylene group,
wherein β is a phenylene group, and
wherein each of $R^{11}$ to $R^{14}$ is a hydrogen.

4. The quinoxaline derivative according to claim 1,
wherein α is a phenylene group,
wherein β is a phenylene group,
wherein each of $R^{11}$ to $R^{14}$ is a hydrogen, and
wherein a para position of α is bonded to a para position of β.

5. The quinoxaline detivative according to claim 1,
wherein $R^1$ is a phenyl group or a biphenyl group.

6. A quinoxaline detivative represented by a general formula (G21),

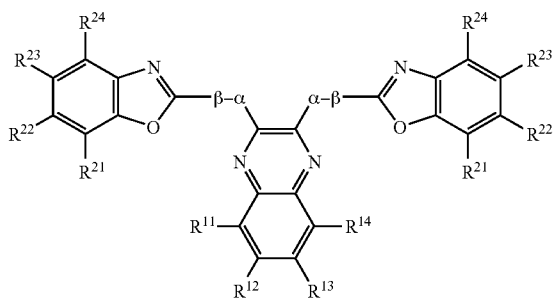

(G21)

wherein in the formula, α represents a substituted or unsubstituted arylene group having 6 to 13 carbon atoms; β represents a substituted or unsubstituted arylene group having 6 to 13 carbon atoms; $R^{21}$ to $R^{24}$ are the same or different from each other and each represent hydrogen or an alkyl group having 1 to 4 carbon atoms; and $R^{11}$ to $R^{14}$ are the same or different from each other and each represent any of hydrogen, an alkyl group having 1 to 4 carbon atoms, or a substituted or unsubstituted aryl group having 6 to 13 carbon atoms.

7. The quinoxaline derivative according to claim 6, wherein β is a phenylene group.

8. The quuinoxaline detivative according to claim 6,
wherein α is a phenylene group,
wherein β is a phenylene group, and
wherein each of $R^{11}$ to $R^{14}$ is a hydrogen.

9. The quinoxaline derivative according to claim 6,
wherein α is a phenylene group,
wherein β is a phenylene group,
wherein each of $R^{11}$ to $R^{14}$ is a hydrogen, and
wherein a para position of α is bonded to a para position of β.

10. The quinoxaline derivative according to claim 6,
wherein $R^1$ is a phenyl group or a biphenyl group.

11. A light-emitting element comprising a quinoxaline derivative between a pair of electrodes,
wherein the quinoxaline derivative is represented by a general formula (G11), and

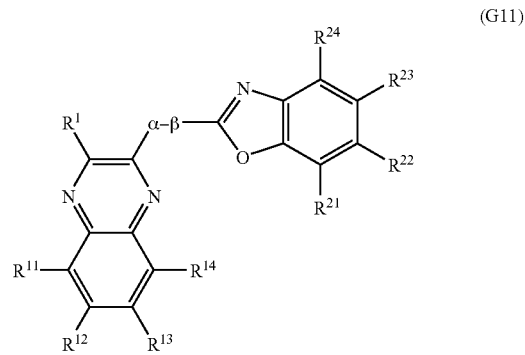

(G11)

wherein in the formula, α represents a substituted or unsubstituted arylene group having 6 to 13 carbon atoms; β represents a substituted or unsubstituted arylene group having 6 to 13 carbon atoms; $R^{21}$ to $R^{24}$ are the same or different from each other and each represent hydrogen or an alkyl group having 1 to 4 carbon atoms; $R^1$ represents an alkyl group having 1 to 4 carbon atoms or a substituted or unsubstituted aryl group having 6 to 13 carbon atoms; and $R^{11}$ to $R^{14}$ are the same or different from each other and each represent any of hydrogen, an alkyl group having 1 to 4 carbon atoms, or a substituted or unsubstituted aryl group having 6 to 13 carbon atoms.

12. The light-emitting element according to claim 11, wherein β is a phenylene group.

13. The light-emitting element according to claim 11,
wherein α is a phenylene group,
wherein β is a phenylene group, and
wherein each of $R^{11}$ to $R^{14}$ is a hydrogen.

14. The light-emitting element according to claim 11,
wherein α is a phenylene group,
wherein β is a phenylene group,
wherein each of $R^{11}$ to $R^{14}$ is a hydrogen, and
wherein a para position of α is bonded to a para position of β.

15. The light-emitting element according to claim 11, wherein $R^1$ is a phenyl group or a biphenyl group.

16. The light-emitting element according to claim 11 comprising:
a light-emitting layer; and
a layer including the quinoxaline detivative derivative between an anode and a cathode,
wherein the layer including the quinoxaline derivative is provided between the light-emitting layer and the cathode.

17. A light-emitting element comprising a quinoxaline derivative between a pair of electrodes,
wherein the quinoxaline derivative is represented by a general formula (G21), and

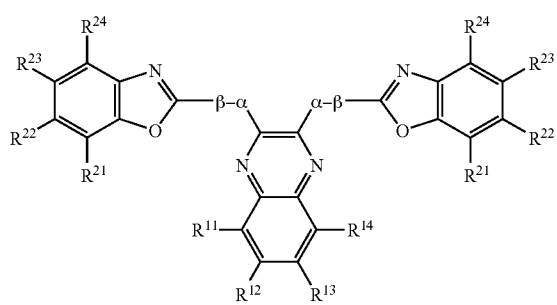

(G21)

wherein in the formula, α represents a substituted or unsubstituted arylene group having 6 to 13 carbon atoms; β represents a substituted or unsubstituted arylene group having 6 to 13 carbon atoms; $R^{21}$ to $R^{24}$ are the same or different from each other and each represent hydrogen or an alkyl group having 1 to 4 carbon atoms; and $R^{11}$ to $R^{14}$ are the same or different from each other and each represent any of hydrogen, an alkyl group having 1 to 4 carbon atoms, or a substituted or unsubstituted aryl group having 6 to 13 carbon atoms.

18. The light-emitting element according to claim 17, wherein β is a phenylene group.

19. The light-emitting element according to claim 17, wherein α is a phenylene group,
wherein β is a phenylene group, and
wherein each of $R^{11}$ to $R^{14}$ is a hydrogen.

20. The light-emitting element according to claim 17, wherein α is a phenylene group,
wherein β is a phenylene group,
wherein each of $R^{11}$ to $R^{14}$ is a hydrogen, and
wherein a para position of α is bonded to a para position of β.

21. The light-emitting element according to claim 17, wherein $R^1$ is a phenyl group or a biphenyl group.

22. The light-emitting element according to claim 17 comprising:
a light-emitting layer; and
a layer including the quinoxaline derivative between an anode and a cathode,
wherein the layer including the quinoxaline derivative is provided between the light-emitting layer and the cathode.

23. An electronic device comprising a display portion including a light-emitting element and a control circuit,
wherein the light emitting element comprises a quinoxaline derivative between a pair of electrodes,
wherein the quinoxaline derivative is represented by a general formula (G11), and

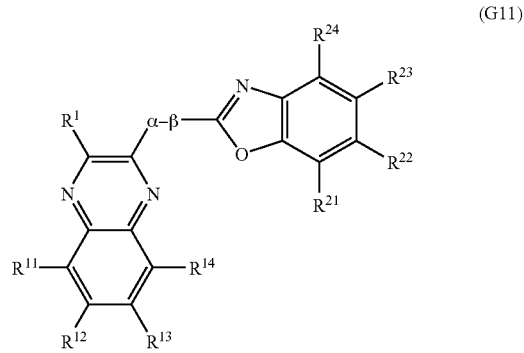

(G11)

wherein in the formula, α represents a substituted or unsubstituted arylene group having 6 to 13 carbon atoms; β represents a substituted or unsubstituted arylene group having 6 to 13 carbon atoms; $R^{21}$ to $R^{24}$ are the same or different-from each other and each represent hydrogen or an alkyl group having 1 to 4 carbon atoms; $R^1$ represents an alkyl group having 1 to 4 carbon atoms or a substituted or unsubstituted aryl group having 6 to 13 carbon atoms; and $R^{11}$ to $R^{14}$ are the same or different from each other and each represent any of hydrogen, an alkyl group having 1 to 4 carbon atoms, or a substituted or unsubstituted aryl group having 6 to 13 carbon atoms.

24. An electronic device comprising a display portion including a light-emitting element and a control circuit,
wherein the light emitting element comprises a quinoxaline derivative between a pair of electrodes,
wherein the quinoxaline derivative is represented by a general formula (G21), and

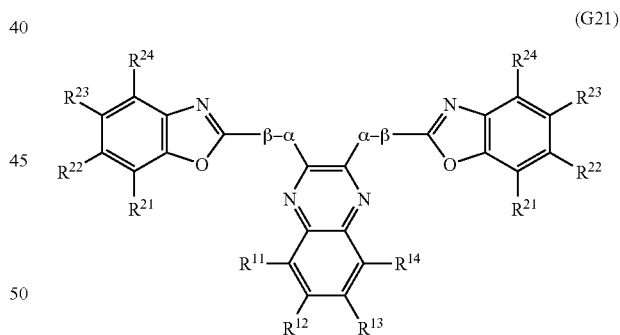

(G21)

wherein in the formula, α represents a substituted or unsubstituted arylene group having 6 to 13 carbon atoms; β represents a substituted or unsubstituted arylene group having 6 to 13 carbon atoms; $R^{21}$ to $R^{24}$ are the same or different from each other and each represent hydrogen or an alkyl group having 1 to 4 carbon atoms; and $R^{11}$ to $R^{14}$ are the same or different from each other and each represent any of hydrogen, an alkyl group having 1 to 4 carbon atoms, or a substituted or unsubstituted aryl group having 6 to 13 carbon atoms.

* * * * *